US008277816B2

(12) United States Patent
Yusibov et al.

(10) Patent No.: US 8,277,816 B2
(45) Date of Patent: Oct. 2, 2012

(54) *BACILLUS ANTHRACIS* ANTIGENS, VACCINE COMPOSITIONS, AND RELATED METHODS

(75) Inventors: Vidadi Yusibov, Havertown, PA (US); Vadim Mett, Newark, DE (US); Konstantin Musiychuck, Swarthmore, PA (US); Marina Skarjinskaia, Newark, DE (US)

(73) Assignee: Fraunhofer USA, Inc., Plymouth, MI (US)

( * ) Notice: Subject to any disclaimer, the term of this patent is extended or adjusted under 35 U.S.C. 154(b) by 1521 days.

(21) Appl. No.: 11/706,576

(22) Filed: Feb. 13, 2007

(65) Prior Publication Data

US 2011/0142870 A1    Jun. 16, 2011

Related U.S. Application Data

(60) Provisional application No. 60/773,255, filed on Feb. 13, 2006.

(51) Int. Cl.
*A61K 39/00* (2006.01)

(52) U.S. Cl. ............... 424/192.1; 424/185.1; 424/190.1; 424/193.1; 424/201.1; 424/246.1; 530/350

(58) Field of Classification Search ........................ None
See application file for complete search history.

(56) References Cited

U.S. PATENT DOCUMENTS

| | | | |
|---|---|---|---|
| 4,196,265 A | 4/1980 | Koprowski et al. |
| 4,270,537 A | 6/1981 | Romaine |
| 4,522,811 A | 6/1985 | Eppstein et al. |
| 4,596,556 A | 6/1986 | Morrow et al. |
| 4,653,728 A | 3/1987 | Mochizuki et al. |
| 4,683,202 A | 7/1987 | Mullis |
| 4,790,824 A | 12/1988 | Morrow et al. |
| 4,816,567 A | 3/1989 | Cabilly et al. |
| 4,886,499 A | 12/1989 | Cirelli et al. |
| 4,935,496 A | 6/1990 | Kudo et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,223,409 A | 6/1993 | Ladner et al. |
| 5,312,335 A | 5/1994 | McKinnon et al. |
| 5,316,931 A | 5/1994 | Donson et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,403,484 A | 4/1995 | Ladner et al. |
| 5,417,662 A | 5/1995 | Hjertman et al. |
| 5,427,908 A | 6/1995 | Dower et al. |
| 5,466,220 A | 11/1995 | Brennerman |
| 5,480,381 A | 1/1996 | Weston |
| 5,500,360 A | 3/1996 | Ahlquist et al. |
| 5,502,167 A | 3/1996 | Waldmann et al. |
| 5,503,627 A | 4/1996 | McKinnon et al. |
| 5,520,639 A | 5/1996 | Peterson et al. |
| 5,527,288 A | 6/1996 | Gross et al. |
| 5,530,101 A | 6/1996 | Queen et al. |
| 5,545,806 A | 8/1996 | Lonberg et al. |
| 5,545,807 A | 8/1996 | Surani et al. |
| 5,558,864 A | 9/1996 | Bendig et al. |
| 5,565,332 A | 10/1996 | Hoogenboom et al. |
| 5,569,189 A | 10/1996 | Parsons |
| 5,569,825 A | 10/1996 | Lonberg et al. |
| 5,580,717 A | 12/1996 | Dower et al. |
| 5,585,089 A | 12/1996 | Queen et al. |
| 5,591,828 A | 1/1997 | Bosslet et al. |
| 5,599,302 A | 2/1997 | Lilley et al. |
| 5,602,242 A | 2/1997 | Ahlquist et al. |
| 5,625,126 A | 4/1997 | Lonberg et al. |
| 5,633,425 A | 5/1997 | Lonberg et al. |
| 5,639,641 A | 6/1997 | Pedersen et al. |
| 5,649,912 A | 7/1997 | Peterson |
| 5,658,727 A | 8/1997 | Barbas et al. |
| 5,661,016 A | 8/1997 | Lonberg et al. |
| 5,667,988 A | 9/1997 | Barbas et al. |
| 5,681,722 A | 10/1997 | Newman et al. |
| 5,693,493 A | 12/1997 | Robinson et al. |
| 5,693,761 A | 12/1997 | Queen et al. |
| 5,693,762 A | 12/1997 | Queen et al. |
| 5,698,417 A | 12/1997 | Robinson et al. |
| 5,698,426 A | 12/1997 | Huse et al. |
| 5,702,892 A | 12/1997 | Mulligan-Kehoe |
| 5,704,911 A | 1/1998 | Parsons |
| 5,705,154 A | 1/1998 | Dalie et al. |

(Continued)

FOREIGN PATENT DOCUMENTS

EP            404097         6/1990

(Continued)

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Accession CAA4959, Apr. 18, 2005.
Ahlquist et al., "Gene Expression Vectors Derived from Plant RNA Viruses," *Current Communications in Molecular Biology—Viral Vectors*, (Ed., Gluzman et al.) 183-189, 1988.
Akol and Murray, "*Trypanosoma congolense*: Susceptibility of cattle to cyclical challenge," *Exp. Parasitol.*, 55:386-393, 1983.

(Continued)

*Primary Examiner* — Jennifer Graser

(74) *Attorney, Agent, or Firm* — Fish & Richardson P.C.

(57) ABSTRACT

The present invention relates to the intersection of the fields of immunology and protein engineering, and particularly to antigens and vaccines useful in prevention of infection by *Bacillus anthracis*. Provided are recombinant protein antigens, compositions, and methods for the production and use of such antigens and vaccine compositions.

39 Claims, 6 Drawing Sheets

U.S. PATENT DOCUMENTS

| | | | |
|---|---|---|---|
| 5,733,743 | A | 3/1998 | Johnson et al. |
| 5,750,078 | A | 5/1998 | Shitara et al. |
| 5,759,817 | A | 6/1998 | Barbas |
| 5,770,403 | A | 6/1998 | Dalie et al. |
| 5,770,429 | A | 6/1998 | Lonberg et al. |
| 5,846,795 | A | 12/1998 | Ahlquist et al. |
| 5,855,866 | A | 1/1999 | Thorpe et al. |
| 5,877,289 | A | 3/1999 | Thorpe et al. |
| 5,888,789 | A | 3/1999 | Rodriguez et al. |
| 5,893,397 | A | 4/1999 | Peterson et al. |
| 5,965,132 | A | 10/1999 | Thorpe et al. |
| 5,993,412 | A | 11/1999 | Deily et al. |
| 6,042,832 | A | 3/2000 | Koprowski et al. |
| 6,044,555 | A | 4/2000 | Jacob et al. |
| 6,093,399 | A | 7/2000 | Thorpe et al. |
| 6,103,511 | A | 8/2000 | Li et al. |
| 6,261,535 | B1 | 7/2001 | Thorpe et al. |
| 6,331,415 | B1 | 12/2001 | Cabilly et al. |
| 6,448,070 | B1 | 9/2002 | Koprowski et al. |
| 6,524,825 | B1 | 2/2003 | Mizzen et al. |
| 6,649,172 | B2 | 11/2003 | Johnson |
| 6,734,173 | B1 | 5/2004 | Wu et al. |
| 6,740,740 | B2 | 5/2004 | Garger et al. |
| 6,797,491 | B2 | 9/2004 | Neefe, Jr. et al. |
| 6,841,659 | B2 | 1/2005 | Turpen et al. |
| 6,852,319 | B2 | 2/2005 | Hein et al. |
| 7,888,135 | B2 | 2/2011 | Tarleton et al. |
| 2004/0092470 | A1 | 5/2004 | Leonard et al. |
| 2004/0093643 | A1 | 5/2004 | Ensley |
| 2004/0170606 | A1 | 9/2004 | Palmer et al. |
| 2004/0268442 | A1 | 12/2004 | Miller et al. |
| 2005/0026291 | A1 | 2/2005 | Fedorkin et al. |
| 2005/0042229 | A1 | 2/2005 | Yang et al. |
| 2005/0048074 | A1 | 3/2005 | Cardineau et al. |
| 2005/0054820 | A1 | 3/2005 | Wu et al. |
| 2005/0114920 | A1 | 5/2005 | Yusibov et al. |
| 2005/0186621 | A1 | 8/2005 | Galarza et al. |
| 2006/0008473 | A1 | 1/2006 | Yang et al. |
| 2006/0265787 | A1 | 11/2006 | Piruzian et al. |
| 2007/0275014 | A1 | 11/2007 | Yusibov et al. |
| 2008/0124272 | A1 | 5/2008 | Yusibov et al. |
| 2009/0324634 | A1 | 12/2009 | Knapp et al. |
| 2010/0227373 | A1 | 9/2010 | Yusibov et al. |
| 2011/0027304 | A1 | 2/2011 | Yusibov et al. |
| 2011/0059130 | A1 | 3/2011 | Yusibov et al. |

FOREIGN PATENT DOCUMENTS

| | | |
|---|---|---|
| WO | WO9311161 | 6/1993 |
| WO | WO9602555 | 2/1996 |
| WO | WO9612028 | 4/1996 |
| WO | WO9713537 | 4/1997 |
| WO | WO9737705 | 10/1997 |
| WO | WO9814595 | 4/1998 |
| WO | WO9845331 | 10/1998 |
| WO | WO9907860 | 2/1999 |
| WO | WO0020612 | 4/2000 |
| WO | WO0025574 | 5/2000 |
| WO | WO0046350 | 8/2000 |
| WO | WO0200892 | 1/2002 |
| WO | WO03040179 | 5/2003 |
| WO | WO03076568 | 9/2003 |
| WO | WO2004043886 | 5/2004 |
| WO | WO2004058797 | 7/2004 |
| WO | WO2005023177 | 3/2005 |
| WO | WO2005026375 | 3/2005 |
| WO | WO2005049839 | 6/2005 |
| WO | WO2005056052 | 6/2005 |
| WO | WO2005067620 | 7/2005 |
| WO | WO2005081905 | 9/2005 |
| WO | WO2005120567 | 12/2005 |
| WO | WO2006003018 | 1/2006 |
| WO | WO2006124712 | 11/2006 |
| WO | WO2007089753 | 8/2007 |
| WO | WO2007095304 | 8/2007 |
| WO | WO2007095318 | 8/2007 |
| WO | WO2007149715 | 12/2007 |
| WO | WO2008021959 | 2/2008 |
| WO | WO2008033105 | 3/2008 |
| WO | WO2008033159 | 3/2008 |
| WO | WO2008048945 | 4/2008 |
| WO | WO2008110937 | 9/2008 |
| WO | WO2008134643 | 11/2008 |
| WO | WO2009009759 | 1/2009 |
| WO | WO2009026397 | 2/2009 |
| WO | WO2009054708 | 4/2009 |
| WO | WO2009058355 | 5/2009 |
| WO | WO2010036970 | 4/2010 |
| WO | WO2010037046 | 4/2010 |

OTHER PUBLICATIONS

Alignment of 11706573-6 to SEQ ID No. 6 in parent matter U.S. Appl. No. 10/558,109, filed Feb. 24, 2009.

Alignment of 11706573-30 to SEQ ID No. 6 in parent matter U.S. Appl. No. 10/558,109, filed Feb. 24, 2009.

Alignment of 11706576-12 to SEQ ID No. 6 in parent matter U.S. Appl. No. 10/558,109 on Feb. 24, 2009.

Alignment of 12110877-30 to SEQ ID No. 6 in parent matter U.S. Appl. No. 10/558,109 on Feb. 24, 2009.

Altschul et al., "Basic local alignment search tool," *J. Mol. Biol.*, 215:403-410, 1990.

Altschul et al., "Gapped BLAST and PSI-BLAST: a new generation of protein database search programs," *Nucleic Acids Res.* 25: 3389-3402, 1997.

Alvarez et al., "Plant-made subunit vaccine against pneumonic and bubonic plague is orally immunogenic in mice," *Vaccine* 24(14):2477-2490, 2006.

Ay et al., "Crystal structures and properties of de novo circularly permuted 1,3-1,4-beta-glucanases," *Proteins* 30(2):155-67, 1998.

Barfield et al., "Gene Transfer in Plants of *Brassica juncea* Using *Agrobacterium tumefaciens* Mediated Transformation," *Plant Cell Reports* 10(6/7):308-314, 1991.

Bates, "Genetic Transformation of Plants by Protoplast Electroporation," *Mol. Biotechnol.* 2(2):135-145, 1994.

Beachy et al., "A Genetic Map for the Cowpea Strain of TMV," *Virology* 73:498-507, 1976.

Bedell et al., "The E6-E7 Region of Human Papillomavirus Type 18 Is Sufficient for Transformation of NIH 3T3 and Rat-1 Cells," *J. Virol.* 61:3635-3640, 1987.

Bisaro et al., "Genetic Analysis of Tomato Golden Mosaic Virsu," *Current Communications in Molecular Biology: Viral Vectors*, Cold Spring Harbor Laboratory, Cold Spring Harbor, NY, pp. 172-189, 1988.

Bol et al., "A Functional Equivalence of Top Component a RNA and Coat Protein in the Initiation of Infection by Alfalfa Mosaic Virus," *Virology* 46:73-85, 1971.

Bol et al., "Alfalfa Mosaic Virus and Ilarviruses: Involvement of Coat Protein in Multiple Steps of the Replication Cycle," *J. Gen. Virol.* 80:1089-1102, 1999.

Boyd and Beeson, "Animal models for evaluation of compounds against influenza viruses," *J. Antimicrobial Chemotherapy* 1(Suppl.):43-47, 1975.

Brett et al., "Immunization against influenza A virus: comparison of conventional inactivated, live-attenuated and recombinant baculovirus produced purified hemagglutinin and neuraminidase vaccines in a murine model system," *Virology* 339(2):273-280, 2005.

Broothaerts et al., "Gene Transfer to Plants by Diverse Species of Bacteria," *Nature* 433:629-633, 2005.

Bruening et al., "In Vitro and in Vivo Translation of the Ribonucleic Acids of a Cowpea Strain of Tobacco Mosaic Virus," *Virology* 71:498-517, 1976.

Buscaglia et al., "Tandem amino acid repeats from *Trypanosoma cruzi* shed antigens increase the half-life of proteins in blood," *Blood* 93(6):2025-2032, 1999.

Calandrelli et al., "Purification and characterization of thermostable eylanase and beta-xylosidase by the termophilic bacterium *Bacillus termantarcticus*," *Res. Microbiol.* 155(4):283-289, 2004.

Canizares et al., "Use of viral vectors for vaccine production in plants," *Immunol. Cell Biol.* 83:263-270, 2005.

Chen et al., "Complete sequence of the binary vector pBI121 and its application in cloning T-DNA insertion from transgenic plants," *Mol. Breed.* 11:287-293, 2003.

Chen et al., "Induction and relief of nasal congestion in ferrets infected with influenza virus," *Int. J. Exp. Path.* 76:55-64, 1995.

Chica et al., "Semi-rational approaches to engineering enzyme activity: combining the benefits of directed evolution and rational design," *Curr. Opin. Biotechnol.* 16:378-384, 2005.

Chichester et al., "Immunogenicity of a subunit vaccine against *Bacillus anthracia,*" *Vaccine* 25:3111-3114, 2007.

Corbel, "Reasons for instability of bacterial vaccines," *Developments in Biological Standardization* 87:113-124, 1996.

Costa et al., "Conformational stability and antibody response to the 18kDa heat-shock protein formulated into different vehicles," *Applied Biochemistry and Biotechnology* 73(1):19-28, 1998.

Crossway et al., "Integration of foreign DNA following microinjection of tobacco mesophyll protoplasts," *Mol. Gen. Genet.* 202:179-185, 1986.

Curtis and Nam, "Transgenic radish (*Raphanus sativus* L. *longipinnatus* Bailey) by floral-dip method—plant development and surfactant are important in optimizing transformation efficiency," *Transgenic Research* 10(4):363-371, 2001.

Davies et al., "Affinity improvement of single antibody VH domains: residues in all three hypervariable regions affect antigen binding," *Immunotechnology* 2(3):169-179, 1996.

DeGraff, et al., "In Vitro Evidence that the Coat Protein of Alfalfa Mosaic Virus Plays a Direct Role in the Regulation of Plus and Minus RNA Synthesis Implications for the Life Cycle of Alfalfa Mosaic Virus," *Virology* 208: 583-589, 1995.

Desfeux et al., "Female Reproductive Tissues Are the Primary Target of *Agrobacterium*-Mediated Transformation by the *Arabidopsis* Floral-Dip Method," *Plant Physiology* 123(3):895-904, 2000.

Dréau et al., "Human Papilloma Virus in Melanoma Biopsy Specimens and Its Relation to Melanoma Progression," *Annals of Surgery* 231:664-671, 2000.

Eckert et al., "DNA polymerase fidelity and the polymerase chain reaction," *PCR Methods and Applications* 1:17-24, 1991.

Fenton et al., "Immunity to Influenza in Ferrets. XIV: Comparative Immunity Following Infection or Immunization With Live or Inactivated Vaccine," *Br. J. Exp. Path.* 62:297, 1981.

Fernando et al., "Expression, purification and immunological characterization of the transforming protein E7, from cervical cancer-associated human papillomavirus type 16," *Clin. Exp. Immunol.* 115:397-403, 1999.

Flick-Smith et al., "A Recombinant Carboxy-Terminal Domain of the Protective Antigen of *Bacillus anthracis* Protects Mice against Anthrax Infection," *Infect. Immun.* 70:1653-1656, 2002.

Fraley et al., "Liposome-Mediated Delivery of Tobacco Mosaic Virus RNA into Tobacco Protoplasts: A Sensitive Assay for Monitoring Liposome-Protoplast Interactions," *Proc. Natl. Acad. Sci. USA* 79:1859-1863, 1982.

Fraley et al., "Expression of Bacterial Genes in Plant Cells," *Proc. Natl. Acad. Sci. USA* 80:4803-4807, 1983.

Franconi et al., "Plant-derived Human Papillomavirus 16 E7 Oncoprotein Induces Immune Response and Specific Tumor Production," *Cancer Res.* 62:3654, 2002.

Fromm et al., "Expression of Genes Transferred into Monocot and Dicot Plant Cells by Electroporation," *Proc. Natl. Acad. Sci. USA* 82:5824, 1985.

Fütterer et al., "Use of DNA Plant Viruses and Plant Viral Expression Signals for Gene Expression in Plants and Plant Protoplasts," *Current Communications in Molecular Biology—Viral Vectors*, (Ed., Gluzman et al.) 1988, 178-182.

Gelvin, "*Agrobacterium*-Mediated Plant Transformation: the Biology behind the 'Gene-Jockeying' Tool," *Microbiol. Mol Biol. Rev.* 67(1):16-37, 2003.

Giri and Narasu, "Transgenic hairy roots: recent trends and applications," *Biotechnol. Adv.* 18:1-22, 2000.

Gleba et al., "Magnifection—a new platform for expressing recombinant vaccines in plants," *Vaccine* 23:2042-2048, 2005.

Goldenkova et al., "A Thermostable *Clostridium thermocellum* Lichenase-based Reporter System for Studying the Gene Expression Regulation in Prokaryotic and Eukaryotic Cells," *Mol. Biol.* 36:698-704, 2002.

Green et al., "Transient protein expression in three *Pisum sativum* (green pea) varieties," *Biotechnology Journal* 4(2):230-237, 2009.

Grierson et al., "Plant Viruses," *Plant Molecular Biology*, Blackie, London, pp. 126-146, 1984.

Gu et al., "Protection against anthrax toxin by vaccination with a DNA plasmid encoding anthrax protective antigen," *Vaccine* 17:340, 1999.

Hahn et al., "Native-like in-vivo folding of a circularly permuted jellyroll protein shown by crystal structure analysis," *Proc. Natl. Acad. Sci., USA* 91(22):10417-10421, 1994.

Hansen et al., "Attachment of antibodies to sterically stabilized liposomes: evaluation, comparison and optimization of coupling procedures," *Biochim. Biophys. Acta.* 1239(2):133-44, 1995.

Hellens et al., "pGreen: a versatile and flexible binary Ti vector for *Agrobacterium*-mediated plant transformation," *Plant Molecular Biology* 42:819-832, 2000.

Herbert and Lumsden, "*Trypanosoma brucei*: A rapid 'matching' method for estimating the host's parasitemia," *Exp. Parasitol.* 40:427, 1976.

Hobson et al., "The role of serum haemagglutination-inhibiting antibody in protection against challenge infection with influenza A2 and B viruses," *J. Hyg.* 70:767, 1972.

Holt et al., "Domain antibodies: proteins for therapy," *Trends Biotechnol.* 21(11):484-490, 2003.

Huang et al., "Plant-derived measles virus hemagglutinin protein induces neutralizing antibodies in mice," *Vaccine* 19(15-16):2163-2171, 2001.

Hull et al., "Human-derived, plant-produced monoclonal antibody for the treatment of anthrax," *Vaccine* 23:2082-2086, 2005.

Hunter et al., "Messenger RNA for the Coat Protein of Tobacco Mosaic Virus," *Nature* 260:759-760, 1976.

Ishida et al., "A combinatorial approach to producing sterically stabilized (Stealth) immunoliposomal drugs," *FEBS Lett.* 460(1):129-33, 1999.

Ishikawa et al., "In Vitro Mutagenesis of the Putative Replicase Genes of Tobacco Mosaic Virus," *Nucleic Acids Res.* 14: 8291-8308, 1986.

Jaspars et al., "Plant Viruses with a Multipartite Genome," *Adv. Virus Res.* 19:37-149, 1974.

Jefferson et al., "GUS fusions: beta-glucuronidase as a sensitive and versatile gene fusion marker in higher plants," *EMBO J* 6:3901-3907, 1987.

Johnson et al., Respiratory syncytial virus (RSV) G glycoprotein is not necessary for vaccine-enhanced disease induced by immunization with formalin-inactivated RSV, *J. Virol* 78(11):6024-32, 2004.

Kao et al., "A Method for High-frequency Intergeneric Fusion of Plant Protoplasts," *Planta* 115:355, 1974.

Kapila et al., "An *Agrobacterium*-mediated transient gene expression system for intact leaves," *Plant Sci.* 122:101-108, 1997.

Kapusta et al., "A plant-derived edible vaccine against hepatitis B virus," *FASEB J.* 13:1796-1799, 1999.

Karlin and Altschul, "Methods for assessing the statistical significance of molecular sequence features by using general scoring schemes," *Proc. Natl. Acad. Sci. USA* 87:2264-2268, 1990.

Karlin and Altschul, "Applications and statistics for multiple high-scoring segments in molecular sequences," *Proc. Natl. Acad. Sci. USA* 90:5873-5877, 1993.

Kikkert et al., "Biological Projectiles (Phage, Yeast, Bacteria) for Genetic Transformation of Plants," In Vitro *Cell. Dev. Bio.—Plant* 35(1):43-50, 1999.

Klein et al., "High-velocity microprojectiles for delivering nucleic acids into living cells," *Nature* 327:70-73, 1987.

Knapp et al., "Conundrum of the lack of defective RNAs (dRNAs) associated with Tobamovirus infections: dRNAs that can move are not replicated by the wild-type virus; dRNAs that are replicated by the wild-type virus do not move," *J. Virol.* 75:5518, 2001.

Knudsen and Muller, "Transformation of the developing barley endosperm by particle bombardment," *Planta* 185:330-336, 1991.

Kohler and Milstein, "Continuous cultures of fused cells secreting antibody of predefined specificity," Nature 256:495, 1975.

Krebber et al., "Reliable cloning of functional antibody variable domains from hybridomas and spleen cell repertoires employing a reengineered phage display system," J. Immunol. Methods 201:35-55, 1997.

Krens et al., "In vitro transformation of plant protoplasts with Ti-plasmid DNA," Nature 296:72-74, 1982.

Kubler-Kielb et al., "Long-lasting and transmission-blocking activity of antibodies to Plasmodium falciparum elicited in mice by protein conjugates of Pfs25," Proc. Natl. Acad. Sci. USA 104(1):293-298, 2007.

Kumagai, et al., "Rapid, High-Level Expression of Glycosylated Rice α-Amylase in Transfected Plants by an RNA Viral Vector," Gene 245: 169-174, 2000.

Lambkin et al., "Strong local and systemic protective immunity induced in the ferret model by an intranasal virosome-formulated influenza subunit vaccine," Vaccine 22:4390, 2004.

Lawton et al., "Expression of a Soybean (3-Conclycinin Gene under the Control of the Cauliflower Mosaic Virus 35S and 19S Promoters in Transformed Petunia Tissues," Plant Mol. Biol 9:315-324, 1987.

Leite et al., "Expression of correctly processed human growth hormone in seeds of transgenic tobacco plants," Molecular Breeding 6:47-53, 2000.

Lensen et al., "Measurement by membrane feeding of reduction in Plasmodium falciparum transmission induced by endemic sera," Trans. R. Soc. Trop. Med. Hyg. 90(1):20-22, 1996.

Lewandowski and Dawson, "Deletion of Internal Sequences Results in Tobacco Mosaic Virus Defective RNAs That Accumulate to High Levels without Interfering with Replication of the Helper Virus," Virology 251:427-437, 1998o.

Lim et al., "An Anthrax Lethal Factor-Neutralizing Monoclonal Antibody Protects Rats before and after Challenge with Anthrax Toxin," Infection and Immunity 73:6547, 2005.

Lin et al., "Treatment of Established Tumors with a Novel Vaccine That Enhances Major Histocompatibility Class II Presentation of Tumor Antigen," Cancer Research 56:21, 1996.

Little et al., "Passive Protection by Polyclonal Antibodies against Bacillus anthracia Infection in Guinea Pigs," Infect. Immun. 65:5171-5175, 1997.

Little et al., "Of mice and men: hybridoma and recombinant antibodies," Immunology Today 21(8):364-370, 2000.

Loesch-Fries et al., "Expression of Alfalfa Mosaic Virus RNA 4 cDNA Transcripts In Vitro and In Vivo," Virology 146:177-187, 1985.

Lorence and Verpoorte, "Gene transfer and expression in plants," Methods Mol. Biol. 267:329-350, 2004.

Lubega et al, "Immunization with a tubulin-rich preparation from Trypanosoma brucei confers broad protection against African trypanosomosis," Exp. Parasitol. 102:9-22, 2002.

Lubega et al., "Trypanosoma brucei: anti-tubulin antibodies specifically inhibit trypanosome growth in culture," Exp. Parasitol. 102:134-142, 2002.

Maassab et al., "Evaluation of a Cold-Recombinant Invluenza Virus Vaccine in Ferrets," J. Infectious Diseases 146(6):780-790, 1982.

Maliga et al., "Transient Cycloheximide Resistance in a Tobacco Cell Line," Mol. Gen. Genet. 149:267-271, 1976.

Mathew, Plant Viruses Online—Cassava Indian mosaic bigeminvirus (http://imagels.uidaho.eduivide/), downloaded on Feb. 21, 2006, 5 pgs.

Mattila et al., "Fidelity of DNA synthesis by the Thermococcus litoralis DNA polymerase—an extremely heat stable enzyme with proofreading activity," Nucleic Acids Res. 19:4967, 1991.

McCormick et al., "Rapid Production of Specific Vaccines for Lymphoma by Expression of the Tumor-Derived Single-Chain Fv Epitopes in Tobacco Plants," Proc. Natl. Acad. Sci. USA 96:703-708, 1999.

McHugh et al., "Improved stability of a protein vaccine through elimination of a partially unfolded state," Protein Science 13:2736-2743, 2004.

Mellin et al., "Human Papillomavirus (HPV) DNA in Tonsillar Cancer: Clinical Correlates, Rise of Relapse, and Survival," Int. J. Cancer 89:300-304, 2000.

Menczel et al. "Streptomycin Resistant and Sensitive Somatic Hybrids of Nicotiana tabacum + Nicotiana knightiana: Correlation of Resistance to N. tabacum Plastids," Theor. Appl. Genet. 59:191-195, 1981.

Meshi et al., "Function of the 30 kd Protein of Tobacco Mosaic Virus: Involvement in Cell-to-Cell Movement and Dispensability for Replication" EMBO J. 6: 2557-2563, 1987.

Mett et al., "A plant-produced influenza subunit vaccine protects ferrets against virus challenge," Influenza and Other Respiratory Viruses 2(1):33-40, 2008.

Mett et al., "A plant-produced plague vaccine candidate confers protection to monkeys," Vaccine 25(16):3014-3017, 2007.

Moayeri et al., "The roles of anthrax toxin in pathogenesis," Curr. Opin. Michrobiol. 7(1):19-24, 2004.

Modelska et al., "Immunization against rabies with plant-derived antigen," Proc. Nati. Acad. Sci., USA 95:2481-2485, 1998.

Moreira et al., "A Thermostable Maltose-tolerant α-anylase from Asperillgus tamarii," J. Basic Microbiology 44:29-35, 2004.

Murashige et al., "A Revised Medium for Rapid Growth and Bio Assays with Tobacco Tissue Cultures," Physiologia Plantarum 15:473, 1962.

Musiychuk et al., "A launch vector for the production of vaccine antigens in plants," Influenza and Other Respiratory Viruses 1:1, 2007.

Musiychuk et al., "Preparation and properties of Clostridium thermocellum lichenase deletion variants and their use for construction of bifunctional hybrid proteins," Biochemistry(MOSC) 65(12): 1397-1402, 2000.

Nagy et al., "Thermal stability of chemically denatured green fluorescent protein (GFP)—A preliminary study," Thermochimica Acta 410(1), abstract, 2004.

Nass, "Anthrax Vaccine—Model of a Response to the Biologic Warfare Threat," Infect. Dis. Clin. North Am. 13:187-208, 1999.

NCBI GenBank Accession No. ABP96852, "Influenza A virus" (A/Egypt/2616-NAMRU3/2007(H5N1)) hemagglutinin (HA) gene, complete CDS, 30, Apr. 2007.

NCBI GenBank Accession No. AAS93885, "Influenza A virus" (A/Cheju/274/2002(H3N2)) neuraminidase (NA) gene, complete CDS, 25, Apr. 2004.

Neeleman et al., "Role of Alfalfa Mosaic Virus Coat Protein Gene in Symptom Formation," Virology 181: 687-693, 1991.

Neeleman et al., "Infection of Tobacco with Alfalfa Mosaic Virus cDNAs Sheds Light on the Early Function of the Coat Protein," Virology 196: 883-887, 1993.

Park et al., "Molecular Biology of Cervical Cancer and Its Precursors," Cancer 76:1902-1913, 1995.

Peres et al., "Shoot regeneration capacity from roots and transgenic hairy roots of tomato cultivars and wild related species," Plant Cell, Tissue, and Organ Culture 65:37-44, 2001.

Petosa et al., "Crystal structure of the anthrax toxin protective antigen," Nature 385:833-838, 1997.

Pilon-Smits et al., "Overexpression of ATP Sulfurylase in Indian Mustard Leads to Increased Selenate Uptake, Reduction, and Tolerance," Plant Physiol. 119(1): 123-132, 1999.

Piruzian et al., "A reporter system for prokaryotic and eukaryotic cells based on the thermostable lichenase from Clostridium thermocellum," Mol. Genet. Genomics 266(5):778-86, 2002, Epub Nov. 27, 2001.

Piruzian et al., "The use of a thermostable B-glucanase gene from Clostridium thermocellum as a reporter gene in plants," Mol. Gen. Genet. 257(50): 561-567, 1998.

Potter et al., "Immunity to Influenza in Ferrets II. Influence of Adjuvants on Immunization," Br. J. Exp. Pathol. 53:168, 1972.

Potter et al., "Immunity to Influenza in Ferrets VI. Immunization with Adjuvanted Vaccines," Arch. Gesamte Virusforsch. 42:285, 1973.

Potter et al., "Immunity to influenza in ferrets V. Immunization with inactivated virus in adjuvant 65," J. Hyq. Lond. 71:97, 1973.

Qian et al., "Conjugating recombinant proteins to Pseudomonas aeruginosa ExoProtein A: A strategy for enhancing immunogenicity of malaria vaccine candidate," Vaccine 25(20):3923-3933, 2007.

Qing et al., "Transformation of Pakchoi (Brassica rapa L. ssp. Chinensis) by Agrobacterium Infiltration," Molecular Breeding 1:67-72, 2000.

Rao and Ravishankar, "Plant cell cultures: Chemical factories of secondary metabolites," *Biotechnol. Adv.* 20:101-153, 2002.

Rasooly-Balaban, "Trypanosome microtubule-associated protein p15 as a vaccine for the prevention of African sleeping sickness," *Vaccine* 22(8):1007-1015, 2004.

Reinstein et al., "Degradation of the E7 human papillomavirus oncoprotein by the ubiquitin-proteasome system: targeting via ubiquitination of the N-terminal residue," *Oncogene* 19: 5944-5950, 2000.

Riva et al., "*Agrobacterium tumefaciens*: a natural tool for plant transformation," *Electronic J. Biotech.* 1(3):118-133, 1998.

Saito, et al., "Long-Distance Movement and Viral Assembly of Tobacco Mosaic Virus Mutants," *Virology* 176: 329-336, 1990.

Santi et al., "Protection conferred by recombinant *Yersinia pestis* antigens produced by a rapid and highly scalable plant expression system," *Proc. Natl. Acad. Sci. USA* 103(4): 861-866, 2006.
Scheiblauer et al., "Pathogenicity of influenza A/Seal/Mass/1/80 virus mutants for mammalian species," *Arch Virol.* 140: 341-384, 1995.
Schell et al., "Transgenic Plants as Tools to Study the Molecular Organization of Plant Genes," *Science* 237: 1176-1183, 1987.
Seedorf et al., "Human Papillomavirus Type 16 DNA Sequence," *Virology* 145:181, 1985.
Sen et al., "Developments in directed evolution for improving enzyme functions," *Appl. Biochem. Biotechnol.*, 143(3):212-23, 2007.
Shima et al., "Hyperthermaphilic and salt-dependent formytransferase from *Methanopyrus kanleri," Biochem. Soc. Trans.* 32:269-72, 2004.
Shivprasad et al., "Heterologous Sequences Greatly Affect Foreign Gene Expression in Tobacco Mosaic Virus-Based Vectors," *Virology* 255(2):312-23, 1999.
Singh et al., "Gln277 and Phe544 residues are involved in thermal inactivation of protective antigen of *Bacillus anthracis," Biochem. Biophys. Res. Comm.* 296:1058-1062, 2002.
Singh et al., "Study of Immunization against Anthrax with the Purified Recombinant Protective Antigen of *Bacillus anthracis," Infect. Immun.* 66:3447-3448, 1998.
Singh et al., "Thermal inactivation of protective antigen of *Bacillus anthracis* and its prevention by polyol osmolytes," *Biochem. Biophys. Res. Comm.* 322: 1029-1037, 2004.
Smahel et al., "Modified HPV16 E7 Genes as DNA Vaccine against E7-Containing Oncogenic Cells," *Virology* 281: 231-238, 2001.
Snow et al., "The global distribution of clinical episodes of *Plasmodium falciparum* malaria," *Nature* 434:214-217, 2005.
Soini et al., "Presence of human papillomavirus DNA and abnormal p53 protein accumulation in lung carcinoma," *Thorax* 51:887-893, 1996.
Spilliaert et al., "Cloning and sequencing of a Rhodothermus marinus gene, bglA, coding for a thermostable beta-glucanase and its expression in *Escherichia coli," Eur. J. Biochem.* 224(3):923-930, 1994.
Stewart et al., "Mutant barley (1→3,1→4)-β-glucan endohydrolases with enhanced thermostability," *Protein Engineering* 14(4):245-253, 2001.
Tacket et al., "Human Immune Responses to a Novel Norwalk Virus Vaccine Delivered in Transgenic Potatoes," *J. Infect. Dis.* 182:302-305, 2000.
Thanavala et al., "Immunogenicity in humans of an edible vaccine for hepatitis B," *Proc. Natl. Acad. Sci., USA* 102:3378-3382, 2005.
The World Health Organization Global Influenza Program Surveillance Network, Evolution of H5N1 Avian Influenza Viruses in Asia, 2005, *Emerging Infectious Diseases*, vol. 11, No. 10, pp. 1515-1521.
Thomas et al., "HPV-18 E6 mediated inhibition of p53 DNA binding activity is independent of E6 induced degradation," *Oncogene* 10:261-268, 1995.
Toms et al., "Behaviour in Ferrets of Swine Influenza Virus Isolated from Man," *The Lancet* pp. 68-71, Jan. 8, 1977.
Torchilin et al., "p-Nitrophenylcarbonyl-PEG-PE-liposomes: fast and simple attachment of specific ligands, including monoclonal antibodies, to distal ends of PEG chains via p-nitrophenylcarbonyl groups," *Biochim. Biophys. Acta*, 1511(2):397-411, 2001.
Tsai et al., "Crystal structure of a natural circularly permuted jellyroll protein: 1,3-1,4-beta-D-glucanase from *Fibrobacter succinogens," J. Mol. Biol.* 330(3):607-20, 2003.
Turpen et al., "Transfection of whole plants from wounds inoculated with *Agrobacterium tumefaciens* containing cDNA of tobacco mosaic virus," *J. Virol, Methods* 42:227, 1993.
Van der Kolk et al., "Evaluation of the standard membrane feeding assay (SMFA) for the determination of malaria transmission-reducing activity using empirical data," *Parasitology* 130(Pt 1):13-22, 2005 (with Erratum in: *Parasitology* 131(Pt 4):578, 2005.
Van Der Kuyl et al., "Complementation and Recombination between Alfalfa Mosaic Virus RNA3 Mutants in Tobacco Plants," *Virology* 183:731-738, 1991.
Van Der Kuyl et al., "Role of Alfalfa Mosaic Virus Coat Protein in Regulation of the Balance between Viral Plus and Minus Strand RNA Synthesis," *Virology* 185:496-499, 1991.
Van Der Vossen et al., "Early and Late Functions of Alfalfa Mosaic Virus Coat Protein Can Be Mutated Separately," *Virology* 202:891-903, 1994.
Verch et al., "Expression and assembly of a full-length monoclonal antibody in plants using a plant virus vector," *J. Immunol. Methods* 220:69-75, 1998.
Voinnet et al., "An enhanced transient expression system in plants based on suppression of gene silencing by the p19 protein of tomato bushy stunt virus," *Plant J.* 33:949-956, 2003.
Volten-Doting, Plant Viruses Online (http://image.fs.uidaho.edu/vide/descr009.htm) (downloaded May 18, 2002) (11 pgs.).
Wagner et al., "Plant virus expression systems for transient production of recombinant allergens in *Nicotiana benthamiana," Methods: A Companion to Methods in Enzymology* 32(3): 228-232, 2004.
Wang et al, "Immunogenicity of *Plasmodium yoelii* merozoite surface protein 4/5 produced in transgenic plants," *Int. J. Parasitol.* 38(1):103-110, 2007.
Wang et al., "Structural Basis for Thermostability off β-Glycosidase from the Thermophilic Eubacterium Thermus Nonproteolyticus HG102," *J. Bacteriology* 185:4248-55, 2003.
Webster et al., "Measles virus hemagglutinin protein expressed in transgenic lettuce induces neutralizing antibodies in mice following mucosal vaccination," *Vaccine* 24(17): 3538-3544, 2006.
Webster et al., "Protection of ferrets against influenza challenge with a DNA vaccine to the haemagglutinin," *Vaccine* 12(16): 1495-1498, 1994.
Wiesmuller et al., "Peptide Vaccines and Peptide Libraries," *Biol. Chem.* 382(4): 571-579, 2001.
Wilson et al., "Structure of the haemagglutinin membrane glycoprotein of influenza virus at 3 Å resolution," *Nature* 289:366, 1981.
Woo, "The Haematocrit Centrifuge Technique for the Diagnosis of African Trypanosomiasis," *Acta Tropica* 27:384, 1970.
Yusibov et al., "Antigens Produced in Plants by Infection with Chimeric Plant Viruses Immunize Against Rabies Virus and HIV-1," *Proc. Natl. Acad. Sci. USA* 94:5784-5788, 1997.
Yusibov et al., "N-Terminal Basic Amino Acids of Alfalfa Mosaic Virus Coat Protein Involved in the Initiation of Infection," *Virology* 208: 405-407, 1995.
Yusibov, et al., "Functional Significance of Three Basic N-Terminal Amino Acids of Alfalfa Mosaic Virus Coat Protein," *Virology* 242:1-5, 1998.
Yusibov et al., "Purification, characterization, assembly and crystallization of assembled alfalfa mosaic virus coat protein expressed in *Escherichia coli," J. Gen. Virol.* 77:567-573, 1996.
Yusibov et al., "Expression in plants and immunogenicity of plant virus-based experimental rabies vaccine," *Vaccine* 20:3155-3164, 2002.
Zumbach et al., "Antibodies Against Oncoproteins E6 and E7 of Human Papillomavirus Types 16 and 18 in Patients with Head-and-Neck Squamous-Cell Carcinoma," *Int. J. Cancer* 85:815-818, 2000.
Advisory Action dated Jan. 15, 2010 for U.S. Appl. No. 11/706,568 (3 pgs.).
Communication dated Sep. 23, 2009 for European Appln. No. 04 776 107.7 (3 pgs.).
Communication dated May 19, 2009 for European Application No. 06850507.2.

International Preliminary Report on Patentability dated Apr. 23, 2008 for International Application No. PCT/US2006/030545.
International Preliminary Report on Patentability dated Aug. 19, 2008 for Int'l. Appln. No. PCT/US07/003948 (6 pgs.).
International Preliminary Report on Patentability dated Aug. 19, 2008 for Int'l. Appln. No. PCT/US07/003973 (6 pgs.).
International Preliminary Report on Patentability dated Aug. 19, 2008 for Int'l. Appln. No. PCT/US07/003969 (6 pgs.).
International Preliminary Report on Patentability dated Jan. 12, 2010 for International Appln. No. PCT/US2008/069860 (5 pgs.).
International Preliminary Report on Patentability dated Mar. 4, 2010 for Int'l. Appln. No. PCT/US08/073776 (6 pgs.).
International Preliminary Report on Patentability dated Mar. 29, 2011 for Int'l. Appln. No. PCT/US2009/058669 (12 pgs.).
International Search Report and Written Opinion dated Apr. 4, 2008 for International Application No. PCT/US2006/030545.
International Search Report and Written Opinion dated Aug. 3, 2007 for Int'l. Appln. No. PCT/US07/003973 (9 pgs.).
International Search Report and Written Opinion dated Jun. 18, 2008 for Int'l. Appln. No. PCT/US07/003948 (9 pgs.).
International Search Report and Written Opinion dated Sep. 4, 2007 for Int'l. Appln. No. PCT/US07/003969 (10 pgs.).
International Search Report and Written Opinion dated Apr. 24, 2009 for Int'l. Appln. No. PCT/US08/073776 (11 pgs.).
International Search Report dated Dec. 23, 2005 for International Appln. No. PCT/US04/16452 (2 pgs.).
International Search Report and Written Opinion dated May 29, 2009 for International Appln. No. PCT/US2008/069860 (8 pgs.).
International Search Report and Written Opinion dated May 19, 2010 for International Appln. No. PCT/US2009/058669 (21 pgs.).
Office Action (non-final) dated Nov. 4, 2008 for U.S. Appl. No. 11/706,568 (7 pgs.).
Office Action (non-final) dated Jan. 6, 2009 for U.S. Appl. No. 11/706,568 (8 pgs.).
Office Action (final) dated Jul. 15, 2009 for U.S. Appl. No. 11/706,568 (7 pgs.).
Supplementary European Search Report dated May 5, 2010 for European Appln. No. EP 07750784 (8 pgs.).
Supplementary European Search Report dated Jun. 9, 2010 for European Appln. No. EP 08 78 0572 (5 pgs.).
U.S. Appl. No. 60/652,186, filed Feb. 11, 2005, entitled "Production of Foreign Nucleic Acids and Polypeptides in Sprout Systems" by Ensley, et al.
U.S. Appl. No. 11/061,980, filed Feb.18, 2005, entitled "Systems and Methods for Clonal Expression in Plants".
Air GM, "Mechanism of antigenic variation in an individual epitope on influenza virus N9 neuraminidase," *J. Virol.*, 64(12):5797-5803, 1990.
Anderson et al., "Recombinant V antigen protects mice against Pneumonic and Bubonic plague caused by F1-capsule-positive and-negative strains of *Yersinia pestis*," *Infect. Immun.*, 64(11):4580-5, 1996.
Andrews et al., "Fraction 1 capsular antigen (F1) purification from *Yersinia pestis* CO92 and from an *Escherichia coli* recombinant strain and efficacy against lethal Plague challenge," *Infect. Immun.*, 64(6):2180-7, 1996.
Aymard et al., "Neuraminidase assays," *Developments in Biologicals*, 115:75-83, 2003 (with English summary).
Aymard et al., "Role of antineuraminidase antibodies in protection against influenza," *Bulletin de l'Academie Nationale de Medicine*, 182(8):1723-1736, 1998.
Barbas et al., "Assembly of combinatorial antibody libraries on phage surfaces: The gene III site," *Proc. Natl. Acad. Sci. USA*, 88:7978, 1991.
Barbas et al., "Semisynthetic combinatorial antibody libraries: A chemical solution to the diversity problem," *Proc. Natl. Acad. Sci. USA*, 89:4457, 1992.
Berger et al., "Therapeutic applications of monoclonal antibodies," *Am. J. Med. Sci.*, 324(1):14-30, 2002.
Brodzik et al., "Advances in alfalfa mosaic virus-mediated expression of anthrax antigen in planta," *Biochem. Biophys. Res. Commun.*, 338( 2):717-722, 2005.
Burke et al., "Cloning of large segments of exogenous DNA into yeast by means of artificial chromosome vectors," *Science*, 236:806, 1987.
Chain et al., "Complete genome sequence of *Yersinia pestis* strains Antigua and Nepa1516: Evidence of gene reduction in an emerging pathogen," *J. Bacteriol.*, 188(12):4453-63, 2006.
Chichester et al., "Different response requirements for IFNγ production in ELISPOT assays by CD4+ T cells from mice early and late after submission," *J. Immunol. Methods*, 309:99-107, 2006.
Davies et al., "Affinity improvement of single antibody VH domains: residues in all three hypervariable regions affect antigen binding," *Immunotechnol.*, 2(3):169-179, 1996.
Dawson et al., "cDNA cloning of the complete genome of tobacco mosaic virus and production of infectious transcripts," *Proc. Natl Acad. Sci. USA*, 83:1832, 1986.
Deng et al., "Genome Sequence of *Yersinia pestis* KIM," *J. Bacteriol.*, 184(16):4601-11, 2002.
Floss et al., "Production of vaccines and therapeutic antibodies for veterinary applications in transgenic plants: an overview," *Transgenic Research*, 16(3):315-332, 2007.
Heath et al., "Protection against experimental bubonic and pneumonic plague by a recombinant capsular F1-V antigen fusion protein vaccine," *Vaccine*, 16(11/12):1131-7, 1998.
Holt et al., "Domain antibodies: proteins for therapy," *Trends Biotechnol.*, 21(11): 484-490, 2003.
Huber et al., "Distinct contributions of vaccine-induced immunoglobulin G1 (IgG1) and IgG2a antibodies to protective immunity against influenza," *Clin. Vaccine Immunol.*, 13:981-90, 2006.
Huse et al., "Generation of a large combinatorial library of the immunoglobulin repertoire in phage lambda," *Science*, 246:1275, 1989.
Jirholt et al., "Exploiting sequence space: shuffling in vivo formed complementarity determining regions into a master framework," *Gene*, 215:471, 1998.
Jones et al., "Replacing the complementarity—determining regions in a human antibody with those from a mouse," *Nature*, 321:522, 1986.
Kang et al., "Linkage of recognition and replication functions by assembling combinatorial antibody Fab libraries along phage surfaces," *Proc. Nati. Acad. Sci. USA*, 88:4363, 1991.
Katayama and Mine, "*Quillaja* saponin can modulate ovalbumin-induced IgE allergic responses through regulation of Th1/Th2 balance in a murine model," *J. Agric. Food Chem.*, 54:3271-6, 2006.
Konieczny et al., "The combination of IgM subunits and proteolytic IgG fragments by controlled formation of interchain disulphides," *Haematologia* (*Budap.*), 14:95, 1981.
Krebber et al., "Reliable cloning of functional antibody variable domains from hybridomas and spleen cell repertoires employing a reengineered phage display system," *J Immunol Methods*, 201:35-55, 1997.
Kubler-Kielb et al., "Long-lasting and transmission-blocking activity of antibodies to *Plasmodium falciparum* elicited in mice by protein conjugates of Pfs25," *Proc. Natl. Acad. Sci. USA*, 104(1): 293-298, 2007.
Lee and Air, "Contacts between influenza virus N9 neuraminidase and monoclonal antibody NC10," *Virol.*, 300(2):255-268, 2002.
Li et al, "Immunization with recombinant beta-tubulin from *Trypanosoma evansi* induced protection against *T. evansi, T. equiperdum* and *T. b. brucei* infection in mice," *Parasite Immunol.*, 29:191-199, 2007.
Little et al., "Of mice and men: hybridoma and recombinant antibodies," *Immunol. Today*, 21(8): 364-370, 2000.
Marillonnet et al., "Systemic *Agrobacterium tumefaciens*—mediated transfection of viral replicons for efficient transient expression in plants," *Nature Biotechnol.*, 23(6):718-723, 2005.
Mbawuike et al., "Humoral and cell-mediated immune responses of humans to inactivated influenza vaccine with or without QS21 adjuvant," *Vaccine*, 25:3263-9, 2007.
Mett et al., "Plants as biofactories," *Biologicals: J. Int. Assoc. Biolog. Stand.*, 36(6):354-358, 2008.

Morrison et al., "Chimeric human antibody molecules: Mouse antigen-binding domains with human constant region domains," *Proc. Natl. Acad. Sci. USA*, 81:6851, 1984.

Morrison et al., "Production of novel immunoglobulin molecules by gene transfection," *Mt. Sinai J. Med.*, 53:175, 1986.

Parkhill et al., "Genome sequence of *Yersinia pestis*, the causative agent of plague," *Nature*, 413:523-7, 2001.

Pfitzner et al., "Isolation and characterization of cDNA clones encoding pathogenesis-related proteins from tobacco mosaic virus infected tobacco plants," *Nucl. Acids Res.*, 15(11):4449-4465, 1987.

Pruett et al., "Critical interactions in binding antibody NC41 to influenza N9 neuraminidase: amino acid contacts on the antibody heavy chain," *Biochem.*, 37:10660-10670, 1998.

Riechmann et al., "Reshaping human antibodies for therapy," *Nature*, 332:323, 1988.

Rowe et al., "Detection of antibody to avian influenza A (H5N1) virus in human serum by using a combination of serologic assays," *J. Clin. Microbiol.*, 37:937-43, 1999.

Sabbatini et al., "Pilot study of a heptavalent vaccine-keyhole limpet hemocyanin conjugate plus QS21 in patients with epithelial ovarian, fallopian tube, or peritoneal cancer," *Clin. Cancer Res.*, 13:4170-7, 2007.

Saravolac et al "Immunoprophylactic strategies against respiratory influenza virus infection," *Vaccine*, 19:2227-2232, 2001.

Schild et al., "A single-radial-immunodiffusion technique for the assay of influenza haemagglutinin antigen—Proposals for an assay method for the haemagglutinin content of influenza vaccines," *Bull. World Health Org.*, 52:223-31, 1975.

Shimasaki et al., "Rapid diagnostics: the detection of neuraminidase activity as a technology for high-specificity targets," *Philosophical Transactions of the Royal Society of London. Series B, Biological Sciences*, 356(1416): 1925-1931, 2001.

Shoji et al, "Immunogenicity of hemagglutinin from A/Bar-headed/Goose/Qinghai/1A/05 and A/Anhui/1/05 strains of H5N1 influenza viruses produced in *Nicotiana benthamiana* plants," *Vaccine*, 27(25/26): 3467-3470, 2009.

Shoji et al., "Plant-expressed HA as a seasonal influenza vaccine candidate," *Vaccine*, 26(23):2930-2934, 2008.
Soderlind et al., "Commentary—Complementarity-determining region (CDR) implantation: a theme of recombination," *Immunotechnol.*, 4:279, 1999.
Soderlind et al., "Recombining germline-derived CDR sequences for creating diverse single framework antibody libraries," *Nature Biotechnol.*, 18:852, 2000.
Sweet et al., "Pathogenicity of influenza virus," *Microbiological Reviews*, 44(2):303-330, 1980.
Throsby et al., "Heterosubtypic neutralizing monoclonal antibodies cross-protective against H5N1 and H1N1 recovered from human IgM+ memory B cells," *Plos One*, LNKD-PUBMED:19079604, 3(12):E3942, 2008.
UniProt Database [Online] EBI Accession No. Q0PDN1, "SubName: Full=Hemagglutinin," Sep. 5, 2006.
UniProt Database [Online] EBI Accession No. A9X0E7, "SubName: Full=Hemagglutinin; Flags: Precursor," Feb. 5, 2008.
UniProt Database accession No. P04107 Nov. 1, 1986.
Webster et al., "Antigenic structure and variation in an influenza virus N9 neuraminidase," *J. Virol.*, 61:2910-2916, 1987.
Williamson et al., "Human immune response to a plague vaccine comprising recombinant F1 and V antigens," *Infect. Immun.*, 13(6):3598-608, 2005.
Williamson et al., "A single dose sub-unit vaccine protects against pneumonic plague," *Vaccine*, 19:566-71, 2000.
Williamson et al., "A new improved sub-unit vaccine for plague: the basis of protection," *FEMS Immunol. Med. Microbiol.*, 12:223-30, 1995.
Winter and Milstein, "Man-made antibodies," *Nature*, 349:293, 1991.
Yang et al., "Production and diagnostic application of monoclonal antibodies against influenza virus H5," *J. Virolog. Methods*, 162(1-2):194-202, 2009.
Yusibov et al., "An influenza N1 neuraminidase-specific monoclonal antibody with broad inactivating inactivating activity against H5N1 viruses," *Human Antibodies*, 16(1-2):33, 2007.
Yusibov et al., "An influenza N1 neuraminidase-specific monoclonal antibody protects animal against live challenge with homologous H5N1 virus," *Human Antibodies*, 17(1-2): 15, 2008.
Yusibov et al., "The potential of plant virus vectors for vaccine production," *Drugs in R & D* 7(4):203-217, 2006.
Zapata et al., "Engineering linear F(ab')2 fragments for efficient production in *Escherichia coli* and enhanced antiproliferative activity," *Prot. Eng.*, 8:1057, 1995.
Communication dated Apr. 21, 2010 for European Appln. No. 04776107.7 (4 pgs.).
Communication dated May 20, 2010 for European Appln. No. 04776107.7 (3 pgs.).
Communication dated May 19, 2009 for European Appln. No. 06850507.2 (3 pgs.).
Communication dated Feb. 18, 2010 for European Appln. No. 07750905.7 (2 pgs.).
Examiner's First Report dated Aug. 24, 2011 for Australian Appln. No. 2007215082 (3 pgs.).
International Preliminary Report on Patentability dated Apr. 23, 2008 for Int'l. Appln. No. PCT/US06/030545 (9 pgs.).
International Preliminary Report on Patentability dated Mar. 17, 2009 for Int'l. Appln. No. PCT/US07/004103 (5 pgs.).
International Preliminary Report on Patentability dated Nov. 3, 2009 for Int'l. Appln. No. PCT/US08/061782 (7 pgs.).
International Preliminary Report on Patentability dated Mar. 29, 2011 for Int'l. Appln. No. PCT/US09/058640 (7 pgs.).
International Preliminary Report on Patentability dated Mar. 29, 2011 for Int'l. Appln. No. PCT/US09/058669 (12 pgs.).
International Search Report and Written Opinion dated Apr. 4, 2008 for Int'l Appln. No. PCT/US06/030545 (3 pgs.).
International Search Report and Written Opinion dated Aug. 7, 2007 for Int'l. Appln. No. PCT/US07/004103 (9 pgs.).
International Search Report and Written Opinion dated Oct. 21, 2008 for Int'l. Appln. No. PCT/US08/061782 (10 pgs.).
International Search Report and Written Opinion dated May 29, 2009 for Int'l. Appln. No. PCT/US08/069860 (8 pgs.).
International Search Report and Written Opinion dated May 11, 2010 for Int'l Appln. No. PCT/US09/058488 (20 pgs.).
International Search Report and Written Opinion dated Feb. 2, 2010 for Int'l. Appln. No. PCT/US09/058640 (13 pgs.).
International Search Report and Written Opinion dated Jan. 27, 2011 for Int'l. Appln. No. PCT/US10/050693 (7 pgs.).
Notification of Defects in Patent Application dated Sep. 16, 2010 for Israeli Patent Appln. No. 193391 (3 pgs.).
Notification of Defects in Patent Application dated Sep. 12, 2010 for Israeli Patent Appln. No. 193390 (3 pgs.).
Office Action (restriction requirement) dated Nov. 28, 2007 for U.S. Appl. No. 11/706,573 (8 pgs.).
Office Action (non-final) dated Apr. 16, 2008 for U.S. Appl. No. 11/706,573 (11 pgs.).
Office Action (non-final) dated Jan. 21, 2009 for U.S. Appl. No. 11/706,573 (10 pgs.).
Office Action (non-final) dated Feb. 22, 2010 for U.S. Appl. No. 11/706,573 (11 pgs.).
Office Action (non-final) dated Nov. 24, 2010 for U.S. Appl. No. 11/706,573 (11 pgs.).
Supplementary European Search Report dated Dec. 5, 2006 for European Appln. No. 04776107.7 (2 pgs.).
Supplementary European Search Report dated Oct. 8, 2009 for European Appln. No. 07750950 (5 pgs.).

* cited by examiner

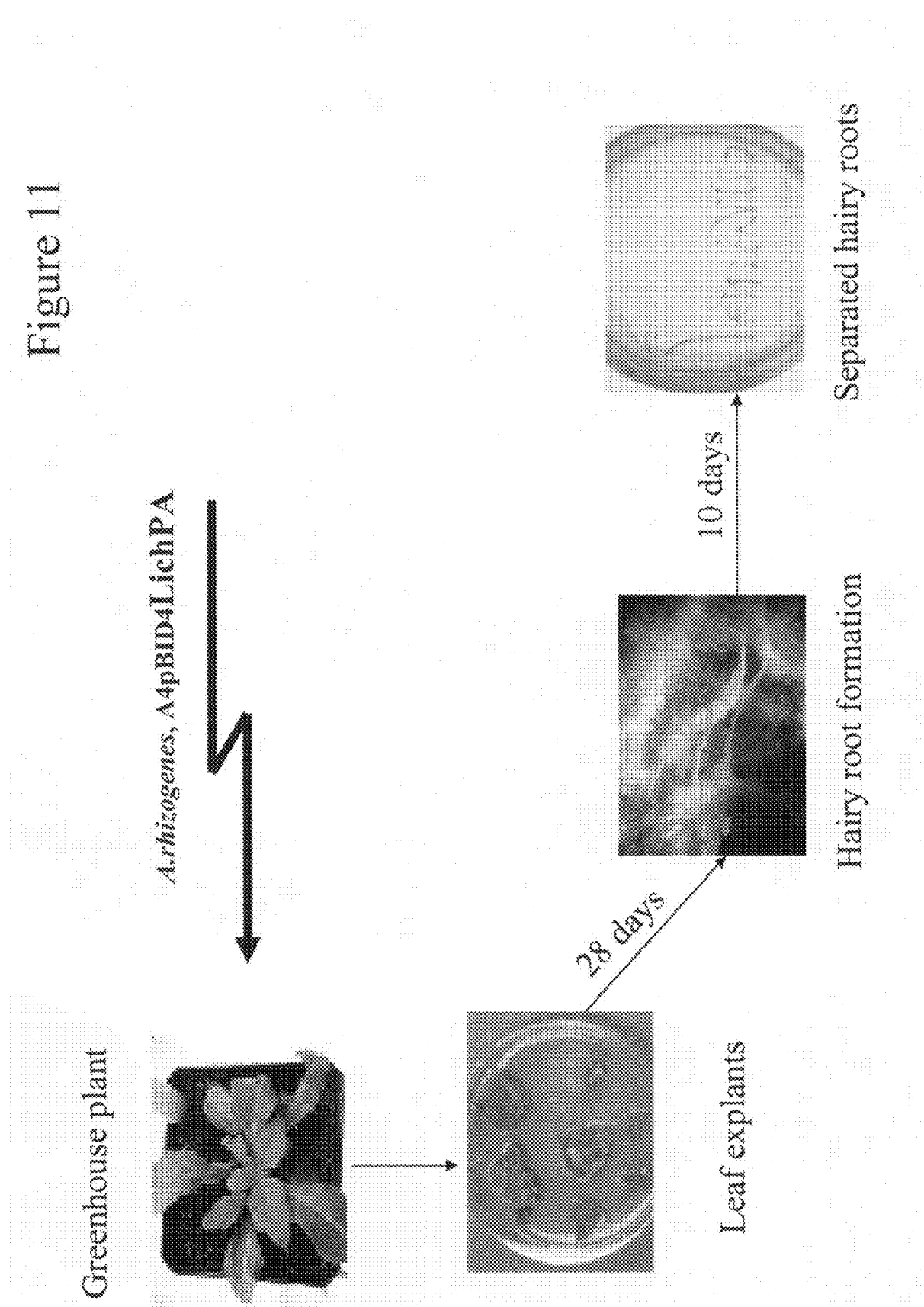

BACILLUS ANTHRACIS ANTIGENS, VACCINE COMPOSITIONS, AND RELATED METHODS

RELATED APPLICATIONS

The present application is related to and claims priority under 35 USC 119(e) to U.S. Ser. No. 60/773,255, filed Feb. 13, 2006 (the '255 application); the entire contents of the '255 application are incorporated herein by reference.

BACKGROUND OF THE INVENTION

Anthrax is a well-characterized infectious disease caused by the sporulating bacteria *Bacillus anthracis*. The disease is historically associated with animal infections, especially herbivores such as cows, sheep, and goats, and is not typically found in humans. However, humans working with animal products where infection occurs are at risk of contracting anthrax. Some regions of the Middle East and sub-Saharan Africa are hyperendemic for anthrax, though the organism can often be found in many areas of the world. The disease manifests in three different ways: cutaneous, gastrointestinal and inhalation anthrax result from exposure of an open wound to spores, ingesting spores in contaminated meat products, and inhaling spores, respectively. While cutaneous anthrax has a fatality rate of up to 25 percent, gastrointestinal or inhalation anthrax results in nearly 100 percent fatalities. Definitive diagnosis of anthrax infection often comes too late to provide resuscitative care.

The principal virulence factor of *B. anthracis* is a multicomponent toxin secreted by the organism. The toxin consists of three proteins designated protective antigen (PA), lethal factor (LF) and edema factor (EF), which are encoded by the genes pag, lef, and cya, respectively. PA is a 735 amino acid protein of molecular weight 83 kDa. It binds to the anthrax toxin receptor (ATR) on the mammalian cell surface, and subsequently undergoes a furin-mediated cleavage to yield a 63 kDa receptor-bound product. The 63 kDa PA fragment forms a heptameric complex on the cell surface which is capable of interacting with either LF or EF, and this complex is subsequently internalized. LF is a zinc metalloprotease that cleaves several isoforms of MAP kinase kinase, thereby disrupting signal transduction events within the cell, eventually leading to cell death. LF is considered responsible for the lethal outcome of anthrax infection. EF is a calmodulin-dependent adenylate cyclase that causes deregulation of cellular physiology, leading to clinical manifestations that include edema. PA and LF together are referred to as lethal toxin.

The CDC lists anthrax as a category A disease agent and estimates the cost of an anthrax attack to exceed $26 billion per 100,000 persons exposed. Presently, the only vaccine licensed for human use in the U.S., Biothrax (formerly Anthrax vaccine adsorbed, or AVA), is an aluminum hydroxide-adsorbed, formalin-treated subunit vaccine based on protective antigen, PA. It is delivered by subcutaneous injection and induces immunity against lethal toxin secreted by the *bacillus*. The vaccine is produced from the filtered culture supernatant fraction of the V770-NP1-R strain of *B. anthracis*. The production process is complex. There is variation from batch-to-batch in vaccine preparation lots, and the precise composition of the vaccine is undetermined. Furthermore, since alum is included as an adjuvant with the current vaccine, a cold chain must be maintained during vaccine storage and distribution, adding inconvenience and cost. The vaccine is administered by injection, which can complicate the logistics of mass treatments. In addition to the immunogenic protective antigen (PA), the vaccine contains trace amounts of edema factor (EF) and lethal factor (LF) that may contribute to the local reactions seen in 5-7% of vaccine recipients, or reported to be causing toxic side-effects.

Anthrax has become a serious threat due to its potential use in bioterrorism and recent outbreaks among wildlife in the United States. Concerns regarding vaccine purity, the current requirement for multiple injections followed by boosters, and a limited supply of vaccine underscore the urgent need for an improved vaccine. There is a clear need and urgency for an improved vaccine for anthrax and for improved production methods that allow for mass-production at reasonable cost.

SUMMARY OF THE INVENTION

The present invention provides anthrax vaccines and vaccine components produced in plants. The present invention provides one or more anthrax antigens generated as a fusion with a thermostable protein. Furthermore, the invention provides anthrax vaccines comprising at least two different anthrax antigens. In some embodiments, inventive vaccines include one or more plant components. Still further provided are methods for production and use of antigen and vaccine compositions of the invention.

BRIEF DESCRIPTION OF THE DRAWING

FIG. 11. Schematic representation of *Agrobacterium rhizogenes* with the engineered pBID4 vector expressing LichPA; depiction of a greenhouse *Petunia hybrida* plant; depiction of *A. rhizogenes*-mediated induction of *P. hybrida* hairy roots expressing Lich PA; depiction of separation of hairy roots.

DETAILED DESCRIPTION OF THE INVENTION

Figure 1:
FIG. 1. Schematic of viral expression vector D4.

The invention relates to anthrax antigens and fusion proteins useful in the preparation of vaccines and vaccine compositions. The invention relates to antigens useful in the preparation of vaccines against anthrax infection, and nucleic acids encoding them. For example, the invention provides plant optimized sequences encoding antigens of *Anthracis bacillus* (e.g., PA, LF, EF, or at lest one domain of PA, LF, EF). The invention further relates to vectors, fusion proteins, plant cells, plants and vaccine compositions comprising such elements (e.g., fusion of antigen with a thermostable protein) of the invention. Further, the invention relates to methods of protecting against or therapeutic treatment of anthrax infection. Still further provided are methods of antigen production in plants Anthrax Antigens Anthrax antigen proteins useful in accordance with the present invention include any immunogenic antigen protein or peptide, capable of eliciting an immune response against anthrax. Generally, immunogenic proteins of interest include antigens naturally produced by *A. bacillus* immunogenic portion(s) thereof, immunogenic variant(s) thereof, fusion proteins including any of the aforementioned, or combinations thereof.

The invention provides plant cells and plants expressing a heterologous protein (e.g., anthrax antigen). The principal virulence factor of *B. anthracis* is a multi-component toxin, lethal toxin (LeTx), comprising protective antigen (PA) and lethal factor (LF). However, a heterologous protein of the invention can be any anthrax antigen of interest, including, but not limited to protective antigen (PA), lethal factor (LF) and edema factor (EF), a portion of protective antigen (PA), a portion of lethal factor (LF) and a portion of edema factor (EF). Recombinant PA or portions of it have been shown to provide protective immunity in animal models (Singh, et al., 1998, *Infect. Immun.*, 66, 3447; Nass, 1999, *Infect. Dis. Clin.*

*North Am.*, 13:187). Polyclonal sera against PA protect guinea pigs infected with *B. anthracis* spores, and monoclonal antibodies to PA cause delays in time of death. Monoclonal antibodies specific for domain four of PA provide protection to animals after infection with anthrax spores. (Little et al., 1997, *Infect. Immun.*, 65:5171).

PA is composed of four domains (Petosa et al., 1997, *Nature*, 385:833). Domain 1 comprises the first 258 amino acids and contains two calcium ions and the cleavage site for activating proteases. Domain 2 comprises a large flexible loop which is thought to play a role in membrane insertion, while the function of domain 3 is as yet unknown. Domain 4 is the carboxy-terminal receptor binding domain responsible for binding the toxin to the target cell surface and is also the immunodominant region of the protein. Animal studies with vaccine and preformed antibodies have shown that domain 4 alone confers protection against anthrax (Flick-Smith et al., 2002, *Infect. Immun.*, 70:1653). Recent reports indicate a human monoclonal antibody with specificity for domain 4 can protect mice against a lethal anthrax challenge, suggesting that domain 4 is equally protective in humans (Hull et al., 2005, *Vaccine*, 23:2082).

The full length protective antigen (PA) sequence is known in the art and can be found in reference to GenBank accession no. P13423. Variations on PA sequences may be utilized according to the methods and compositions provided herein and one skilled in the art may, from time to time reference updated PA sequences known in the art. Exemplary full length amino acid sequence for PA, is shown (SEQ ID NO.: 1):

(MKKRKVLIPLMALSTILVSSTGNLEVIQA)EVKQENRLLNESESSSQGL

LGYYFSDLNFQAPMVVTSSTTGDLSIPSSELENIPSENQYFQSAIWSGFI

KVKKSDEYTFATSADNHVTMWVDDQEVINKASNSNKIRLEKGRLYQIKIQ

YQRENPTEKGLDFKLYWTDSQNKKEVISSDNLQLPELKQKSSNSRKKRST

SAGPTVPDRDNDGIPDSLEVEGYTVDVKNKRTFLSPWISNIHEKKGLTKY

KSSPEKWSTASDPYSDFEKVTGRIDKNVSPEARHPLVAAYPIVHVDMENI

ILSKNEDQSTQNTDSETRTISKNTSTSRTHTSEVHGNAEVHASFFDIGGS

VSAGFSNSNSSTVAIDHSLSLAGERTWAETMGLNTADTARLNANIRYVNT

GTAPIYNVLPTTSLVLGKNQTLATIKAKENQLSQILAPNNYYPSKNLAPI

ALNAQDDFSSTPITMNYNQFLELEKTKQLRLDTDQVYGNIATYNFENGRV

RVDTGSNWSEVLPQIQETTARIIFNGKDLNLVERRIAAVNPSDPLETTKP

DMTLKEALKIAFGFNEPNGNLQYQGKDITEFDFNFDQQTSQNIKNQLAEL

NATNIYTVLDKIKLNAKMNILIRDKRFHYDRNNIAVGADESVVKEAHREV

INSSTEGLLLNIDKDIRKILSGYIVEIEDTEGLKEVINDRYDMLNISSLR

QDGKTFIDFKKYNDKLPLYISNPNYKVNVYAVTKENTIINPSENGDTSTN

GIKKILIFSKKGYEIG

The signal peptide is in parentheses in the beginning, is removed to produce mature protective antigen amino acid sequence. Structural domains of PA are approximately located at the following amino acid positions, designated amino acids are from the mature polypeptide sequence.
Domain 1: 1-250
Domain 2: 251-456
Domain 3: 477-595
Domain 4: 608-735

In certain embodiments, full length PA is utilized in antigens of the invention. In some embodiments, a domain of PA (e.g., domain 1, domain 2, domain 3, domain 4) is used. In certain embodiments two or three domains are provided in antigens of the invention, either separately, or in the context of a single polypeptide or fusion protein. Certain exemplary embodiments described herein provide anthrax antigen comprising domain 4 of PA.

In addition to or as an alternative to protective antigen, other *Anthracis bacillus* proteins may be used for production of antigen(s) and/or vaccine(s) as provided herein. For example, use of antigen comprising lethal factor (LF) or a domain thereof or edema factor (EF) or a domain thereof is provided.

Lethal factor (LF) sequence is known in the art and can be found in reference to GenBank accession no. P15917. Variations on LF sequences may be utilized according to the methods and compositions provided herein and one skilled in the art may, from time to time reference updated LF sequences known in the art. Exemplary full length LF sequence is shown (SEQ ID NO.: 2):

(MNIKKEFIKVISMSCLVTAITLSGPVFIPLVQG)AGGHGDVGMHVKEKE

KNKDENKRKDEERNKTQEEHLKEIMKHIVKIEVKGEEAVKKEAAEKLLEK

VPSDVLEMYKAIGGKIYIVDGDITKHISLEALSEDKKKIKDIYGKDALLH

EHYVYAKEGYEPVLVIQSSEDYVENTEKALNVYYEIGKILSRDILSKINQ

PYQKFLDVLNTIKNASDSDGQDLLFTNQLKEHPTDFSVEFLEQNSNEVQE

VFAKAFAYYIEPQHRDVLQLYAPEAFNYMDKFNEQEINLSLEELKDQRML

ARYEKWEKIKQHYQHWSDSLSEEGRGLLKKLQIPIEPKKDDIIHSLSQEE

KELLKRIQIDSSDFLSTEEKEFLKKLQIDIRDSLSEEEKELLNRIQVDSS

NPLSEKEKEFLKKLKLDIQPYDINQRLQDTGGLIDSPSINLDVRKQYKRD

IQNIDALLHQSIGSTLYNKIYLYENMNINNLTATLGADLVDSTDNTKINR

GIFNEFKKNFKYSISSNYMIVDINERPALDNERLKWRIQLSPDTRAGYLE

NGKLILQRNIGLEIKDVQIIKQSEKEYIRIDAKVVPKSKIDTKIQEAQLN

INQEWNKALGLPKYTKLITFNVHNRYASNIVESAYLILNEWKNNIQSDLI

KKVTNYLVDGNGRFVFTDITLPNIAEQYTHQDEIYEQVHSKGLYVPESRS

ILLHGPSKGVELRNDSEGFIHEFGHAVDDYAGYLLDKNQSDLVTNSKKFI

DIFKEEGSNLTSYGRTNEAEFFAEAFRLMHSTDHAERLKVQKNAPKTFQF

INDQIKFIINS

The signal peptide is in parentheses in the beginning, and is removed from mature protective antigen amino acid sequence. Structural domains of LF are approximately located at the following amino acid positions, designated residues are the residues according to mature polypeptide sequence.

Domain 1: 1-137 and 251-263
Domain 2: 138-250
Domain 3: 264-283 and 429-551
Domain 4: 306-385
Domain 5: 552-776

In certain embodiments, full length LF is utilized in antigens of the invention. In some embodiments, a domain of LF (e.g., domain 1, domain 2, domain 3, domain 4, domain 5) is used. In certain embodiments two or three domains are provided in antigens of the invention, either separately or in the context of a single polypeptide or fusion protein. Certain exemplary embodiments described herein provide anthrax antigen comprising the N-terminal domain of LF.

Edema factor (EF) sequence is known in the art and can be found in reference to GenBank accession no. 052818.1. Variations on EF sequences may be utilized according to the methods and compositions provided herein and one skilled in the art may, from time to time reference updated EF sequences known in the art. Exemplary full EF is shown (SEQ ID NO.: 15):

MTRNKFIPNKFSIISFSVLLFAISSSQAIEVNAMNEHYTESDIKRNHKTE

KNKTEKEKFKDSINNLVKTEFTNETLDKIQQTQDLLKKIPKDVLEIYSEL

GGEIYFTDIDLVEHKELQDLSEEEKNSMNSRGEKVPFASRFVFEKKRETP

KLIINIKDYAINSEQSKEVYYEIGKGISLDIISKDKSLDPEFLNLIKSLS

DDSDSSDLLFSQKFKEKLELNNKSIDINFIKENLTEFQHAFSLAFSYYFA

PDHRTVLELYAPDMFEYMNKLEKGGFEKISESLKKEGVEKDRIDVLKGEK

ALKASGLVPEHADAFKKIARELNTYILFRPVNKLATNLIKSGVATKGLNV

HGKSSDWGPVAGYIPFDQDLSKKHGQQLAVEKGNLENKKSITEHEGEIGK

IPLKLDHLRIEELKENGIILKGKKEIDNGKKYYLLESNNQVYEFRISDEN

NEVQYKTKEGKITVLGEKFNWRNIEVMAKNVEGVLKPLTADYDLFALAPS

LTEIKKQIPQKEWDKVVNTPNSLEKQKGVTNLLIKYGIERKPDSTKGTLS

NWQKQMLDRLNEAVKYTGYTGGDVVNHGTEQDNEEFPEKDNEIFIINPEG

EFILTKNWEMTGRFIEKNITGKDYLYYFNRSYNKIAPGNKAYIEWTDPIT

KAKINTIPTSAEFIKNLSSIRRSSNVGVYKDSGDKDEFAKKESVKKIAGY

LSDYYNSANHIFSQEKKRKISIFRGIQAYNEIENVLKSKQIAPEYKNYFQ

YLKERITNQVQLLLTHQKSNIEFKLLYKQLNFTENETDNFEVFQKIIDE

K.

While the domains depicted for each of PA, and LF are approximate demarcations for protein domains, it will be appreciated that any sequence having immunogenic characteristics of a domain may alternatively be employed. One skilled in the art will readily be capable of generating sequences having at least 75%, 80%, 85%, or 90% or more identity to provided antigens. In certain embodiments, antigen sequences anthrax antigens comprise proteins include those having at least 95%, 96%, 97%, 98%, or more identity to sequences, or a portion thereof, wherein the antigen protein retains immunogenic activity. For example sequences having sufficient identity to anthrax antigen(s) which retain immunogenic characteristics are capable of binding with antibodies which react with domains (antigen(s)) provided herein. Immunogenic characteristics often include three dimensional presentations of relevant amino acids or side groups. One skilled in the art can readily identify sequences with modest differences in sequence (e.g., with difference in boundaries and/or some sequence alternatives, that, nonetheless preserve immunogenic characteristics). For instance, sequences whose boundaries are near to (e.g., within about 15 amino acids, 14 amino acids, 13 amino acids, 12 amino acids, 11 amino acids, 10 amino acids, 9 amino acids, 8 amino acids, 7 amino acids 6 amino acids, 5 amino acids 4 amino acids, 3 amino acids, 2 amino acids, or 1 amino acid) of the domain boundaries designated herein at either end of a designated amino acid sequence may be considered to comprise a relevant domain in accordance with the present invention. Thus, the invention contemplates use of a sequence of anthrax antigen to comprise residues approximating the domain designation. For example, domain four of PA (amino acids 617 to 764) has been engineered and expressed as an in-frame fusion protein as an antigen of the invention. See Examples herein. Further, one will appreciate that any domains, partial domains or regions of amino acid sequence of anthrax antigen (e.g., PA, LF, EF) which are immunogenic can be generated using constructs and methods provided herein. Still further, domains or subdomains can be combined, separately and/or consecutively for production of anthrax antigens.

Antigen Fusions with Thermostable Proteins

In certain aspects of the invention, provided are fusion polypeptides which comprise an anthrax antigen (or a fragment or variant thereof) operably linked to a thermostable protein. Inventive fusion polypeptides can be produced in any available expression system known in the art. In certain embodiments, inventive fusion proteins are produced in a plant or portion thereof (e.g., plant, plant cell, root, sprout, etc.).

Enzymes or other proteins which are not found naturally in humans or animal cells are particularly appropriate for use in fusion polypeptides of the present invention. Thermostable proteins that, when fused, confer thermostability to the fusion product are useful. Thermostability allows produced protein to maintain conformation, and maintain produced protein at room temperature. This feature facilitates easy, time efficient and cost effective recovery of fusion polypeptide. A representative family of thermostable enzymes useful in accordance with the invention is the glucanohydrolase family. These enzymes specifically cleave 1,4-β glucosidic bonds that are adjacent to 1,3-β linkages in mixed linked polysaccharides (Hahn et al., 1994, *Proc. Natl. Acad. Sci., USA*, 91:10417). The enzymes are found in cereals, such as oat and barley, and are also found in a number of fungal and bacterial species, including *C. thermocellum* (Goldenkova et al., 2002, *Mol. Biol.*, 36:698). Thus, desirable thermostable proteins for use in fusion polypeptides of the present invention include glycosidase enzymes; exemplary thermostable glycosidase proteins include those represented by GenBank accession numbers selected from: P29716, P37073, P45798, P38645; P40942; P14002; O33830, O43097, P54583, P14288, O52629, P29094, P49067, JC7532, Q60037, P33558, P05117, P04954, Q4J929, O33833, P49425, P06279, P45703, P45702, P40943, P09961, Q60042, AAN05438, AAN05437, AAN05440, AAN05439, and AAD43138, each of which are incorporated herein by reference. Exemplary lichenase enzymes of use in fusion proteins of the invention include *Clostridium thermocellum* P29716, *Brevibacillus brevis* P37073, and *Rhodthermus marinus* P45798, each of which is incorporated herein by reference to their GenBank accession numbers. Representative fusion proteins illustrated in the Examples utilize modified lichenase isolated from *Clostridium thermocellum*; however, any thermostable protein may be similarly utilized in accordance with the present invention.

When designing fusion proteins and polypeptides in accordance with the invention, it is desirable, of course, to preserve immunogenicity of an antigen. Still further, it is desirable in certain aspects of the invention to provide constructs which provide thermostability of a fusion protein. This feature facilitates easy, time efficient and cost effective recovery of a target antigen. In certain aspects, antigen fusion partners may be selected which provide additional advantages, including enhancement of immunogenicity, potential to incorporate multiple vaccine determinants, yet lack prior immunogenic exposure to vaccination subjects. Further beneficial qualities of fusion peptides of interest include proteins which provide ease of manipulation for incorporation of one or more antigens, as well as proteins which have potential to confer ease of production, purification, and/or formulation for vaccine preparations. One of ordinary skill in the art will appreciate that three dimensional presentation can affect each of these beneficial characteristics. Preservation of immunity or preferential qualities therefore may affect, for example, choice of fusion partner and/or choice of fusion location (e.g., N-terminus, C-terminus, internal, combinations thereof). Alternatively or additionally, preferences may affects length of segment selected for fusion, whether it is length of the antigen, or length of the fusion partner selected.

The present inventors have demonstrated successful fusion of a variety of antigens with a thermostable protein. For example example, we have used the thermostable carrier molecule LicB, also referred to as a lichenase. LicB is 1,3-1,4-β glucanase (LicB) from *Clostridium thermocellum* (GenBank accession: X63355. *C. thermocellum* li . . . [gi:40697]) for production of fusion proteins. LicB belongs to a family of globular proteins. Based on the three dimensional structure of LicB its N- and C-termini are situated close to each other on the surface, in close proximity to the active domain. LicB also has a loop structure exposed on the surface that is located far from the active domain. We have generated constructs such that the loop structure and N- and C-termini of protein can be used as insertion sites for target antigen polypeptides. Target antigen peptides can be expressed as N- or C-terminal fusions or as inserts into the surface loop. Importantly, LicB maintains its enzymatic activity at low pH and at high temperature (up to 75° C.). Thus, use of LicB as a carrier molecule contributes advantages, including likely enhancement of target specific immunogenicity, potential to incorporate multiple vaccine determinants, and straightforward formulation of vaccines that may be delivered nasally, orally or parenterally. Furthermore, production of LicB fusions in plants should reduce risk of contamination with animal or human pathogens. See examples provided herein.

Fusion proteins of the invention comprising anthrax antigen may be produced in any of a variety of expression systems, including both in vitro and in vivo systems. One skilled in the art will readily appreciate that optimization of nucleic acid sequences for a particular expression system is often desirable. For example, in the exemplification provided herein, optimized sequence for expression of anthrax antigen-LicB fusions in plants is provided. See Example 1. Thus, any relevant nucleic acid encoding antigen(s) fusion protein(s) and fragments thereof in accordance with the invention is intended to be encompassed with nucleic acid constructs of the invention.

For production in plant systems, transgenic plants expressing antigen(s) or fragments or fusions thereof may be utilized. Alternatively or additionally, transgenic plants may be produced using methods well known in the art to generate stable production crops. When utilizing plant expression systems, any of nuclear expression, chloroplast expression, mitochondrial expression, or viral expression may be taken advantage of according to the applicability of the system to the antigen desired. Furthermore, additional expression systems for production of antigens and fusion proteins in accordance with the present invention may be utilized. For example, mammalian expression systems (e.g., mammalian cell lines (e.g., CHO, etc.)), bacterial expression systems (e.g., *E. coli*), yeast expression systems, and in vitro expression systems (e.g., reticulate lysates) may be used for expression of antigens and fusion proteins of the invention.

Production of Anthrax Antigens

In accordance with the present invention, anthrax antigens (including fragments, variants, and/or fusions) may be produced in any desirable system; production is not limited to plant systems. Vector constructs and expression systems are well known in the art and may be adapted to incorporate use of anthrax antigens provided herein. For example, anthrax antigens (including fragments, variants, and/or fusions) can be produced in known expression systems, including mammalian cell systems, transgenic animals, microbial expression systems, and plant systems, including transgenic and transient plant systems. Particularly where anthrax antigens are produced as fusion proteins, it may be desirable to produce such fusion proteins in non-plant systems.

In some embodiments of the invention, anthrax antigens are desirably produced in plant systems. Plants are relatively easy to manipulate genetically, and have several advantages over alternative sources such as human fluids, animal cell lines, recombinant microorganisms and transgenic animals. Plants have sophisticated post-translational modification machinery for proteins that is similar to that of mammals (although it should be noted that there are some differences in glycosylation patterns between plants and mammals). This enables production of bioactive reagents in plant tissues. Plants can economically produce very large amounts of biomass without requiring sophisticated facilities. Moreover, plants are not subject to contamination with animal pathogens. Like liposomes and microcapsules, plant cells are expected to provide protection for passage of antigen to the gastrointestinal tract.

Plants may be utilized for production of heterologous proteins via use of various production systems. One such system includes use of transgenic/genetically-modified plants where the gene encoding a target product is permanently incorporated into the genome of the plant. Transgenic systems may generate crop production systems. A variety of foreign proteins, including many of mammalian origin and many vaccine candidate antigens, have been expressed in transgenic plants and shown to have functional activity (Tacket et al., 2000, *J. Infect. Dis.*, 182:302; and Thanavala et al., 2005, *Proc. Natl. Acad. Sci., USA*, 102:3378). Additionally, administration of unprocessed transgenic plants expressing hepatitis B major surface antigen to non-immunized human volunteers resulted in production of immune response (Kapusta et al., 1999, *FASEB J.* 13:1796).

One system for expressing polypeptides in plants utilizes plant viral vectors engineered to express foreign sequences (e.g., transient expression). This latter approach allows for use of healthy non-transgenic plants as rapid production systems. Thus, genetically engineered plants and plants infected with recombinant plant viruses can serve as "green factories" to rapidly generate and produce specific proteins of interest. Plant viruses have certain advantages that make them attractive as expression vectors for foreign protein production. Several members of plant RNA viruses have been well characterized, and infectious cDNA clones are available to facilitate genetic manipulation. Once infectious viral genetic material enters a susceptible host cell, it replicates to high levels and spreads rapidly throughout an entire plant. There are several approaches to producing target polypeptides using plant viral expression vectors, including incorporation of target polypeptides into viral genomes. One approach involves engineering coat proteins of viruses that infect bacteria, animals or plants to function as carrier molecules for antigenic peptides. Such carrier proteins have the potential to assemble and form recombinant virus-like particles displaying a desired antigenic epitopes on their surface. This approach allows for time-efficient production of vaccine candidates, since the particulate nature of a vaccine candidate facilitates easy and cost-effective recovery from plant tissue. Additional advantages include enhanced target-specific immunogenicity, potential to incorporate multiple vaccine determinants, and ease of formulation into vaccines that can be delivered nasally, orally or parenterally. As an example, spinach leaves containing recombinant plant viral particles carrying epitopes of virus fused to coat protein have generated immune response upon administration (Modelska et al., 1998, *Proc. Natl. Acad. Sci., USA*, 95:2481; and Yusibov et al., 2002, *Vaccine*, 19/20:3155).

Plant Expression Systems

Any plant susceptible to incorporation and/or maintenance of heterologous nucleic acid and capable of producing heterologous protein may be utilized in accordance with the present invention. In general, it will often be desirable to utilize plants that are amenable to growth under defined conditions, for example in a greenhouse and/or in aqueous systems. It may be desirable to select plants that are not typically consumed by human beings or domesticated animals and/or are not typically part of the human food chain, so that they may be grown outside without concern that an expressed polynucleotide may be undesirably ingested. In some embodiments, however, it will be desirable to employ edible plants. In particular embodiments, it will be desirable to utilize plants that accumulate expressed polypeptides in edible portions of a plant.

Often, certain desirable plant characteristics will be determined by the particular polynucleotide to be expressed. To give but a few examples, when a polynucleotide encodes a protein to be produced in high yield (as will often be the case, for example, when antigen proteins are to be expressed), it will often be desirable to select plants with relatively high biomass (e.g., tobacco, which has additional advantages that it is highly susceptible to viral infection, has a short growth period, and is not in the human food chain). Where a polynucleotide encodes antigen protein whose full activity requires (or is inhibited by) a particular post-translational modification, the ability (or inability) of certain plant species to accomplish the relevant modification (e.g., a particular glycosylation) may direct selection. For example, plants are capable of accomplishing certain post-translational modifications (e.g., glycosylation); however, plants will not generate sialation patterns which are found in mammalian post-translational modification. Thus, plant production of antigen may result in production of a different entity than the identical protein sequence produced in alternative systems.

In certain embodiments of the invention, crop plants, or crop-related plants are utilized. In certain specific embodiments, edible plants are utilized.

Plants for use in accordance with the present invention include Angiosperms, Bryophytes (e.g., Hepaticae, Musci, etc.), Pteridophytes (e.g., ferns, horsetails, lycopods), Gymnosperms (e.g., conifers, cycase, Ginko, Gnetales), and Algae (e.g., Chlorophyceae, Phaeophyceae, Rhodophyceae, Myxophyceae, Xanthophyceae, and Euglenophyceae). Exemplary plants are members of the family Leguminosae (Fabaceae; e.g., pea, alfalfa, soybean); Gramineae (Poaceae; e.g., corn, wheat, rice); Solanaceae, particularly of the genus *Lycopersicon* (e.g., tomato), *Solanum* (e.g., potato, eggplant), *Capsium* (e.g., pepper), or *Nicotiana* (e.g., tobacco); Umbelliferae, particularly of the genus *Daucus* (e.g., carrot), *Apium* (e.g., celery), or *Rutaceae* (e.g., oranges); Compositae, particularly of the genus *Lactuca* (e.g., lettuce); Brassicaceae (Cruciferae), particularly of the genus *Brassica* or *Sinapis*. In certain aspects, plants of the invention may be plants of the

*Brassica* or *Arabidopsis* genus. Some exemplary Brassicaceae family members include *Brassica campestris, B. carinata, B. juncea, B. napus, B. nigra, B. oleraceae, B. tournifortii, Sinapis alba,* and *Raphanus sativus*. Some suitable plants that are amendable to transformation and are edible as sprouted seedlings include alfalfa, mung bean, radish, wheat, mustard, spinach, carrot, beet, onion, garlic, celery, rhubarb, a leafy plant such as cabbage or lettuce, watercress or cress, herbs such as parsley, mint, or clovers, cauliflower, broccoli, soybean, lentils, edible flowers such as sunflower etc.

Introducing Vectors into Plants

In general, vectors may be delivered to plants according to known techniques. For example, vectors themselves may be directly applied to plants (e.g., via abrasive inoculations, mechanized spray inoculations, vacuum infiltration, particle bombardment, or electroporation). Alternatively or additionally, virions may be prepared (e.g., from already infected plants), and may be applied to other plants according to known techniques.

A wide variety of viruses are known that infect various plant species, and can be employed for polynucleotide expression according to the present invention (see, for example, *The Classification and Nomenclature of Viruses*, "Sixth Report of the International Committee on Taxonomy of Viruses," (Ed. Murphy et al.), Springer Verlag: New York, N.Y., 1995, the entire contents of which are incorporated herein by reference; Grierson et al., *Plant Molecular Biology*, Blackie, London, pp. 126-146, 1984; Gluzman et al., *Communications in Molecular Biology: Viral Vectors*, Cold Spring Harbor Laboratory, Cold Spring Harbor, N.Y., pp. 172-189, 1988; and Mathew, *Plant Viruses Online*, http://image.fs.uidaho.edu/vide/). In certain embodiments of the invention rather than delivering a single viral vector to a plant cell, multiple different vectors are delivered which, together, allow for replication (and, optionally cell-to-cell and/or long distance movement) of viral vector(s). Some or all of proteins may be encoded by the genome of transgenic plants. In certain aspect, describe in further detail herein, these systems include one or more viral vector components.

Vector systems that include components of two heterologous plant viruses in order to achieve a system that readily infects a wide range of plant types and yet poses little or no risk of infectious spread. An exemplary system has been described previously (see, e.g., PCT Publication WO 00/25574 and U.S. Patent Publication 2005/0026291, which is incorporated herein by reference). As noted herein, in particular aspects of the present invention, viral vectors are applied to plants (e.g., plant, portion of plant, sprout, etc.), for example, through infiltration or mechanical inoculation, spray, etc.). Where infection is to be accomplished by direct application of a viral genome to a plant, any available technique may be used to prepare the genome. For example, many viruses that are usefully employed in accordance with the present invention have ssRNA genomes. ssRNA may be prepared by transcription of a DNA copy of the genome, or by replication of an RNA copy, either in vivo or in vitro. Given the readily availability of easy-to-use in vitro transcription systems (e.g., SP6, T7, reticulocyte lysate, etc.), and also the convenience of maintaining a DNA copy of an RNA vector, it is expected that inventive ssRNA vectors will often be prepared by in vitro transcription, particularly with T7 or SP6 polymerase.

In certain embodiments of the invention rather than introducing a single viral vector type into a plant, multiple different viral vectors are introduced. Such vectors may, for example, trans-complement each other with respect to functions such as replication, cell-to-cell movement, and/or long distance movement. Vectors may contain different polynucleotides encoding antigen of the invention. Selection for plant(s) or portions thereof that express multiple polypeptides encoding one or more anthrax antigen(s) may be performed as described above for single polynucleotides or polypeptides.

Plant Tissue Expression Systems

As discussed above, in accordance with the present invention, anthrax antigens may be produced in any desirable system. Vector constructs and expression systems are well known in the art and may be adapted to incorporate use of anthrax antigens provided herein. For example, transgenic plant production is known and generation of constructs and plant production may be adapted according to known techniques in the art. In some embodiments, transient expression systems in plants are desired. Two of these systems include production of clonal roots and clonal plant systems, and derivatives thereof, as well as production of sprouted seedlings systems.

Clonal Roots

Clonal roots maintain RNA viral expression vectors and stably produce target protein uniformly in an entire root over extended periods of time and multiple subcultures. In contrast to plants, where a target gene is eliminated via recombination during cell-to-cell or long distance movement, in root cultures integrity of a viral vector is maintained and levels of target protein produced over time are similar to those observed during initial screening. Clonal roots allow for ease of production of material for oral formulation of antigen and vaccine compositions. Methods and reagents for generating a variety of clonal entities derived from plants which are useful for production of antigen (e.g., antigen proteins of the invention) have been described previously and are known in the art (see, for example, PCT Publication WO05/81905, which is incorporated herein by reference). Clonal entities include clonal root lines, clonal root cell lines, clonal plant cell lines, and clonal plants capable of production of antigen (e.g., antigen proteins of the invention). The invention further provides methods and reagents for expression of antigen polynucleotide and polypeptide products in clonal cell lines derived from various plant tissues (e.g., roots, leaves), and in whole plants derived from single cells (clonal plants). Such methods are typically based on the use of plant viral vectors of various types.

For example, in one aspect, the invention provides methods of obtaining a clonal root line that expresses a polynucleotide encoding antigen of the invention comprising steps of: (i) introducing a viral vector that comprises a polynucleotide encoding antigen of the invention into a plant or portion thereof; and (ii) generating one or more clonal root lines from a plant. Clonal root lines may be generated, for example, by infecting a plant or plant portion (e.g., a harvested piece of leaf) with an *Agrobacterium* (e.g., *A. rhizogenes*) that causes formation of hairy roots. Clonal root lines can be screened in various ways to identify lines that maintain virus, lines that express a polynucleotide encoding antigen of the invention at high levels, etc. The invention further provides clonal root lines, e.g., clonal root lines produced according to the inventive methods, and further encompasses methods of expressing polynucleotides and producing polypeptides encoding antigen of the invention using clonal root lines.

The invention further provides methods of generating a clonal root cell line that expresses a polynucleotide encoding antigen of the invention comprising steps of: (i) generating a clonal root line, cells of which contain a viral vector whose genome comprises a polynucleotide encoding antigen of the invention; (ii) releasing individual cells from a clonal root line; and (iii) maintaining cells under conditions suitable for root cell proliferation. The invention provides clonal root cell lines and methods of expressing polynucleotides and producing polypeptides using clonal root cell lines.

In one aspect, the invention provides methods of generating a clonal plant cell line that expresses a polynucleotide encoding antigen of the invention comprising steps of: (i) generating a clonal root line, cells of which contain a viral vector whose genome comprises a polynucleotide encoding antigen of the invention; (ii) releasing individual cells from a clonal root line; and (iii) maintaining cells in culture under conditions appropriate for plant cell proliferation. The invention further provides methods of generating a clonal plant cell line that expresses a polynucleotide encoding antigen of the invention comprising steps of: (i) introducing a viral vector that comprises a polynucleotide encoding antigen of the invention into cells of a plant cell line maintained in culture; and (ii) enriching for cells that contain a viral vector. Enrichment may be performed, for example, by (i) removing a portion of cells from the culture; (ii) diluting removed cells so as to reduce cell concentration; (iii) allowing diluted cells to proliferate; and (iv) screening for cells that contain the viral vector. Clonal plant cell lines may be used for production of an anthrax antigen in accordance with the present invention.

The invention includes a number of methods for generating clonal plants, cells of which contain a viral vector that comprises a polynucleotide encoding antigen of the invention. For example, the invention provides methods of generating a clonal plant that expresses a polynucleotide encoding antigen of the invention comprising steps of: (i) generating a clonal root line, cells of which contain a viral vector whose genome comprises a polynucleotide encoding antigen of the invention; (ii) releasing individual cells from a clonal root line; and (iii) maintaining released cells under conditions appropriate for formation of a plant. The invention further provides methods of generating a clonal plant that expresses a polynucleotide encoding antigen of the invention comprising steps of: (i) generating a clonal plant cell line, cells of which contain a viral vector whose genome comprises a polynucleotide encoding antigen of the invention; and (ii) maintaining cells under conditions appropriate for formation of a plant. In general, clonal plants according to the invention can express any polynucleotide encoding antigen of the invention. Such clonal plants can be used for production of an antigen polypeptide.

As noted above, the present invention provides systems for expressing a polynucleotide or polynucleotides encoding antigen of the invention in clonal root lines, clonal root cell lines, clonal plant cell lines (e.g., cell lines derived from leaf, stem, etc.), and in clonal plants. A polynucleotide encoding antigen of the invention is introduced into an ancestral plant cell using a plant viral vector whose genome includes the polynucleotide encoding antigen of the invention operably linked to (i.e., under control of) a promoter. A clonal root line or clonal plant cell line is established from the cell containing virus according to any of several techniques further described below. A plant virus vector or portions thereof can be introduced into a plant cell by infection, by inoculation with a viral transcript or infectious cDNA clone, by electroporation, by T-DNA mediated gene transfer, etc.

The following sections describe methods for generating clonal root lines, clonal root cell lines, clonal plant cell lines, and clonal plants that express a polynucleotide encoding antigen of the invention are then described. A "root line" is distinguished from a "root cell line" in that a root line produces actual root-like structures or roots while a root cell line consists of root cells that do not form root-like structures. Use of the term "line" is intended to indicate that cells of the line can proliferate and pass genetic information on to progeny cells. Cells of a cell line typically proliferate in culture without being part of an organized structure such as those found in an intact plant. Use of the term "root line" is intended to indicate that cells in the root structure can proliferate without being part of a complete plant. It is noted that the term "plant cell" encompasses root cells. However, to distinguish the inventive methods for generating root lines and root cell lines from those used to directly generate plant cell lines from non-root tissue (as opposed to generating clonal plant cell lines from clonal root lines or clonal plants derived from clonal root lines), the terms "plant cell" and "plant cell line" as used herein generally refer to cells and cell lines that consist of non-root plant tissue. Plant cells can be, for example, leaf, stem, shoot, flower part, etc. It is noted that seeds can be derived from clonal plants generated as derived herein. Such seeds will contain the viral vector as will plants obtained from such seeds. Methods for obtaining seed stocks are well known in the art (see, e.g., U.S. Patent Publication 2004/0093643).

Clonal Root Lines

The present invention provides systems for generating a clonal root line in which a plant viral vector is used to direct expression of a polynucleotide encoding antigen of the invention. One or more viral expression vector(s) including a polynucleotide encoding antigen of the invention operably linked to a promoter is introduced into a plant or a portion thereof according to any of a variety of known methods. For example, plant leaves can be inoculated with viral transcripts. Vectors themselves may be directly applied to plants (e.g., via abrasive inoculations, mechanized spray inoculations, vacuum infiltration, particle bombardment, or electroporation). Alternatively or additionally, virions may be prepared (e.g., from already infected plants), and may be applied to other plants according to known techniques.

Where infection is to be accomplished by direct application of a viral genome to a plant, any available technique may be used to prepare the genome. For example, many viruses that are usefully employed in accordance with the present invention have ssRNA genomes. ssRNA may be prepared by transcription of a DNA copy of the genome, or by replication of an RNA copy, either in vivo or in vitro. Given the readily availability of easy-to-use in vitro transcription systems (e.g., SP6, T7, reticulocyte lysate, etc.), and also the convenience of maintaining a DNA copy of an RNA vector, it is expected that inventive ssRNA vectors will often be prepared by in vitro transcription, particularly with T7 or SP6 polymerase. Infectious cDNA clones can be used. Agrobacterially mediated gene transfer can be used to transfer viral nucleic acids such as viral vectors (either entire viral genomes or portions thereof) to plant cells using, e.g., agroinfiltration, according to methods known in the art.

The plant or plant portion may then be then maintained (e.g., cultured or grown) under conditions suitable for replication of a viral transcript. In certain embodiments of the invention virus spreads beyond the initially inoculated cell, e.g., locally from cell to cell and/or systemically from an initially inoculated leaf into additional leaves. However, in some embodiments of the invention virus does not spread. Thus a viral vector may contain genes encoding functional MP and/or CP, but may be lacking one or both of such genes. In general, a viral vector is introduced into (infects) multiple cells in the plant or portion thereof.

Following introduction of a viral vector into a plant, leaves are harvested. In general, leaves may be harvested at any time following introduction of a viral vector. However, it may be desirable to maintain a plant for a period of time following introduction of a viral vector into a plant, e.g., a period of time sufficient for viral replication and, optionally, spread of virus from the cells into which it was initially introduced. A clonal root culture (or multiple cultures) is prepared, e.g., by known methods further described below.

In general, any available method may be used to prepare a clonal root culture from a plant or plant tissue into which a viral vector has been introduced. One such method employs genes that exist in certain bacterial plasmids. These plasmids are found in various species of *Agrobacterium* that infect and transfer DNA to a wide variety of organisms. As a genus, Agrobacteria can transfer DNA to a large and diverse set of plant types including numerous dicot and monocot angiosperm species and gymnosperms (see, for example, Gelvin, et al., 2003, *Microbiol. Mol. Biol. Rev.*, 67:16, and references therein, all of which are incorporated herein by reference). The molecular basis of genetic transformation of plant cells is transfer from the bacterium and integration into the plant nuclear genome of a region of a large tumor-inducing (Ti) or rhizogenic (Ri) plasmid that resides within various Agrobacterial species. This region is referred to as the T-region when present in the plasmid and as T-DNA when excised from the plasmid. Generally, a single-stranded T-DNA molecule is transferred to a plant cell in naturally occurring Agrobacterial infection and is ultimately incorporated (in double-stranded form) into the genome. Systems based on Ti plasmids are widely used for introduction of foreign genetic material into plants and for production of transgenic plants.

Infection of plants with various Agrobacterial species and transfer of T-DNA has a number of effects. For example, *A. tumefaciens* causes crown gall disease while *A. rhizogenes* causes development of hairy roots at the site of infection, a condition known as "hairy root disease". Each root arises from a single genetically transformed cell. Thus root cells in roots are clonal, and each root represents a clonal population of cells. Roots produced by *A. rhizogenes* infection are characterized by a high growth rate and genetic stability (Giri et al., 2000, *Biotechnol. Adv.*, 18:1, and references therein, all of which are incorporated herein by reference). In addition, such roots are able to regenerate genetically stable plants (Giri et al., 2000, supra).

In general, the present invention encompasses the use of any strain of Agrobacteria (e.g. any *A. rhizogenes* strain) that is capable of inducing formation of roots from plant cells. As mentioned above, a portion of the Ri plasmid (Ri T-DNA) is responsible for causing hairy root disease. While transfer of this portion of the Ri plasmid to plant cells can conveniently be accomplished by infection with Agrobacteria harboring the Ri plasmid, the invention encompasses the use of alternative methods of introducing the relevant region into a plant cell. Such methods include any available method of introducing genetic material into plant cells including, but not limited to, biolistics, electroporation, PEG-mediated DNA uptake, Ti-based vectors, etc. Relevant portions of the Ri T-DNA can be introduced into plant cells by use of a viral vector. Ri genes can be included in the same vector that contains a polynucleotide encoding antigen of the invention or in a different viral vector, which can be the same or a different type to that of the vector that contains a polynucleotide encoding antigen of the invention. It is noted that the entire Ri T-DNA may not be required for production of hairy roots, and the invention encompasses use of portions of the Ri T-DNA, provided that such portions contain sufficient genetic material to induce root formation, as known in the art. Additional genetic material, e.g., genes present within the Ri plasmid but not within the T-DNA, may be transferred to a plant cell in accordance with the invention, particularly genes whose expression products facilitate integration of T-DNA into plant cell DNA.

In order to prepare a clonal root line in accordance with certain embodiments of the invention, harvested leaf portions are contacted with *A. rhizogenes* under conditions suitable for infection and transformation. Leaf portions are maintained in culture to allow development of hairy roots. Each root is clonal, i.e., cells in the root are derived from a single ancestral cell into which Ri T-DNA was transferred. In accordance with the invention, a portion of such ancestral cells will also contain a viral vector. Thus cells in a root derived from such an ancestral cell will also contain a viral vector since it will be replicated and will be transmitted during cell division. Thus a high proportion (e.g. at least 50%, at least 75%, at least 80%, at least 90%, at least 95%), all (100%), or substantially all (at least 98%) of cells will contain a viral vector. It is noted that since a viral vector is inherited by daughter cells within a clonal root, movement of a viral vector within the root is not necessary to maintain the viral vector throughout the root. Individual clonal hairy roots may be removed from the leaf portion and further cultured. Such roots are also referred to herein as root lines. Isolated clonal roots continue to grow following isolation.

A variety of different clonal root lines have been generated using the inventive methods. These root lines were generated using viral vectors containing polynucleotides encoding antigen of the invention (e.g., encoding, immunogenic peptide). Root lines were tested by Western blot. Root lines displayed a variety of different expression levels of various polypeptides. Root lines displaying high expression were selected and further cultured. These root lines were subsequently tested again and shown to maintain high levels of expression over extended periods of time, indicating stability. Expression levels were comparable to or greater than expression in intact plants infected with the same viral vector used to generate clonal root lines. In addition, stability of expression of root lines was superior to that obtained in plants infected with the same viral vector. Up to 80% of such virus-infected plants reverted to wild type after 2-3 passages. (Such passages involved inoculating plants with transcripts, allowing infection (local or systemic) to become established, taking a leaf sample, and inoculating fresh plants that are subsequently tested for expression.)

The root lines may be cultured on a large scale for production of antigen of the invention polypeptides as discussed further below. It is noted that clonal root lines (and cell lines derived from clonal root lines) can generally be maintained in medium that does not include various compounds, e.g., plant growth hormones such as auxins, cytokinins, etc., that are typically employed in culture of root and plant cells. This feature greatly reduces the expense associated with tissue culture, and the inventors expect that it will contribute significantly to the economic feasibility of protein production using plants.

Any of a variety of methods may be used to select clonal roots that express a polynucleotide encoding anthrax antigen(s) of the invention. Western blots, ELISA assays, etc., can be used to detect an encoded polypeptide. In the case of detectable markers such as GFP, alternative methods such as visual screens can be performed. If a viral vector that contains a polynucleotide that encodes a selectable marker is used, an appropriate selection can be imposed (e.g., leaf material and/or roots derived therefrom can be cultured in the presence of an appropriate antibiotic or nutritional condition and surviving roots identified and isolated). Certain viral vectors contain two or more polynucleotides encoding antigen of the invention, e.g., two or more polynucleotides encoding different polypeptides. If one of these is a selectable or detectable marker, clonal roots that are selected or detected by selecting for or detecting expression of the marker will have a high probability of also expressing a second polynucleotide. Screening for root lines that contain particular polynucleotides can also be performed using PCR and other nucleic acid detection methods.

Alternatively or additionally, clonal root lines can be screened for presence of virus by inoculating host plants that will form local lesions as a result of virus infection (e.g., hypersensitive host plants). For example, 5 mg of root tissue can be homogenized in 50 µl of phosphate buffer and used to inoculate a single leaf of a tobacco plant. If virus is present in root cultures, within two to three days characteristic lesions will appear on infected leaves. This means that a root line contains recombinant virus that carries a polynucleotide encoding antigen of the invention (target gene). If no local lesions are formed, there is no virus, and the root line is rejected as negative. This method is time- and cost-efficient. After initially screening for the presence of virus, roots that contain virus may be subjected to secondary screening, e.g., by Western blot or ELISA to select high expressers. Additional screens, e.g., screens for rapid growth, growth in particular media or under particular environmental conditions, etc., can be applied. These screening methods may, in general, be applied in the development of any of clonal root lines, clonal root cell lines, clonal plant cell lines, and/or clonal plants described herein.

As will be evident to one of ordinary skill in the art, a variety of modifications may be made to the description of the inventive methods for generating clonal root lines that contain a viral vector. Such modifications are within the scope of the invention. For example, while it is generally desirable to introduce viral vector into an intact plant or portion thereof prior to introduction of Ri T-DNA genes, in certain embodiments of the invention Ri-DNA is introduced prior to introducing viral vector. In addition, it is possible to contact intact plants with *A. rhizogenes* rather than harvesting leaf portions and then exposing them to the bacterium.

Other methods of generating clonal root lines from single cells of a plant or portion thereof that harbor a viral vector can be used (i.e., methods not using *A. rhizogenes* or genetic material from the Ri plasmid). For example, treatment with certain plant hormones or combinations of plant hormones is known to result in generation of roots from plant tissue.

Clonal Cell Lines Derived from Clonal Root Lines

As described above, the invention provides methods for generating clonal root lines, wherein cells in root lines contain a viral vector. As is well known in the art, a variety of different cell lines can be generated from roots. For example, root cell lines can be generated from individual root cells obtained from the root using a variety of known methods. Such root cell lines may be obtained from various different root cell types within the root. In general, root material is harvested and dissociated (e.g., physically and/or enzymatically digested) to release individual root cells, which are then further cultured. Complete protoplast formation is generally not necessary. If desired, root cells can be plated at very dilute cell concentrations, so as to obtain root cell lines from single root cells. Root cell lines derived in this manner are clonal root cell lines contain a viral vector. Such root cell lines therefore exhibit stable expression of a polynucleotide encoding antigen of the invention. Clonal plant cell lines can be obtained in a similar manner from clonal roots, e.g., by culturing dissociated root cells in the presence of appropriate plant hormones. Screens and successive rounds of enrichment can be used to identify cell lines that express a polynucleotide encoding antigen of the invention at high levels. However, if the clonal root line from which the cell line is derived already expresses at high levels, such additional screens may be unnecessary.

As in the case of clonal root lines, cells of a clonal root cell line are derived from a single ancestral cell that contains viral vector and will, therefore, also contain viral vector since it will be replicated and will be transmitted during cell division. Thus a high proportion (e.g., at least 50%, at least 75%, at least 80%, at least 90%, at least 95%), all (100%), or substantially all (at least 98%) of cells will contain viral vector. It is noted that since viral vector is inherited by daughter cells within a clonal root cell line, movement of viral vector among cells is not necessary to maintain the viral vector. Clonal root cell lines can be used for production of a polynucleotide encoding antigen of the invention as described below.

Clonal Plant Cell Lines

The present invention provides methods for generating a clonal plant cell line in which a plant viral vector is used to direct expression of a polynucleotide encoding antigen of the invention. According to the inventive method, one or more viral expression vector(s) including a polynucleotide encoding an anthrax antigen of the invention operably linked to a promoter is introduced into cells of a plant cell line that is maintained in cell culture. A number of plant cell lines from various plant types are known in the art, any of which can be used. Newly derived cell lines can be generated according to known methods for use in practicing the invention. A viral vector is introduced into cells of a plant cell line according to any of a number of methods. For example, protoplasts can be made and viral transcripts then electroporated into cells. Other methods of introducing a plant viral vector into cells of a plant cell line can be used.

A method for generating clonal plant cell lines in accordance with the invention and a viral vector suitable for introduction into plant cells (e.g., protoplasts) can be used as follows: Following introduction of viral vector, a plant cell line may be maintained in tissue culture. During this time viral vector may replicate, and polynucleotides encoding antigen of the invention may be expressed. Clonal plant cell lines are derived from culture, e.g., by a process of successive enrichment. For example, samples may be removed from culture, optionally with dilution so that concentration of cells is low, and plated in Petri dishes in individual droplets. Droplets are then maintained to allow cell division.

It will be appreciated that droplets may contain a variable number of cells, depending on the initial density of the culture and the amount of dilution. Cells can be diluted such that most droplets contain either 0 or 1 cell if it is desired to obtain clonal cell lines expressing a polynucleotide encoding antigen of the invention after only a single round of enrichment. However, it can be more efficient to select a concentration such that multiple cells are present in each droplet and then screen droplets to identify those that contain expressing cells. In general, any appropriate screening procedure can be employed. For example, selection or detection of a detectable marker such as GFP can be used. Western blots or ELISA assays can be used. Individual droplets (100 µl) contain more than enough cells for performance of these assays. Multiple rounds of enrichment are performed to isolate successively higher expressing cell lines. Single clonal plant cell lines (i.e., populations derived from a single ancestral cell) can be generated by further limiting dilution using standard methods for single cell cloning. However, it is not necessary to isolate individual clonal lines. A population containing multiple clonal cell lines can be used for expression of a polynucleotide encoding antigen of the invention.

In general, certain considerations described above for generation of clonal root lines apply to generation of clonal plant cell lines. For example, a diversity of viral vectors containing one or more polynucleotides encoding antigen of the invention can be used as can combinations of multiple different vectors. Similar screening methods can be used. As in the case of clonal root lines and clonal root cell lines, cells of a clonal plant cell line are derived from a single ancestral cell that contains viral vector and will, therefore, also contain viral vector since it will be replicated and will be transmitted during cell division. Thus a high proportion(e.g., at least 50%, at least 75%, at least 80%, at least 90%, at least 95%), all (100%), or substantially all (at least 98%) of cells will contain viral vector. It is noted that since viral vector is inherited by daughter cells within a clonal plant cell line, movement of viral vector among cells is not necessary to maintain viral vector. A clonal plant cell line can be used for production of a polypeptide encoding antigen of the invention as described below.

Clonal Plants

Clonal plants can be generated from clonal roots, clonal root cell lines, and/or clonal plant cell lines produced according to the various methods described above. Methods for the generation of plants from roots, root cell lines, and plant cell lines such as clonal root lines, clonal root cell lines, and clonal plant cell lines described herein are well known in the art (see, e.g., Peres et al., 2001, *Plant Cell, Tissue, and Organ Culture*, 65:37; and standard reference works on plant molecular biology and biotechnology cited elsewhere herein). The invention therefore provides a method of generating a clonal plant comprising steps of (i) generating a clonal root line, clonal root cell line, or clonal plant cell line according to any of the inventive methods described above; and (ii) generating a whole plant from a clonal root line, clonal root cell line, or clonal plant. Clonal plants may be propagated and grown according to standard methods.

As in the case of clonal root lines, clonal root cell lines, and clonal plant cell lines, cells of a clonal plant are derived from a single ancestral cell that contains viral vector and will, therefore, also contain viral vector since it will be replicated and will be transmitted during cell division. Thus a high proportion(e.g., at least 50%, at least 75%, at least 80%, at least 90%, at least 95%), all (100%), or substantially all (at least 98%) of cells will contain viral vector. It is noted that since viral vector is inherited by daughter cells within a clonal plant, movement of viral vector is not necessary to maintain the viral vector.

Sprouts and Sprouted Seedling Plant Expression Systems

Systems and reagents for generating a variety of sprouts and sprouted seedlings which are useful for production of anthrax antigen(s) according to the present invention have been described previously and are known in the art (see, for example, PCT Publication WO 04/43886, which is incorporated herein by reference). The present invention further provides sprouted seedlings, which may be edible, as a biomass containing an anthrax antigen peptide or protein. In certain aspects, biomass is provided directly for consumption of antigen compositions. In some aspects, biomass is processed prior to consumption, for example, by homogenizing, crushing, drying, or extracting. In certain aspects, an anthrax antigen is purified from biomass and formulated into a pharmaceutical composition.

Additionally provided are methods for producing anthrax antigens in sprouted seedlings that can be consumed or harvested live (e.g., sprouts, sprouted seedlings of the *Brassica* genus). In certain aspects, the present invention involves growing a seed to an edible sprouted seedling in a contained, regulatable environment (e.g., indoors, in a container, etc.). The seed can be a genetically engineered seed that contains an expression cassette encoding an anthrax antigen, which expression is driven by an exogenously inducible promoter. A variety of exogenously inducible promoters can be used that are inducible, for example, by light, heat, phytohormones, nutrients, etc.

In related embodiments, the present invention provides methods of producing anthrax antigen(s) in sprouted seedlings by first generating a seed stock for a sprouted seedling by transforming plants with an expression cassette that encodes anthrax antigen using an *Agrobacterium* transformation system, wherein expression of an anthrax antigen is driven by an inducible promoter. Transgenic seeds can be obtained from a transformed plant, grown in a contained, regulatable environment, and induced to express an anthrax antigen.

In some embodiments, methods are provided that involves infecting sprouted seedlings with a viral expression cassette encoding an anthrax antigen, expression of which may be driven by any of a viral promoter or an inducible promoter. Sprouted seedlings are grown for two to fourteen days in a contained, regulatable environment or at least until sufficient levels of anthrax antigen have been obtained for consumption or harvesting.

The present invention further provides systems for producing anthrax antigen(s) in sprouted seedlings that include a housing unit with climate control and a sprouted seedling containing an expression cassette that encodes one or more anthrax antigens, wherein expression is driven by a constitutive or inducible promoter. The inventive systems can provide unique advantages over the outdoor environment or greenhouse, which cannot be controlled. Thus the present invention enables a grower to precisely time induction of expression of an anthrax antigen. It can also greatly reduce the cost of producing anthrax antigen(s).

In certain aspects, transiently transfected sprouts contain viral vector sequences encoding an inventive anthrax antigen. Seedlings are grown for a time period so as to allow for production of viral nucleic acid in a sprout, followed by a period of growth wherein multiple copies of virus are produced, thereby resulting in production of antigen.

In certain aspects, genetically engineered seeds or embryos that contain a transgene encoding an anthrax antigen are grown to the sprouted seedling stage in a contained, regulatable environment. The contained, regulatable environment may be a housing unit or room in which seeds can be grown indoors. All environmental factors of the contained, regulatable environment may be controlled. Since sprouts do not require light to grow, and lighting can be expensive, genetically engineered seeds or embryos may be grown to the sprouted seedling stage indoors in the absence of light.

Other environmental factors that can be regulated in the contained, regulatable environment of the present invention include temperature, humidity, water, nutrients, gas (e.g., $O_2$ or $CO_2$ content or air circulation), chemicals (small molecules such as sugars and sugar derivatives or hormones such as such as the phytohormones gibberellic or absisic acid, etc.) and the like.

According to certain methods of the present invention, expression of a transgene encoding an anthrax antigen may be controlled by an exogenously inducible promoter. Exogenously inducible promoters are caused to increase or decrease expression of a transgene in response to an external, rather than an internal stimulus. A number of these environmental factors can act as inducers for expression of transgenes carried by expression cassettes of genetically engineered sprouts. The promoter may be a heat-inducible promoter, such as a heat-shock promoter. For example, using as heat-shock promoter the temperature of the contained environment may simply be raised to induce expression of a transgene. Other promoters include light inducible promoters. Light-inducible promoters can be maintained as constitutive promoters if light in the contained regulatable environment is always on. Alternatively or additionally, expression of a transgene can be turned on at a particular time during development by simply turning on light. The promoter may be a chemically inducible promoter is used to induce expression of a transgene. According to these embodiments, the chemical could simply be misted or sprayed onto the seed, embryo, or seedling to induce expression of a transgene. Spraying and misting can be precisely controlled and directed onto the target seed, embryo, or seedling to which it is intended. The contained environment is devoid of wind or air currents, which could disperse chemical away from the intended target, so that the chemical stays on the target for which it was intended.

According to the present invention, the time expression is induced can be selected to maximize expression of an anthrax antigen in sprouted seedling by the time of harvest. Inducing expression in an embryo at a particular stage of growth, for example, inducing expression in an embryo at a particular number of days after germination, may result in maximum synthesis of an anthrax antigen at the time of harvest. For example, inducing expression from the promoter 4 days after germination may result in more protein synthesis than inducing expression from the promoter after 3 days or after 5 days. Those skilled in the art will appreciate that maximizing expression can be achieved by routine experimentation. In certain methods, sprouted seedlings are harvested at about 1, 2, 3, 4, 5, 6, 7, 8, 9, 10, 11, or 12 days after germination.

In cases where an expression vector has a constitutive promoter instead of an inducible promoter, a sprouted seedling may be harvested at a certain time after transformation of the sprouted seedling. For example, if a sprouted seedling were virally transformed at an early stage of development, for example, at the embryo stage, sprouted seedlings may be harvested at a time when expression is at its maximum post-transformation, e.g., at about 1, 2, 3, 4, 5, 6, 7, 8, 9, 10, 11, 12, 13, or 14 days post-transformation. It could also be that sprouts develop one, two, three or more months post-transformation, depending on the germination of the seed.

Generally, once expression of anthrax antigen begins, seeds, embryos, or sprouted seedlings are allowed to grow until sufficient levels of anthrax antigen are expressed. In certain aspects, sufficient levels are levels that would provide a therapeutic benefit to a patient if harvested biomass were eaten raw. Alternatively or additionally, sufficient levels are levels from which an anthrax antigen can be concentrated or purified from biomass and formulated into a pharmaceutical composition that provides a therapeutic benefit to a patient upon administration. Typically, the antigen is not a protein expressed in a sprouted seedling in nature. At any rate, an anthrax antigen is typically expressed at concentrations above that which would be present in a sprouted seedling in nature.

Once expression of an anthrax antigen is induced, growth is allowed to continue until the sprouted seedling stage, at which time sprouted seedlings are harvested. Sprouted seedlings can be harvested live. Harvesting live sprouted seedlings has several advantages including minimal effort and breakage. Sprouted seedlings of the present invention may be grown hydroponically, making harvesting a simple matter of lifting a sprouted seedling from its hydroponic solution. No soil is required for growth of sprouted seedlings of the invention, but may be provided if deemed necessary or desirable by the skilled artisan. Because sprouts can be grown without soil, no cleansing of sprouted seedling material is required at the time of harvest. Being able to harvest a sprouted seedling directly from its hydroponic environment without washing or scrubbing minimizes breakage of harvested material. Breakage and wilting of plants induces apoptosis. During apoptosis, certain proteolytic enzymes become active, which can degrade a pharmaceutical protein expressed in a sprouted seedling, resulting in decreased therapeutic activity of the protein. Apoptosis-induced proteolysis can significantly decrease yield of protein from mature plants. Using the methods of the present invention, apoptosis may be avoided when no harvesting takes place until the moment proteins are extracted from a plant.

For example, live sprouts may be ground, crushed, or blended to produce a slurry of sprouted seedling biomass, in a buffer containing protease inhibitors. Buffer may be maintained at about 4° C. In some aspects, sprouted seedling biomass is air-dried, spray dried, frozen, or freeze-dried. As in mature plants, some of these methods, such as air-drying, may result in a loss of activity of a pharmaceutical protein. However, because sprouted seedlings are very small and have a large surface area to volume ratio, this is much less likely to occur. Those skilled in the art will appreciate that many techniques for harvesting biomass that minimize proteolysis of expressed protein are available and could be applied to the present invention.

In some embodiments, sprouted seedlings are edible. In certain embodiments, sprouted seedlings expressing sufficient levels of anthrax antigens are consumed upon harvesting (e.g., immediately after harvest, within minimal period following harvest) so that absolutely no processing occurs before sprouted seedlings are consumed. In this way, any harvest-induced proteolytic breakdown of an anthrax antigen before administration of the anthrax antigen to a patient in need of treatment is minimized. For example, sprouted seedlings that are ready to be consumed can be delivered directly to a patient. Alternatively or additionally, genetically engineered seeds or embryos are delivered to a patient in need of treatment and grown to the sprouted seedling stage by a patient. In one aspect, a supply of genetically engineered sprouted seedlings is provided to a patient, or to a doctor who will be treating patients, so that a continual stock of sprouted seedlings expressing certain desirable anthrax antigens may be cultivated. This may be particularly valuable for populations in developing countries, where expensive pharmaceuticals are not affordable or deliverable. The ease with which sprouted seedlings of the invention can be grown makes sprouted seedlings of the present invention particularly desirable for such developing populations.

The regulatable nature of the contained environment imparts advantages to the present invention over growing plants in the outdoor environment. In general, growing genetically engineered sprouted seedlings that express pharmaceutical proteins in plants provides a pharmaceutical product faster (because plants are harvested younger) and with less effort, risk, and regulatory considerations than growing genetically engineered plants. The contained, regulatable environment used in the present invention reduces or eliminates the risk of cross-pollinating plants in nature.

For example, a heat inducible promoter likely would not be used in the outdoors because outdoor temperature cannot be controlled. A promoter would be turned on any time outdoor temperature rose above a certain level. Similarly, a promoter would be turned off every time outdoor temperature dropped. Such temperature shifts could occur in a single day, for example, turning expression on in the daytime and off at night. A heat inducible promoter, such as those described herein, would not even be practical for use in a greenhouse, which is susceptible to climatic shifts to almost the same degree as outdoors. Growth of genetically engineered plants in a greenhouse is quite costly. In contrast, in the present system, every variable can be controlled so that the maximum amount of expression can be achieved with every harvest.

In certain embodiments, sprouted seedlings of the present invention are grown in trays that can be watered, sprayed, or misted at any time during the development of a sprouted seedling. For example, the tray may be fitted with one or more watering, spraying, misting, and draining apparatus that can deliver and/or remove water, nutrients, chemicals etc. at specific time and at precise quantities during development of a sprouted seedling. For example, seeds require sufficient moisture to keep them damp. Excess moisture drains through holes in trays into drains in the floor of the room. Typically, drainage water is treated as appropriate for removal of harmful chemicals before discharge back into the environment.

Another advantage of trays is that they can be contained within a very small space. Since no light is required for sprouted seedlings to grow, trays containing seeds, embryos, or sprouted seedlings may be tightly stacked vertically on top of one another, providing a large quantity of biomass per unit floor space in a housing facility constructed specifically for these purposes. In addition, stacks of trays can be arranged in horizontal rows within the housing unit. Once seedlings have grown to a stage appropriate for harvest (about two to fourteen days) individual seedling trays are moved into a processing facility, either manually or by automatic means, such as a conveyor belt.

The system of the present invention is unique in that it provides a sprouted seedling biomass, which is a source of an anthrax antigen. Whether consumed directly or processed into the form of a pharmaceutical composition, because sprouted seedlings are grown in a contained, regulatable environment, sprouted seedling biomass and/or pharmaceutical composition derived from biomass can be provided to a consumer at low cost. In addition, the fact that conditions for growth of sprouted seedlings can be controlled makes the quality and purity of the product consistent. The contained, regulatable environment of the invention obviates many safety regulations of the EPA that can prevent scientists from growing genetically engineered agricultural products out of doors.

Transformed Sprouts

A variety of methods can be used to transform plant cells and produce genetically engineered sprouted seedlings. Two available methods for transformation of plants that require that transgenic plant cell lines be generated in vitro, followed by regeneration of cell lines into whole plants include *Agrobacterium tumefaciens* mediated gene transfer and microprojectile bombardment or electroporation. Viral transformation is a more rapid and less costly method of transforming embryos and sprouted seedlings that can be harvested without an experimental or generational lag prior to obtaining the desired product. For any of these techniques, the skilled artisan would appreciate how to adjust and optimize transformation protocols that have traditionally been used for plants, seeds, embryos, or spouted seedlings.

*Agrobacterium* Transformation Expression Cassettes

*Agrobacterium* is a representative genus of the gram-negative family Rhizobiaceae. This species is responsible for plant tumors such as crown gall and hairy root disease. In dedifferentiated plant tissue, which is characteristic of tumors, amino acid derivatives known as opines are produced by *Agrobacterium* and catabolized by the plant. Bacterial genes responsible for expression of opines are a convenient source of control elements for chimeric expression cassettes. According to the present invention, *Agrobacterium* transformation system may be used to generate edible sprouted seedlings, which are merely harvested earlier than mature plants. *Agrobacterium* transformation methods can easily be applied to regenerate sprouted seedlings expressing anthrax antigens.

In general, transforming plants involves transformation of plant cells grown in tissue culture by co-cultivation with an *Agrobacterium tumefaciens* carrying a plant/bacterial vector. The vector contains a gene encoding an anthrax antigen. *Agrobacterium* transfers vector to a plant host cell and is then eliminated using antibiotic treatment. Transformed plant cells expressing anthrax antigen are selected, differentiated, and finally regenerated into complete plantlets (Hellens et al., 2000, *Plant Molecular Biology*, 42:819; Pilon-Smits et al., 1999, *Plant Physiolog.*, 119:123; Barfield et al., 1991, *Plant Cell Reports*, 10:308; and Riva et al., 1998, *J. Biotech.*, 1(3); each of which is incorporated by reference herein).

Expression vectors for use in the present invention include a gene (or expression cassette) encoding an anthrax antigen designed for operation in plants, with companion sequences upstream and downstream of the expression cassette. Companion sequences are generally of plasmid or viral origin and provide necessary characteristics to the vector to transfer DNA from bacteria to a desired plant host.

The basic bacterial/plant vector construct may desirably provide a broad host range prokaryote replication origin, a prokaryote selectable marker. Suitable prokaryotic selectable markers include resistance toward antibiotics such as ampicillin or tetracycline. Other DNA sequences encoding additional functions that are well known in the art may be present in the vector.

*Agrobacterium* T-DNA sequences are required for *Agrobacterium* mediated transfer of DNA to the plant chromosome. Tumor-inducing genes of T-DNA are typically removed and replaced with sequences encoding anthrax antigen. T-DNA border sequences are retained because they initiate integration of T-DNA region into the plant genome. If expression of anthrax antigen is not readily amenable to detection, the bacterial/plant vector construct may include a selectable marker gene suitable for determining if a plant cell has been transformed, e.g., the nptII kanamycin resistance gene. On the same or different bacterial/plant vector (Ti plasmid) are Ti sequences. Ti sequences include virulence genes, which encode a set of proteins responsible for excision, transfer and integration of T-DNA into the plant genome (Schell, *Science* (1987) 237:1176-1183). Other sequences suitable for permitting integration of the heterologous sequence into the plant genome may include transposon sequences, and the like, for homologous recombination.

Certain constructs will include an expression cassette encoding an antigen protein. One, two, or more expression cassettes may be used in a given transformation. The recombinant expression cassette contains, in addition to the anthrax antigen encoding sequence, at least the following elements: a promoter region, plant 5' untranslated sequences, initiation codon (depending upon whether or not the expressed gene has its own), and transcription and translation termination sequences. In addition, transcription and translation terminators may be included in expression cassettes or chimeric genes of the present invention. Signal secretion sequences that allow processing and translocation of protein, as appropriate, may be included in the expression cassette. A variety of promoters, signal sequences, and transcription and translation terminators are described (see, for example, Lawton et al., 1987, *Plant Mol. Biol.,* 9:315; and U.S. Pat. No. 5,888, 789, incorporated herein by reference). In addition, structural genes for antibiotic resistance are commonly utilized as a selection factor (Fraley et al. 1983, *Proc. Natl. Acad. Sci., USA,* 80:4803, incorporated herein by reference). Unique restriction enzyme sites at the 5' and 3' ends of the cassette allow for easy insertion into a pre-existing vector. Other binary vector systems for *Agrobacterium*-mediated transformation, carrying at least one T-DNA border sequence are described in PCT/EP99/07414, incorporated herein by reference.

Regeneration

Seeds of transformed plants may be harvested, dried, cleaned, and tested for viability and for presence and expression of a desired gene product. Once this has been determined, seed stock is typically stored under appropriate conditions of temperature, humidity, sanitation, and security to be used when necessary. Whole plants may then be regenerated from cultured protoplasts, as described (see, e.g., Evans et al., *Handbook of Plant Cell Cultures,* Vol. 1: MacMillan Publishing Co., New York, 1983; and Vasil (ed.), *Cell Culture and Somatic Cell Genetics of Plants,* Acad. Press, Orlando, Fla., Vol. I, 1984, and Vol. III, 1986, incorporated herein by reference). In certain aspects, plants are regenerated only to the sprouted seedling stage. In some aspects, whole plants are regenerated to produce seed stocks and sprouted seedlings are generated from seeds of the seed stock.

All plants from which protoplasts can be isolated and cultured to give whole, regenerated plants can be transformed by the present invention so that whole plants are recovered that contain the transferred gene. It is known that practically all plants can be regenerated from cultured cells or tissues, including, but not limited to, all major species of plants that produce edible sprouts. Some suitable plants include alfalfa, mung bean, radish, wheat, mustard, spinach, carrot, beet, onion, garlic, celery, rhubarb, a leafy plant such as cabbage or lettuce, watercress or cress, herbs such as parsley, mint, or clovers, cauliflower, broccoli, soybean, lentils, edible flowers such as sunflower etc.

Means for regeneration vary from one species of plants to the next. However, those skilled in the art will appreciate that generally a suspension of transformed protoplants containing copies of the heterologous gene is first provided. Callus tissue is formed and shoots may be induced from callus and subsequently rooted. Alternatively or additionally, embryo formation can be induced from the protoplast suspension. These embryos germinate as natural embryos to form plants. Steeping a seed in water or spraying the seed with water to increase the moisture content of the seed to between 35-45% initiates germination. For germination to proceed, seeds are typically maintained in air saturated with water under controlled temperature and airflow conditions. Culture media will generally contain various amino acids and hormones, such as auxin and cytokinins. It is advantageous to add glutamic acid and proline to the medium, especially for such species as alfalfa. Shoots and roots normally develop simultaneously. Efficient regeneration will depend on the medium, the genotype, and the history of the culture. If these three variables are controlled, then regeneration is fully reproducible and repeatable.

The mature plants, grown from transformed plant cells, are selfed and non-segregating, homozygous transgenic plants are identified. An inbred plant produces seeds containing inventive antigen-encoding sequences. Such seeds can be germinated and grown to the sprouted seedling stage to produce anthrax antigen(s) according to the present invention.

In related embodiments, seeds of the present invention may be formed into seed products and sold with instructions on how to grow seedlings to the appropriate sprouted seedling stage for administration or harvesting into a pharmaceutical composition. In some related embodiments, hybrids or novel varieties embodying desired traits may be developed from inbred plants of the invention.

Direct Integration

Direct integration of DNA fragments into the genome of plant cells by microprojectile bombardment or electroporation may be used in the present invention (see, e.g., Kikkert et al., 1999, In Vitro *Cellular & Developmental Biology. Plant: Journal of the Tissue Culture Association,* 35:43; and Bates et al., 1994, *Mol. Biotech.,* 2:135). More particularly, vectors that express anthrax antigen(s) of the present invention can be introduced into plant cells by a variety of techniques. As described above, vectors may include selectable markers for use in plant cells. Vectors may include sequences that allow their selection and propagation in a secondary host, such as sequences containing an origin of replication and selectable marker. Typically, secondary hosts include bacteria and yeast. In one embodiment, the secondary host is bacteria (e.g., *Escherichia coli*, the origin of replication is a colE1-type origin of replication) and the selectable marker is a gene encoding ampicillin resistance. Such sequences are well known in the art and are commercially available (e.g., Clontech, Palo Alto, Calif. or Stratagene, La Jolla, Calif.).

Vectors of the present invention may be modified to intermediate plant transformation plasmids that contain a region of homology to an *Agrobacterium tumefaciens* vector, a T-DNA border region from *Agrobacterium tumefaciens*, and antigen encoding nucleic acids or expression cassettes described above. Further vectors may include a disarmed plant tumor inducing plasmid of *Agrobacterium tumefaciens*.

According to this embodiment, direct transformation of vectors invention may involve microinjecting vectors directly into plant cells by the use of micropipettes to mechanically transfer the recombinant DNA (see, e.g., Crossway, 1985, *Mol. Gen. Genet.,* 202:179, incorporated herein by reference). Genetic material may be transferred into the plant cell using polyethylene glycols (see, e.g., Krens et al., 1982, *Nature,* 296:72). Another method of introducing nucleic acids into plants via high velocity ballistic penetration by small particles with a nucleic acid either within the matrix of small beads or particles, or on the surface (see, e.g., Klein et al., 1987, *Nature,* 327:70; and Knudsen et al., *Planta,* 185:330). Yet another method of introduction is fusion of protoplasts with other entities, either minicells, cells, lysosomes, or other fusible lipid-surfaced bodies (see, e.g., Fraley et al., 1982, *Proc. Natl. Acad. Sci., USA,* 79:1859). Vectors of the invention may be introduced into plant cells by electroporation (see, e.g., Fromm et al., 1985, *Proc. Natl. Acad. Sci., USA,* 82:5824). According to this technique, plant protoplasts are electroporated in the presence of plasmids containing the gene construct. Electrical impulses of high field strength reversibly permeabilize biomembranes allowing introduction of plasmids. Electroporated plant protoplasts reform the cell wall divide and form plant callus, which can be regenerated to form sprouted seedlings of the invention. Those skilled in the art will appreciate how to utilize these methods to transform plants cells that can be used to generate edible sprouted seedlings.

Viral Transformation

Similar to conventional expression systems, plant viral vectors can be used to produce full-length proteins, including full length antigen. According to the present invention, plant virus vectors may be used to infect and produce antigen(s) in seeds, embryos, sprouted seedlings, etc. Viral system that can be used to express everything from short peptides to large complex proteins. Specifically, using tobamoviral vectors is described (see, for example, McCormick et al., 1999, *Proc. Natl. Acad. Sci., USA,* 96:703; Kumagai et al. 2000, *Gene,* 245:169; and Verch et al., 1998, *J. Immunol. Methods,* 220: 69; each of which is incorporated herein by reference). Thus, plant viral vectors have a demonstrated ability to express short peptides as well as large complex proteins.

In certain embodiments, transgenic sprouts, which express anthrax antigen, are generated utilizing a host/virus system. Transgenic sprouts produced by viral infection provide a source of transgenic protein that has already been demonstrated to be safe. For example, sprouts are free of contamination with animal pathogens. Unlike, for example, tobacco, proteins from an edible sprout could at least in theory be used in oral applications without purification, thus significantly reducing costs. In addition, a virus/sprout system offers a much simpler, less expensive route for scale-up and manufacturing, since transgenes are introduced into virus, which can be grown up to a commercial scale within a few days. In contrast, transgenic plants can require up to 5-7 years before sufficient seeds or plant material is available for large-scale trials or commercialization.

According to the present invention, plant RNA viruses have certain advantages, which make them attractive as vectors for foreign protein expression. The molecular biology and pathology of a number of plant RNA viruses are well characterized and there is considerable knowledge of virus biology, genetics, and regulatory sequences. Most plant RNA viruses have small genomes and infectious cDNA clones are available to facilitate genetic manipulation. Once infectious virus material enters a susceptible host cell, it replicates to high levels and spreads rapidly throughout the entire sprouted seedling (one to ten days post inoculation). Virus particles are easily and economically recovered from infected sprouted seedling tissue. Viruses have a wide host range, enabling use of a single construct for infection of several susceptible species. These characteristics are readily transferable to sprouts.

Foreign sequences can be expressed from plant RNA viruses, typically by replacing one of viral genes with desired sequence, by inserting foreign sequences into the virus genome at an appropriate position, or by fusing foreign peptides to structural proteins of a virus. Moreover, any of these approaches can be combined to express foreign sequences by trans-complementation of vital functions of a virus. A number of different strategies exist as tools to express foreign sequences in virus-infected plants using tobacco mosaic virus (TMV), alfalfa mosaic virus (AlMV), and chimeras thereof.

The genome of AlMV is a representative of the Bromoviridae family of viruses and consists of three genomic RNAs (RNAs1-3) and subgenomic RNA (RNA4). Genomic RNAs1 and 2 encode virus replicase proteins P1 and 2, respectively. Genomic RNA3 encodes cell-to-cell movement protein P3 and coat protein (CP). CP is translated from subgenomic RNA4, which is synthesized from genomic RNA3, and is required to start infection. Studies have demonstrated involvement of CP in multiple functions, including genome activation, replication, RNA stability, symptom formation, and RNA encapsidation (see e.g., Bol et al., 1971, *Virology,* 46:73; Van Der Vossen et al., 1994, *Virology* 202:891; Yusibov et al., *Virology,* 208:405; Yusibov et al., 1998, *Virology,* 242:1; Bol et al., (Review, 100 refs.), 1999, *J. Gen. Virol.,* 80:1089; De Graaff, 1995, *Virology,* 208:583; Jaspars et al., 1974, *Adv. Virus Res.,* 19:37; Loesch-Fries, 1985, *Virology,* 146:177; Neeleman et al., 1991, *Virology,* 181:687; Neeleman et al., 1993, *Virology,* 196: 883; Van Der Kuyl et al., 1991, *Virology,* 183:731; and Van Der Kuyl et al., 1991, *Virology,* 185:496).

Encapsidation of viral particles is typically required for long distance movement of virus from inoculated to un-inoculated parts of the seed, embryo, or sprouted seedling and for systemic infection. According to the present invention, inoculation can occur at any stage of plant development. In embryos and sprouts, spread of inoculated virus should be very rapid. Virions of AlMV are encapsidated by a unique CP (24 kD), forming more than one type of particle. The size (30- to 60-nm in length and 18 nm in diameter) and shape (spherical, ellipsoidal, or bacilliform) of a particle depends on the size of the encapsidated RNA. Upon assembly, the N-terminus of AlMV CP is thought to be located on the surface of virus particles and does not appear to interfere with virus assembly (Bol et al., 1971, *Virology,* 6:73). Additionally, AlMV CP with an additional 38-amino acid peptide at its N-terminus forms particles in vitro and retains biological activity (Yusibov et al., 1995, *J. Gen. Virol.,* 77:567).

AlMV has a wide host range, which includes a number of agriculturally valuable crop plants, including plant seeds, embryos, and sprouts. Together, these characteristics make AlMV CP an excellent candidate as a carrier molecule and AlMV an attractive candidate vector for expression of foreign sequences in a plant at the sprout stage of development. Moreover, upon expression from a heterologous vector such as TMV, AlMV CP encapsidates TMV genome without interfering with virus infectivity (Yusibov et al., 1997, *Proc. Natl. Acad. Sci., USA,* 94:5784, incorporated herein by reference). This allows for use of TMV as a carrier virus for AlMV CP fused to foreign sequences.

TMV, the prototype of tobamoviruses, has a genome consisting of a single plus-sense RNA encapsidated with a 17.0 kD CP, which results in rod-shaped particles (300 nm in length). CP is the only structural protein of TMV and is required for encapsidation and long distance movement of virus in an infected host (Saito et al., 1990, *Virology,* 176: 329). 183 and 126 kD proteins are translated from genomic RNA and are required for virus replication (Ishikawa et al., 1986, *Nucleic Acids Res.,* 14:8291). 30 kD protein is the cell-to-cell movement protein of virus (Meshi et al., 1987, *EMBO J.,* 6:2557). Movement and coat proteins are translated from subgenomic mRNAs (Hunter et al., 1976, *Nature,* 260: 759; Bruening et al., 1976, *Virology,* 71:498; and Beachy et al., 1976, *Virology,* 73:498; each of which is incorporated herein by reference).

Other methods of transforming plant tissues include transforming the flower of a plant. Transformation of *Arabidopsis thaliana* can be achieved by dipping plant flowers into a solution of *Agrobacterium tumefaciens* (Curtis et al., 2001, *Transgenic Research,* 10:363; and Qing et al., 2000, *Molecular Breeding: New Strategies in Plant Improvement,* 1:67). Transformed plants are formed in the population of seeds generated by "dipped" plants. At a specific point during flower development, a pore exists in the ovary wall through which *Agrobacterium tumefaciens* gains access to the interior of the ovary. Once inside the ovary, the *Agrobacterium tumefaciens* proliferates and transforms individual ovules (Desfeux et al., 2000, *Plant Physiology,* 123:895). Transformed ovules follow the typical pathway of seed formation within the ovary.

Production and Isolation of Antigen

In general, standard methods known in the art may be used for culturing or growing plants, plant cells, and/or plant tissues of the invention (e.g., clonal plants, clonal plant cells, clonal roots, clonal root lines, sprouts, sprouted seedlings, plants, etc.) for production of antigen(s). A wide variety of culture media and bioreactors have been employed to culture hairy root cells, root cell lines, and plant cells (see, for example, Giri et al., 2000, *Biotechnol. Adv.*, 18:1; Rao et al., 2002, *Biotechnol. Adv.*, 20:101; and references in both of the foregoing, all of which are incorporated herein by reference. Clonal plants may be grown in any suitable manner.

In a certain embodiments, anthrax antigens of the invention may be produced by any known method. In some embodiments, an anthrax antigen is expressed in a plant or portion thereof Proteins are isolated and purified in accordance with conventional conditions and techniques known in the art. These include methods such as extraction, precipitation, chromatography, affinity chromatography, electrophoresis, and the like. The present invention involves purification and affordable scaling up of production of anthrax antigen(s) using any of a variety of plant expression systems known in the art and provided herein, including viral plant expression systems described herein.

In many embodiments of the present invention, it will be desirable to isolate vaccine antigen products. Where a protein of the invention is produced from plant tissue(s) or a portion thereof, e.g., roots, root cells, plants, plant cells, that express them, methods described in further detail herein, or any applicable methods known in the art may be used for any of partial or complete isolation from plant material. Where it is desirable to isolate the expression product from some or all of plant cells or tissues that express it, any available purification techniques may be employed. Those of ordinary skill in the art are familiar with a wide range of fractionation and separation procedures (see, for example, Scopes et al., *Protein Purification: Principles and Practice*, $3^{rd}$ Ed., Janson et al., 1993; *Protein Purification. Principles, High Resolution Methods, and Applications*, Wiley-VCH, 1998; Springer-Verlag, NY, 1993; Roe, *Protein Purification Techniques*, Oxford University Press, 2001; each of which is incorporated herein by reference). Often, it will be desirable to render the product more than about 50%, 60%, 70%, 80%, 85%, 90%, 91%, 92%, 93%, 94%, 95%, 96%, 97%, 98%, or 99% pure. See, e.g., U.S. Pat. Nos. 6,740,740 and 6,841,659 for discussion of certain methods useful for purifying substances from plant tissues or fluids.

Those skilled in the art will appreciate that a method of obtaining a desired vaccine products is by extraction. Plant material (e.g., roots, leaves, etc.) may be extracted to remove desired products from residual biomass, thereby increasing concentration and purity of the product. Plants may be extracted in a buffered solution. For example, plant material may be transferred into an amount of ice-cold water at a ratio of one to one by weight that has been buffered with, e.g., phosphate buffer. Protease inhibitors can be added as required. Plant material can be disrupted by vigorous blending or grinding while suspended in buffer solution and extracted biomass removed by filtration or centrifugation. Product carried in solution can be further purified by additional steps or converted to a dry powder by freeze-drying or precipitation. Extraction can be carried out by pressing. Plants or roots can be extracted by pressing in a press or by being crushed as they are passed through closely spaced rollers. Fluids expressed from crushed plants or roots are collected and processed according to methods well known in the art. Extraction by pressing allows release of products in a more concentrated form. However, overall yield of product may be lower than if product were extracted in solution.

Vaccines

The present invention provides pharmaceutical antigen proteins for therapeutic use, such as antigen protein(s) or an immunogenic portion(s) thereof active as a vaccine for therapeutic and/or prophylactic treatment of anthrax infection. Further, the invention provides veterinary use, as such antigen protein or immunogenic portion thereof is active in veterinary applications. In certain embodiments, antigen(s) may be produced by plant(s) or portion thereof (e.g., root, cell, sprout, cell line, plant, etc.) of the invention. In certain embodiments, provided anthrax antigens are expressed in plants, plant cells, and/or plant tissues (e.g., sprouts, sprouted seedlings, roots, root culture, clonal cells, clonal cell lines, clonal plants, etc.), and can be used directly from the plant or partially purified or purified in preparation for pharmaceutical administration to a subject.

The present invention provides plants, plant cells, and plant tissues expressing antigen(s) that maintains pharmaceutical activity when administered to a subject in need thereof. Exemplary subjects include vertebrates, (e.g., mammals, such as humans). According to the present invention, subjects include veterinary subjects such as bovines, ovines, canines, felines, etc. In certain aspects, an edible plant or portion thereof (e.g., sprout, root) is administered orally to a subject in a therapeutically effective amount. In some aspects, one or more anthrax antigen(s) is provided in a pharmaceutical preparation, as described herein.

Vaccine compositions of the invention comprise one or more anthrax antigens. In certain embodiments, at least two anthrax antigens of the invention are included in an administered vaccine composition.

According to the present invention, treatment of a subject with a vaccine antigen is intended to elicit a physiological effect. A vaccine protein may have healing curative or palliative properties against a disorder or disease and can be administered to ameliorate relieve, alleviate, delay onset of, reverse or lessen symptoms or severity of a disease or disorder. A vaccine antigen may have prophylactic properties and can be used to prevent or delay the onset of a disease or to lessen the severity of such disease, disorder, or pathological condition when it does emerge. A physiological effect elicited by treatment of a subject with antigen according to the present invention can include an effective immune response such that infection by an organism is thwarted.

In some embodiments, inventive vaccines are delivered by oral and/or mucosal routes. Oral and/or mucosal delivery has the potential to prevent infection of mucosal tissues, the primary gateway of infection for many pathogens. Oral and/or mucosal delivery can prime systemic immune response. There has been considerable progress in the development of heterologous expression systems for oral administration of antigens that stimulate mucosal-immune system and can prime systemic immunity. Previous efforts at delivery of oral vaccine however, have demonstrated a requirement for considerable quantities of antigen in achieving efficacy. Thus, the economical production of large quantities of target antigens is a prerequisite for creation of effective oral vaccines. Development of plants expressing antigens, including thermostable antigens, represents a more realistic approach to such difficulties.

The pharmaceutical preparations of the present invention can be administered in a wide variety of ways to a subject, such as, for example, orally, nasally, enterally, parenterally, intramuscularly or intravenously, rectally, vaginally, topically, ocularly, pulmonarily, or by contact application. In certain embodiments, an anthrax antigen expressed in a plant or portion thereof is administered to a subject orally by direct administration of a plant to a subject. In some aspects, a vaccine protein expressed in a plant or portion thereof is extracted and/or purified, and used for the preparation of a pharmaceutical composition. It may be desirable to formulate such isolated products for their intended use (e.g., as a pharmaceutical agent, vaccine composition, etc.). In some embodiments, it will be desirable to formulate products together with some or all of plant tissues that express them.

Where it is desirable to formulate the product together with plant material, it will often be desirable to have utilized a plant that is not toxic to the relevant recipient (e.g., a human or other animal). Relevant plant tissue (e.g., cells, roots, leaves) may simply be harvested and processed according to techniques known in the art, with due consideration to maintaining activity of the expressed product. In certain embodiments of the invention, it is desirable to have expressed the vaccine antigen in an edible plant (and, specifically in edible portions of the plant) so that the material can subsequently be eaten. For instance, where the vaccine antigen is active after oral delivery (when properly formulated), it may be desirable to produce the antigen protein in an edible plant portion, and to formulate the expressed vaccine antigen for oral delivery together with the some or all of the plant material with which the protein was expressed.

Vaccine antigens provided may be formulated according to known techniques. For example, an effective amount of a vaccine product can be formulated together with one or more organic or inorganic, liquid or solid, pharmaceutically suitable carrier materials. A vaccine antigen produced according to the present invention may be employed in dosage forms such as tablets, capsules, troches, dispersions, suspensions, solutions, gelcaps, pills, caplets, creams, ointments, aerosols, powder packets, liquid solutions, solvents, diluents, surface active agents, isotonic agents, thickening or emulsifying agents, preservatives, and solid bindings, as long as the biological activity of the protein is not destroyed by such dosage form.

In general, the compositions may comprise any of a variety of different pharmaceutically acceptable carrier(s), adjuvant(s), or vehicle(s), or a combination of one or more such carrier(s), adjuvant(s), or vehicle(s). As used herein the language "pharmaceutically acceptable carrier, adjuvant, or vehicle" includes solvents, dispersion media, coatings, antibacterial and antifungal agents, isotonic and absorption delaying agents, and the like, compatible with pharmaceutical administration. Materials that can serve as pharmaceutically acceptable carriers include, but are not limited to sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening agents, flavoring agents, and perfuming agents, preservatives, and antioxidants can be present in the composition, according to the judgment of the formulator (see also *Remington's Pharmaceutical Sciences*, Fifteenth Edition, E. W. Martin, Mack Publishing Co., Easton Pa., 1975). For example, the vaccine antigen product may be provided as a pharmaceutical composition by means of conventional mixing granulating dragee-making, dissolving, lyophilizing, or similar processes.

Additional Vaccine Components

Inventive vaccines may include additionally any suitable adjuvant to enhance the immunogenicity of the vaccine when administered to a subject. For example, such adjuvant(s) may include, without limitation, extracts of *Quillaja saponaria* (QS), including purified subfractions of food grade QS such as Quil A and QS-21, alum, aluminum hydroxide, aluminum phosphate, MF59, Malp2, incomplete Freund's adjuvant; Complete Freund's adjuvant; 3 De-O-acylated monophosphoryl lipid A (3D-MPL). Further adjuvants include immunomodulatory oligonucleotides, for example unmethylated CpG sequences as disclosed in WO 96/02555. Combinations of different adjuvants, such as those mentioned hereinabove, are contemplated as providing an adjuvant which is a preferential stimulator of TH1 cell response. For example, QS21 can be formulated together with 3D-MPL. The ratio of QS21: 3D-MPL will typically be in the order of 1:10 to 10:1; 1:5 to 5:1; and often substantially 1:1. A desired range for optimal synergy is 2.5:1 to 1:1 3D-MPL: QS21. Doses of purified QS extracts suitable for use in a human vaccine formulation are from 0.01 mg to 10 mg per kilogram of bodyweight.

It should be noted that certain thermostable proteins (e.g., lichenase) may themselves demonstrate immunoresponse potentiating activity, such that use of such protein whether in a fusion with an anthrax antigen or separately may be considered use of an adjuvant. Thus, inventive vaccine compositions may further comprise one or more adjuvants. Certain vaccine compositions may comprise two or more adjuvants. Furthermore, depending on formulation and routes of administration, certain adjuvants may be desired in particular formulations and/or combinations.

In certain situations, it may be desirable to prolong the effect of an inventive vaccine by slowing the absorption of one or more components of the vaccine product (e.g., protein) that is subcutaneously or intramuscularly injected. This may be accomplished by the use of a liquid suspension of crystalline or amorphous material with poor water solubility. The rate of absorption of the product then depends upon its rate of dissolution, which in turn, may depend upon size and form. Alternatively or additionally, delayed absorption of a parenterally administered product is accomplished by dissolving or suspending the product in an oil vehicle. Injectable depot forms are made by forming microcapsule matrices of the protein in biodegradable polymers such as polylactide-polyglycolide. Depending upon the ratio of product to polymer and the nature of the particular polymer employed, the rate of release can be controlled. Examples of biodegradable polymers include poly(orthoesters) and poly(anhydrides). Depot injectable formulations may be prepared by entrapping the product in liposomes or microemulsions, which are compatible with body tissues. Alternative polymeric delivery vehicles can be used for oral formulations. For example, biodegradable, biocompatible polymers such as ethylene vinyl acetate, polyanhydrides, polyglycolic acid, collagen, polyorthoesters, and polylactic acid, etc., can be used. Antigen(s) or an immunogenic portions thereof may be formulated as microparticles, e.g., in combination with a polymeric delivery vehicle.

Enterally administered preparations of vaccine antigens may be introduced in solid, semi-solid, suspension or emulsion form and may be compounded with any pharmaceutically acceptable carriers, such as water, suspending agents, and emulsifying agents. The antigens may be administered by means of pumps or sustained-release forms, especially when administered as a preventive measure, so as to prevent the development of disease in a subject or to ameliorate or delay an already established disease. Supplementary active compounds, e.g., compounds independently active against the disease or clinical condition to be treated, or compounds that enhance activity of an inventive compound, can be incorporated into or administered with the compositions. Flavorants and coloring agents can be used.

Inventive vaccine products, optionally together with plant tissue, are particularly well suited for oral administration as pharmaceutical compositions. Oral liquid formulations can be used and may be of particular utility for pediatric populations. Harvested plant material may be processed in any of a variety of ways (e.g., air drying, freeze drying, extraction etc.), depending on the properties of the desired therapeutic product and its desired form. Such compositions as described above may be ingested orally alone or ingested together with food or feed or a beverage. Compositions for oral administration include plants; extractions of the plants, and proteins purified from infected plants provided as dry powders, foodstuffs, aqueous or non-aqueous solvents, suspensions, or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medial parenteral vehicles including sodium chloride solution, Ringer's dextrose solution, dextrose plus sodium chloride solution, Ringer's solution containing lactose or fixed oils. Examples of dry powders include any plant biomass that has been dried, for example, freeze dried, air dried, or spray dried. For example, the plants may be air dried by placing them in a commercial air dryer at about 120 degrees Fahrenheit until the biomass contains less than 5% moisture by weight. The dried plants may be stored for further processing as bulk solids or further processed by grinding to a desired mesh sized powder. Alternatively or additionally, freeze-drying may be used for products that are sensitive to air-drying. Products may be freeze dried by placing them into a vacuum drier and dried frozen under a vacuum until the biomass contains less than about 5% moisture by weight. The dried material can be further processed as described herein.

Plant-derived material may be administered as or together with one or more herbal preparations. Useful herbal preparations include liquid and solid herbal preparations. Some examples of herbal preparations include tinctures, extracts (e.g., aqueous extracts, alcohol extracts), decoctions, dried preparations (e.g., air-dried, spray dried, frozen, or freeze-dried), powders (e.g., lyophilized powder), and liquid. Herbal preparations can be provided in any standard delivery vehicle, such as a capsule, tablet, suppository, liquid dosage, etc. Those skilled in the art will appreciate the various formulations and modalities of delivery of herbal preparations that may be applied to the present invention.

Inventive root lines, cell lines, plants, extractions, powders, dried preparations and purified protein or nucleic acid products, etc., can be in encapsulated form with or without one or more excipients as noted above. Solid dosage forms such as tablets, dragees, capsules, pills, and granules can be prepared with coatings and shells such as enteric coatings, release controlling coatings and other coatings well known in the pharmaceutical formulating art. In such solid dosage forms the active agent may be mixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally contain opacifying agents and can be of a composition that they release the active ingredient(s) only, or preferentially, in a certain part of the intestinal tract, and/or in a delayed manner. Examples of embedding compositions that can be used include polymeric substances and waxes.

In some methods, a plant or portion thereof expressing an anthrax antigen according to the present invention, or biomass thereof, is administered orally as medicinal food. Such edible compositions are typically consumed by eating raw, if in a solid form, or by drinking, if in liquid form. The plant material can be directly ingested without a prior processing step or after minimal culinary preparation. For example, the vaccine protein may be expressed in a sprout which can be eaten directly. For instance, vaccine antigens expressed in an alfalfa sprout, mung bean sprout, or spinach or lettuce leaf sprout, etc. In an alternative embodiment, plant biomass may be processed and the material recovered after the processing step is ingested.

Processing methods useful in accordance with the present invention are methods commonly used in the food or feed industry. The final products of such methods typically include a substantial amount of an expressed antigen and can be conveniently eaten or drunk. The final product may be mixed with other food or feed forms, such as salts, carriers, favor enhancers, antibiotics, and the like, and consumed in solid, semi-solid, suspension, emulsion, or liquid form. Such methods can include a conservation step, such as, e.g., pasteurization, cooking, or addition of conservation and preservation agents. Any plant may be used and processed in the present invention to produce edible or drinkable plant matter. The amount of anthrax antigen in a plant-derived preparation may be tested by methods standard in the art, e.g., gel electrophoresis, ELISA, or Western blot analysis, using a probe or antibody specific for the product. This determination may be used to standardize the amount of vaccine antigen protein ingested. For example, the amount of vaccine antigen may be determined and regulated, for example, by mixing batches of product having different levels of product so that the quantity of material to be drunk or eaten to ingest a single dose can be standardized. The contained, regulatable environment of the present invention, however, should minimize the need to carry out such standardization procedures.

A vaccine protein produced in a plant cell or tissue and eaten by a subject may be preferably absorbed by the digestive system. One advantage of the ingestion of plant tissue that has been only minimally processed is to provide encapsulation or sequestration of the protein in cells of the plant. Thus, the product may receive at least some protection from digestion in the upper digestive tract before reaching the gut or intestine and a higher proportion of active product would be available for uptake.

Pharmaceutical compositions of the present invention can be administered therapeutically or prophylactically. The compositions may be used to treat or prevent a disease. For example, any individual who suffers from a disease or who is at risk of developing a disease may be treated. It will be appreciated that an individual can be considered at risk for developing a disease without having been diagnosed with any symptoms of the disease. For example, if the individual is known to have been, or to be intended to be, in situations with relatively high risk of exposure to anthrax infection, that individual will be considered at risk for developing the disease. Similarly, if members of an individual's family or friends have been diagnosed with anthrax infection, the individual may be considered to be at risk for developing the disease.

Liquid dosage forms for oral administration include, but are not limited to, pharmaceutically acceptable emulsions, microemulsions, solutions, suspensions, syrups, and elixirs.

In addition to active agents, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents.

Compositions for rectal or vaginal administration may be suppositories or retention enemas, which can be prepared by mixing the compositions of this invention with suitable non-irritating excipients or carriers such as cocoa butter, polyethylene glycol or a suppository wax which are solid at ambient temperature but liquid at body temperature and therefore melt in the rectum or vaginal cavity and release the active protein.

Dosage forms for topical, transmucosal or transdermal administration of a vaccine composition of this invention include ointments, pastes, creams, lotions, gels, powders, solutions, sprays, inhalants or patches. The active agent, or preparation thereof, is admixed under sterile conditions with a pharmaceutically acceptable carrier and any needed preservatives or buffers as may be required. For transmucosal or transdermal administration, penetrants appropriate to the barrier to be permeated may be used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, antigen or an immunogenic portion thereof may be formulated into ointments, salves, gels, or creams as generally known in the art. Ophthalmic formulation, eardrops, and eye drops are contemplated as being within the scope of this invention. Additionally, the present invention contemplates the use of transdermal patches, which have the added advantage of providing controlled delivery of a vaccine protein to the body. Such dosage forms can be made by suspending or dispensing the vaccine product in the proper medium. Absorption enhancers can be used to increase the flux of the vaccine protein across the skin. The rate can be controlled by either providing a rate controlling membrane or by dispersing the vaccine protein in a polymer matrix or gel.

Inventive compositions are administered in such amounts and for such time as is necessary to achieve the desired result. In certain embodiments of the present invention a "therapeutically effective amount" of a pharmaceutical composition is that amount effective for treating, attenuating, or preventing a disease in a subject. Thus, the "amount effective to treat, attenuate, or prevent disease," as used herein, refers to a nontoxic but sufficient amount of the pharmaceutical composition to treat, attenuate, or prevent disease in any subject. For example, the "therapeutically effective amount" can be an amount to treat, attenuate, or prevent infection (e.g., bacterial infection, anthrax infection), etc.

The exact amount required may vary from subject to subject, depending on the species, age, and general condition of the subject, the stage of the disease, the particular pharmaceutical mixture, its mode of administration, and the like. Anthrax antigens of the invention, including plants expressing antigen(s) and/or preparations thereof may be formulated in dosage unit form for ease of administration and uniformity of dosage. The expression "dosage unit form," as used herein, refers to a physically discrete unit of vaccine composition appropriate for the patient to be treated. It will be understood, however, that the total daily usage of the compositions of the present invention is typically decided by an attending physician within the scope of sound medical judgment. The specific therapeutically effective dose level for any particular patient or organism may depend upon a variety of factors including the severity or risk of infection; the activity of the specific compound employed; the specific composition employed; the age, body weight, general health, sex of the patient, diet of the patient, pharmacokinetic condition of the patient, the time of administration, route of administration, and rate of excretion of the specific compound employed; the duration of the treatment; drugs used in combination or coincidental with the vaccine composition employed; and like factors well known in the medical arts.

It will be appreciated that vaccine compositions of the present invention can be employed in combination therapies (e.g., combination vaccine therapies), that is, the pharmaceutical compositions can be administered concurrently with, prior to, or subsequent to, one or more other desired pharmaceutical and/or vaccination procedures. The particular combination of therapies (e.g., vaccines, therapeutic treatment of anthrax infection) to employ in a combination regimen will generally take into account compatibility of the desired therapeutics and/or procedures and the desired therapeutic effect to be achieved. It will be appreciated that the therapies and/or vaccines employed may achieve a desired effect for the same disorder (for example, an inventive antigen may be administered concurrently with another anthrax vaccine), or they may achieve different effects.

In certain embodiments, vaccine compositions comprise at least two anthrax antigens. For example, certain vaccine compositions can comprise at least two anthrax antigens of the invention (e.g., a PA domain and an LF domain containing antigen of the invention). In some aspects such combination vaccines may include one thermostable fusion protein comprising anthrax antigen; in some aspects, two or more thermostable fusion proteins comprising anthrax antigen are provided. Where combination vaccines are utilized, it will be understood that any combination of anthrax antigens may be used for such combinations.

Kits

In one aspect, the present invention provides a pharmaceutical pack or kit including live sprouted seedlings, clonal entity or plant producing an anthrax antigen according to the present invention, or preparations, extracts, or pharmaceutical compositions containing the vaccine in one or more containers filled with one or more of the ingredients of the pharmaceutical compositions of the invention. In certain embodiments, the pharmaceutical pack or kit includes an additional approved therapeutic agent (e.g., anthrax antigen, anthrax vaccine) for use as a combination therapy. Optionally associated with such container(s) can be a notice in the form prescribed by a governmental agency regulating the manufacture, use or sale of pharmaceutical products, which notice reflects approval by the agency of manufacture, use, or sale for human administration.

Kits are provided that include therapeutic reagents. As but one non-limiting example, anthrax vaccine can be provided as oral formulations and administered as therapy. Alternatively or additionally, anthrax vaccine can be provided in an injectable formulation for administration. Pharmaceutical doses or instructions therefore may be provided in the kit for administration to an individual suffering from or at risk for anthrax infection.

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain information, exemplification and guidance, which can be adapted to the practice of this invention in its various embodiments and the equivalents thereof.

Exemplification

EXAMPLE 1

Generation of Vaccine Candidate Constructs

Generation of Antigen Sequences from B. anthracis

Nucleotide sequence encoding 148 amino acids (residues 617 to 764) of domain four of B. anthracis PA was synthesized and confirmed as being correct. Produced nucleic acid was digested with restriction endonucleases BglII and HindIII, sites for which had been engineered onto either end of sequence encoding domain four. The resulting DNA fragment was fused in frame to sequence encoding an engineered thermostable carrier molecule.

Nucleotide and amino acid sequence of domain 4 of PA (amino acid residues 592-731 of the mature PA polypeptide, SEQ ID NO.: 3; SEQ ID NO.: 4, respectively).

SEQ ID NO.: 3:
AGATCTAGAGATAAGAGATTTCATTATGATAGAAACAACATTGCTGTTGG

AGCTGATGAATCTGTTGTTAAGGAGGCTCATAGAGAGGTTATTAACTCTT

CTACTGAGGGACTTTTGCTTAACATTGATAAGGATATTAGAAAGATTCTT

TCTGGATATATTGTTGAGATTGAGGATACTGAGGGACTTAAGGAGGTTAT

TAACGATAGATATGATATGCTTAACATTTCTTCTCTTAGACAAGATGGAA

AGACTTTTATTGATTTTAAGAAGTATAACGATAAGTTGCCACTTTATATT

TCTAACCCAAACTATAAGGTTAACGTTTATGCTGTTACTAAGGAGAACAC

TATTATTAACCCATCTGAGAACGGAGATACTTCTACTAACGGTATTAAGA

AGATTCTTATTTTCTCTAAGAAGGGAAAGCTT

SEQ ID NO.: 4:
RDKRFHYDRNNIAVGADESVVKEAHREVINSSTEGLLLNIDKDIRKILSG

YIVEIEDTEGLKEVINDRYDMLNISSLRQDGKTFIDFKKYNDKLPLYISN

PNYKVNVYAVTKENTIINPSENGDTSTNGIKKILIFSKKG

Nucleotide sequence encoding N terminal 220 amino acids of B. anthracis LF (amino acids 1-254) was synthesized and confirmed as being correct. Produced nucleic acid was digested with restriction endonucleases BglII and HindIII, sites for which had been engineered onto either end of the coding sequence. The resulting DNA fragment was fused in frame to sequence encoding an engineered thermostable carrier molecule.

Optimized nucleotide and amino acid sequences of N terminal domain (residues 1-254 of the mature protein sequence of LF, GenBank accession number M29081; SEQ ID NO.: 5, SEQ ID NO.: 6, respectively).

SEQ ID NO.: 5:
AGATCTGCTGGAGGTCATGGAGATGTTGGAATGCATGTTAAGGAGAAGGA

GAAGAACAAGGATGAGAACAAGAGAAAGGATGAGGAGAGAAACAAGACTC

AAGAGGAGCATCTTAAGGAGATTATGAAGCATATTGTTAAGATTGAAGTT

AAGGGAGAAGAGGCTGTTAAGAAGGAAGCTGCAGAGAAGTTGCTTGAAAA

GGTTCCATCTGATGTTCTTGAGATGTATAAGGCTATTGGAGGAAAGATAT

ATATTGTTGATGGAGATATTACTAAGCATATTTCTCTTGAGGCTCTTTCT

GAGGATAAGAAGAAGATTAAGGATATATATGGAAAGGATGCTCTTTTGCA

TGAGCATTATGTTTATGCTAAGGAGGGATATGAGCCAGTTCTTGTTATTC

AATCTTCTGAAGATTATGTTGAGAACACTGAGAAGGCTCTTAACGTTTAT

TATGAGATTGGAAAGATTCTTTCTAGAGATATTCTTTCTAAGATTAACCA

ACCATATCAAAAGTTTCTTGATGTTCTTAACACTATTAAGAACGCTTCTG

ATTCTGATGGACAAGATTTGTTGTTTACTAACCAACTTAAGGAGCATCCA

ACTGATTTTTCTGTTGAGTTTCTTGAGCAAAACTCTAATGAGGTTCAAGA

GGTTTTTGCTAAGGCTTTTGCTTATTATATTGAGCCACAACATAGAGATG

TTCTTCAACTTTATGCTCCAGAGGCATTCAACTATATGGATAAGTTTAAC

GAGCAAGAGATTAACCTTAAGCTT

SEQ ID NO.: 6:
AGGHGDVGMHVKEKEKNKDENKRKDEERNKTQEEHLKEIMKHIVKIEVKG

EEAVKKEAAEKLLEKVPSDVLEMYKAIGGKIYIVDGDITKHISLEALSED

KKKIKDIYGKDALLHEHYVYAKEGYEPVLVIQSSEDYVENTEKALNVYYE

IGKILSRDILSKINQPYQKFLDVLNTIKNASDSDGQDLLFTNQLKEHPTD

FSVEFLEQNSNEVQEVFAKAFAYYIEPQHRDVLQLYAPEAFNYMDKFNEQ

EINL

Generation of Thermostable Carrier Construct

Full length native C. thermocellum lichenase, LicB, consists sequentially of a leader peptide (Lp), an N-terminal portion (A), a surface loop (l), a C-terminal portion (C), a Pro-Thr box, and a cellulosome-binding domain (C-BD). We removed the Lp, Pro-Thr box and C-BD encoding sequences from the LicB encoding gene, circularly permutated the molecule to invert the N- and C-termini (Musiychuk et al., 2007, Influenza and Other Respiratory Viruses, 1:1), and incorporated unique restriction endonuclease sites for cloning target sequences at the N- and C-termini as well as into the surface loop (l). The resulting engineered carrier molecule sequence was verified, and is designated LicKM.

SEQ ID NO.: 7:
GGATCCTTAATTAAAATGGGAGGTTCTTATCCATATAAGTCTGGTGAGTA

TAGAACTAAGTCTTTCTTTGGATATGGTTATTATGAAGTTAGGATGAAGG

CTGCAAAGAACGTTGGAATTGTTTCTTCTTTCTTTACTTATACTGGACCA

TCTGATAACAACCCATGGGATGAGATTGATATTGAGTTTCTTGGAAAGGA

TACTACTAAGGTTCAATTCAACTGGTATAAGAATGGTGTTGGTGGAAACG

AGTATCTTCATAACCTTGGATTTGATGCTTCTCAAGATTTTCATACTTAT

GGTTTTGAGTGGAGACCAGATTATATTGATTTTTATGTTGATGGAAAGAA

GGTTTATAGAGGTACTAGAAACATTCCAGTTACTCCTGGAAAGATTATGA

-continued

TGAATCTTTGGCCAGGAATTGGTGTTGATGAATGGCTTGGTAGATATGAT

GGAAGAACTCCACTTCAAGCTGAGTATGAGTATGTTAAGTATTATCCAAA

CGGTAGATCTGAATTCAAGCTTGTTGTTAATACTCCATTTGTTGCTGTTT

TCTCTAACTTTGATTCTTCTCAATGGGAAAAGGCTGATTGGGCTAACGGT

TCTGTTTTTAACTGTGTTTGGAAGCCATCTCAAGTTACTTTTTCTAACGG

AAAGATGATTCTTACTTTGGATAGAGAGTATGTCGACCATCATCATCATC

ATCATTGACTCGAGCTC

SEQ ID NO.: 8:
MGGSYPYKSGEYRTKSFFGYGYYEVRMKAAKNVGIVSSFFTYTGPSDNNP

WDEIDIEFLGKDTTKVQFNWYKNGVGGNEYLHNLGFDASQDFHTYGFEWR

PDYIDFYVDGKKVYRGTRNIPVTPGKIMMNLWPGIGVDEWLGRYDGRTPL

QAEYEYVKYYPNGRSEFKLVVNTPFVAVFSNFDSSQWEKADWANGSVFNC

VWKPSQVTFSNGKMILTLDREYVDHHHHHH

For certain constructs, we engineered a PR1a signal peptide and KDEL sequence at the N- and C-termini of LicKM. The nucleic acid and amino acid sequences of these constructs are shown in SEQ ID NO.: 9 and SEQ ID NO.: 10.

SEQ ID NO.: 9:
GGATCCTTAATTAAAATGGGATTTGTTCTCTTTTCACAATTGCCTTCATT

TCTTCTTGTCTCTACACTTCTCTTATTCCTAGTAATATCCCACTCTTGCC

GTGCCCAAAATGGAGGTTCTTATCCATATAAGTCTGGTGAGTATAGAACT

AAGTCTTTCTTTGGATATGGTTATTATGAAGTTAGGATGAAGGCTGCAAA

GAACGTTGGAATTGTTTCTTCTTTCTTTACTTATACTGGACCATCTGATA

ACAACCCATGGGATGAGATTGATATTGAGTTTCTTGGAAAGGATACTACT

AAGGTTCAATTCAACTGGTATAAGAATGGTGTTGGTGGAAACGAGTATCT

TCATAACCTTGGATTTGATGCTTCTCAAGATTTTCATACTTATGGTTTTG

AGTGGAGACCAGATTATATTGATTTTTATGTTGATGGAAAGAAGGTTTAT

AGAGGTACTAGAAACATTCCAGTTACTCCTGGAAAGATTATGATGAATCT

TTGGCCAGGAATTGGTGTTGATGAATGGCTTGGTAGATATGATGGAAGAA

CTCCACTTCAAGCTGAGTATGAGTATGTTAAGTATTATCCAAACGGTAGA

TCTGAATTCAAGCTTGTTGTTAATACTCCATTTGTTGCTGTTTTCTCTAA

CTTTGATTCTTCTCAATGGGAAAAGGCTGATTGGGCTAACGGTTCTGTTT

TTAACTGTGTTTGGAAGCCATCTCAAGTTACTTTTTCTAACGGAAAGATG

ATTCTTACTTTGGATAGAGAGTATGTCGACCATCATCATCATCATCATAA

GGATGAACTTTGACTCGAGCTC

SEQ ID NO.: 10:
MGFVLFSQLPSFLLVSTLLLFLVISHSCRAQNGGSYPYKSGEYRTKSFFG

YGYYEVRMKAAKNVGIVSSFFTYTGPSDNNPWDEIDIEFLGKDTTKVQFN

WYKNGVGGNEYLHNLGFDASQDFHTYGFEWRPDYIDFYVDGKKVYRGTRN

IPVTPGKIMMNLWPGIGVDEWLGRYDGRTPLQAEYEYVKYYPNGRSEFKL

VVNTPFVAVFSNFDSSQWEKADWANGSVFNCVWKPSQVTFSNGKMILTLD

REYVDHHHHHHKDEL

Generation of Recombinant Antigen Constructs

The DNA fragment encoding domain four of *B. anthracis* PA was subcloned into the loop (l) portion of LicKM to give a fusion, LicKM-PAD4, in the correct reading frame for translation. The nucleotide and protein sequences for the generated constructs are provided in SEQ ID NO.: 11 and 12, respectively. Similarly, the DNA fragment encoding the N-terminal domain of *B. anthracis* LF was subcloned into the loop (l) portion of LicKM to give a fusion, LicKM-LF, in the correct reading frame for translation. The nucleotide and protein sequences for the generated constructs are provided in SEQ ID NO.: 13 and 14, respectively.

SEQ ID NO.: 11:
GGATCCTTAATTAAAATGGGATTTGTTCTCTTTTCACAATTGCCTTCATT

TCTTCTTGTCTCTACACTTCTCTTATTCCTAGTAATATCCCACTCTTGCC

GTGCCCAAAATGGAGGTTCTTATCCATATAAGTCTGGTGAGTATAGAACT

AAGTCTTTCTTTGGATATGGTTATTATGAAGTTAGGATGAAGGCTGCAAA

GAACGTTGGAATTGTTTCTTCTTTCTTTACTTATACTGGACCATCTGATA

ACAACCCATGGGATGAGATTGATATTGAGTTTCTTGGAAAGGATACTACT

AAGGTTCAATTCAACTGGTATAAGAATGGTGTTGGTGGAAACGAGTATCT

TCATAACCTTGGATTTGATGCTTCTCAAGATTTTCATACTTATGGTTTTG

AGTGGAGACCAGATTATATTGATTTTTATGTTGATGGAAAGAAGGTTTAT

AGAGGTACTAGAAACATTCCAGTTACTCCTGGAAAGATTATGATGAATCT

TTGGCCAGGAATTGGTGTTGATGAATGGCTTGGTAGATATGATGGAAGAA

CTCCACTTCAAGCTGAGTATGAGTATGTTAAGTATTATCCAAACGGTAGA

TCTAGAGATAAGAGATTTCATTATGATAGAAACAACATTGCTGTTGGAGC

TGATGAATCTGTTGTTAAGGAGGCTCATAGAGAGGTTATTAACTCTTCTA

CTGAGGGACTTTTGCTTAACATTGATAAGGATATTAGAAAGATTCTTTCT

GGATATATTGTTGAGATTGAGGATACTGAGGGACTTAAGGAGGTTATTAA

CGATAGATATGATATGCTTAACATTTCTTCTCTTAGACAAGATGGAAAGA

CTTTTATTGATTTTAAGAAGTATAACGATAAGTTGCCACTTTATATTTCT

AACCCAAACTATAAGGTTAACGTTTATGCTGTTACTAAGGAGAACACTAT

TATTAACCCATCTGAGAACGGAGATACTTCTACTAACGGTATTAAGAAGA

TTCTTATTTTCTCTAAGAAGGGAAAGCTTGTTGTTAATACTCCATTTGTT

GCTGTTTTCTCTAACTTTGATTCTTCTCAATGGGAAAAGGCTGATTGGGC

TAACGGTTCTGTTTTTAACTGTGTTTGGAAGCCATCTCAAGTTACTTTTT

CTAACGGAAAGATGATTCTTACTTTGGATAGAGAGTATGTCGACCATCAT

CATCATCATCATAAGGATGAACTTTGACTCGAGCTC

SEQ ID NO.: 12:
MGFVLFSQLPSFLLVSTLLLFLVISHSCRAQNGGSYPYKSGEYRTKSFFG

YGYYEVRMKAAKNVGIVSSFFTYTGPSDNNPWDEIDIEFLGKDTTKVQFN

WYKNGVGGNEYLHNLGFDASQDFHTYGFEWRPDYIDFYVDGKKVYRGTRN

IPVTPGKIMMNLWPGIGVDEWLGRYDGRTPLQAEYEYVKYYPNGRSRDKR

FHYDRNNIAVGADESVVKEAHREVINSSTEGLLLNIDKDIRKILSGYIVE

IEDTEGLKEVINDRYDMLNISSLRQDGKTFIDFKKYNDKLPLYISNPNYK

```
-continued
VNVYAVTKENTIINPSENGDTSTNGIKKILIFSKKGKLVVNTPFVAVFSN

FDSSQWEKADWANGSVFNCVWKPSQVTFSNGKMILTLDREYVDHHHHHHK

DEL

SEQ ID NO.: 13:
GGATCCTTAATTAAAATGGGAGGTTCTTATCCATATAAGTCTGGTGAGTA

TAGAACTAAGTCTTTCTTTGGATATGGTTATTATGAAGTTAGGATGAAGG

CTGCAAAGAACGTTGGAATTGTTTCTTCTTTCTTTACTTATACTGGACCA

TCTGATAACAACCCATGGGATGAGATTGATATTGAGTTTCTTGGAAAGGA

TACTACTAAGGTTCAATTCAACTGGTATAAGAATGGTGTTGGTGGAAACG

AGTATCTTCATAACCTTGGATTTGATGCTTCTCAAGATTTTCATACTTAT

GGTTTTGAGTGGAGACCAGATTATATTGATTTTTATGTTGATGGAAAGAA

GGTTTATAGAGGTACTAGAAACATTCCAGTTACTCCTGGAAAGATTATGA

TGAATCTTTGGCCAGGAATTGGTGTTGATGAATGGCTTGGTAGATATGAT

GGAAGAACTCCACTTCAAGCTGAGTATGAGTATGTTAAGTATTATCCAAA

CGGTAGATCTGCTGGAGGTCATGGAGATGTTGGAATGCATGTTAAGGAGA

AGGAGAAGAACAAGGATGAGAACAAGAGAAAGGATGAGGAGAGAAACAAG

ACTCAAGAGGAGCATCTTAAGGAGATTATGAAGCATATTGTTAAGATTGA

AGTTAAGGGAGAAGAGGCTGTTAAGAAGGAAGCTGCAGAGAAGTTGCTTG

AAAAGGTTCCATCTGATGTTCTTGAGATGTATAAGGCTATTGGAGGAAAG

ATATATATTGTTGATGGAGATATTACTAAGCATATTTCTCTTGAGGCTCT

TTCTGAGGATAAGAAGAAGATTAAGGATATATATGGAAAGGATGCTCTTT

TGCATGAGCATTATGTTTATGCTAAGGAGGGATATGAGCCAGTTCTTGTT

ATTCAATCTTCTGAAGATTATGTTGAGAACACTGAGAAGGCTCTTAACGT

TTATTATGAGATTGGAAAGATTCTTTCTAGAGATATTCTTTCTAAGATTA

ACCAACCATATCAAAAGTTTCTTGATGTTCTTAACACTATTAAGAACGCT

TCTGATTCTGATGGACAAGATTTGTTGTTTACTAACCAACTTAAGGAGCA

TCCAACTGATTTTTCTGTTGAGTTTCTTGAGCAAAACTCTAATGAGGTTC

AAGAGGTTTTTGCTAAGGCTTTTGCTTATTATATTGAGCCACAACATAGA

GATGTTCTTCAACTTTATGCTCCAGAGGCATTCAACTATATGGATAAGTT

TAACGAGCAAGAGATTAACCTTAAGCTTGTTGTTAATACTCCATTTGTTG

CTGTTTTCTCTAACTTTGATTCTTCTCAATGGGAAAAGGCTGATTGGGCT

AACGGTTCTGTTTTTAACTGTGTTTGGAAGCCATCTCAAGTTACTTTTTC

TAACGGAAAGATGATTCTTACTTTGGATAGAGAGTATGTCGACCATCATC

ATCATCATCATTGACTCGAGCTC

SEQ ID NO.: 14:
MGGSYPYKSGEYRTKSFFGYGYYEVRMKAAKNVGIVSSFFTYTGPSDNNP

WDEIDIEFLGKDTTKVQFNWYKNGVGGNEYLHNLGFDASQDFHTYGFEWR

PDYIDFYVDGKKVYRGTRNIPVTPGKIMMNLWPGIGVDEWLGRYDGRTPL

QAEYEYVKYYPNGRSAGGHGDVGMHVKEKEKNKDENKRKDEERNKTQEEH

LKEIMKHIVKIEVKGEEAVKKEAAEKLLEKVPSDVLEMYKAIGGKIYIVD

GDITKHISLEALSEDKKKIKDIYGKDALLHEHYVYAKEGYEPVLVIQSSE

DYVENTEKALNVYYEIGKILSRDILSKINQPYQKFLDVLNTIKNASDSDG

QDLLFTNQLKEHPTDFSVEFLEQNSNEVQEVFAKAFAYYIEPQHRDVLQL

YAPEAFNYMDKFNEQEINLKLVVNTPFVAVFSNFDSSQWEKADWANGSVF

NCVWKPSQVTFSNGKMILTLDREYVDHHHHHH
```

EXAMPLE 2

Generation of Vaccine Candidate Antigen Vectors

Figure 2:
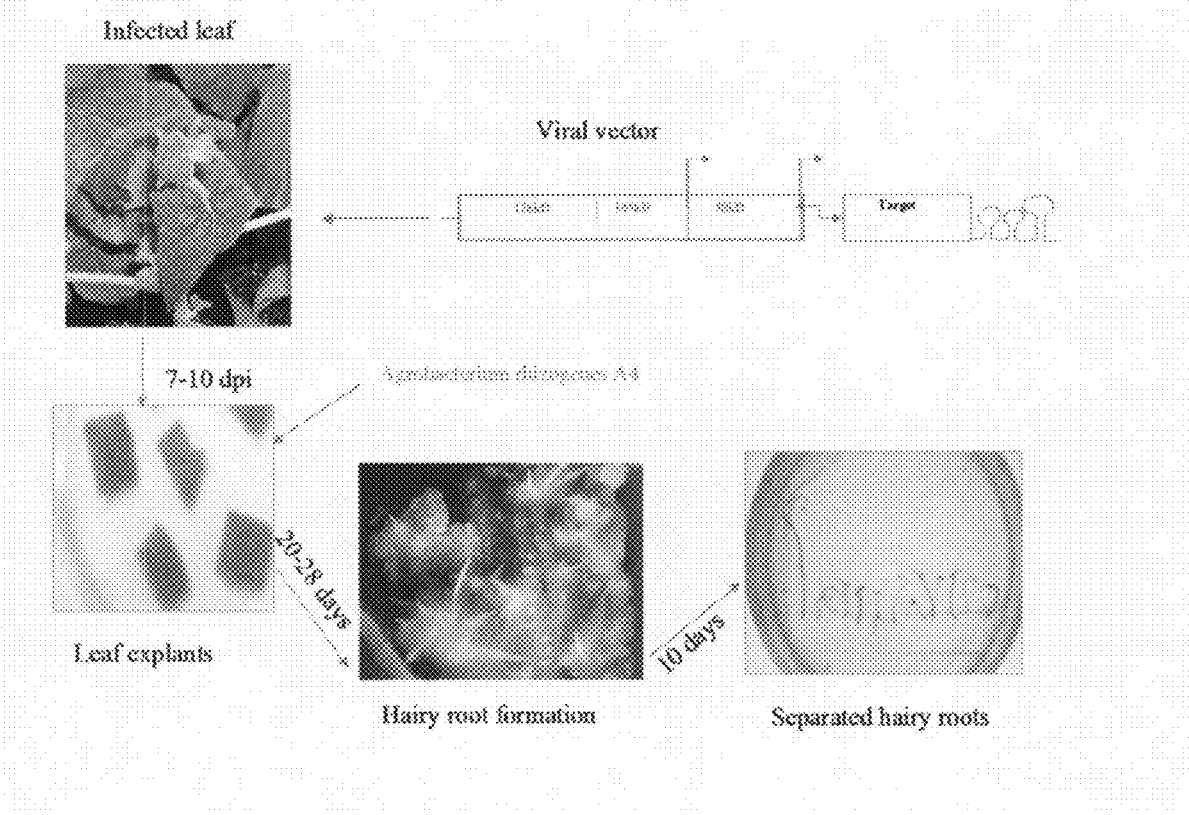
FIG. 2. Expression constructs and steps of infusion followed by *A. rhizogenes* infection and production of hairy roots. Seven to ten days post-inoculation, leaves infected with virus were harvested and subjected to infection with *A. rhizogenes* strain A4. dpi=days post-inoculation.

Target antigen constructs LicKM-PAD4 or LicKM-LF were individually subcloned into the chosen viral vector (D4). D4 is a TMV-based construct in which a foreign gene to be expressed (e.g., target antigen (e.g., LicKM-PAD4)) replaces the coat protein (CP) gene of TMV. The virus retains the TMV 126/183 kDa gene, the movement protein (MP) gene, and the CP subgenomic mRNA promoter (sgp), which extends into the CP open reading frame (ORF). The start codon for CP has been mutated. The virus lacks CP and therefore cannot move throughout the host plant via phloem. However, cell-to-cell movement of viral infection remains functional, and the virus can move slowly to the upper leaves in this manner. A multiple cloning site (PacI-PmeI-AgeI-XhoI) has been engineered at the end of sgp for expression of foreign genes, and is followed by the TMV 3' non-translated region (NTR). The T7 RNA polymerase promoter is fused to the 5' NTR to make in vitro transcripts for plant inoculation. A KpnI site at the 3' end can be used to linearize the vector for in vitro transcription. For constructs that contain sequence encoding LicKM, LicKM-PAD4, or LicKM-LF, the coding DNA was introduced as PacI-XhoI fragments into D4. Nucleotide sequence was subsequently verified spanning the subcloning junctions of the final expression constructs (FIG. 2).

EXAMPLE 3

Generation of Plants and Antigen Production

Clonal Root and Clonal Root Line Generation

Generation of clonal roots and clonal root lines is depicted in FIG. 11. Fully expended leaves of *P. hybrida* grown in greenhouse were surface sterilized for 6 minutes with 10% bleach (Clorox®) and washed several times with sterile distilled water. Surface sterilized leaves were cut into 1 cm² pieces. They were placed on a surface of preculture medium which is sucrose-free MS (Murashige et al., 1962, *Physiologia Plantarum* 15:473) medium with 1 mg/l of NAA (naphthalene acetic acid) and 0.2 mg/l of BA (benzyl adenine) and 0.8% of agar. Leaf pieces were kept on preculture medium for 4-5 days. *A. rhizogenes* strain A4 with the engineered pBID4 expressing PAD4 was grown to an $OD_{600}$ of 0.8-1. Bacterial cells were pelleted and resuspended in MS-1 medium (MS salts, 1% glucose, 10 mM MES, pH 5.5) to a final $OD_{600}$ of 0.1. In order to induce virulence in the bacterium, acetosyringone hormone was added to final concentration 200 μM at 1 hour before transformation. Leaf pieces were submerged into bacterial suspension for 5 minutes, drained on filter paper and placed on the surface of coculture MS medium with 1 mg/l of NAA, 0.2 mg/l of BA, 1% glucose, 200 μM of acetosyringone and 0.8% of agar. Plates were kept in dim light conditions at 20-22° C. for 48 hours. Next, leaf explants were washed in liquid hormone-free MS medium with 500 mg/l of Cefotaxime and 100 mg/l of Timentine for 1 hour on a rotary shaker (50 rpm) at room temperature. Excess of liquid was then removed and leaf explants placed on solid, hormone free, MS medium with 25 mg/l of kanamycin, 500 mg/l of Cefotaxime and 100 mg/l of Timentine. Plates were kept at 25° C. on a 16 hour day/8 hour night light regimen to induce hairy roots.

Four to five weeks after transformation, hairy roots were cut off and placed in a line on solid, hormone free $K_3$ (see Kao et al., 1974, *Planta*, 115:355; modified according to Maliga et al., 1976, *Mol. Gen. Genet.*, 149:267 and Menczel et al., 1981, *Theor. Appl. Genet.*, 59:191) medium supplemented with the antibiotics mentioned above. Six to ten days later the most actively growing roots were isolated and transferred to semi-solid (0.4% of agar) $K_3$ medium with antibiotics. Selected roots were cultured at 20-22° C. in the dark and clonal lines were isolated and subcultured each 6 weeks. Roots and/or clonal lines were screened for the presence of target antigen expression by assessment of lichenase activity assay and immunoblot analysis, as described below.

The producer lines were examined by immunoblot analysis. Two clonal root lines expressing LicKM and LicKM-PAD4 were selected for assessment. For both lines, levels of target antigen accumulation was maintained throughout sub-culturing (LicKM-17 mg/kg and LicKM-PAD 4-5.0 mg/kg). When the same constructs were similarly tested in greenhouse plants (*N. benthamiana*) which had been infected with the same constructs however, the genetic stability was significantly lower, such that during second or third passage up to 80% of the viral vector lost the antigen insert.

In an alternative method of generating clonal roots and/or clonal root lines, in vitro transcripts are synthesized from the expression vectors using T7 or other RNA polymerase after KpnI linearization. Specifically, approximately 10 μg of DNA is linearized with 30 units of KpnI overnight in a reaction volume of 100 μl. From the restriction endonuclease digest, 4 μl is used to produce in vitro transcripts using the AmpliCap T7 High Yield message Maker Kit (Epicentre) according the manufacturer's recommendations. Transcripts from one such reaction are used to infect 12 six-week-old *Petunia hybrida* plants. Plants are inoculated by manually applying the transcripts dissolved FES buffer (0.1 M glycine, 0.06 M potassium phosphate, 1% w/v sodium pyrophosphate, 1% w/v macaloid, 1% w/v celite, pH 8.5) onto young, fully expanded leaves.

Next, plant tissue is infected with *Agrobacterium* in order to induce hairy root formation. For example, local or systemically infected leaves of *P. hybrida* are harvested 7-10 days after inoculation with viral transcript. Leaves are surface sterilized for 6 minutes with 10% bleach (Clorox®) and washed several times with sterile distilled water. *A. rhizogenes* strain A4 is grown to an $OD_{600}$ of 0.8-1. Bacterial cells are pelleted and resuspended in MS-2 medium (MS salts, 2% sucrose, 10 mM MES, pH 5.5) to a final $OD_{600}$ of 0.5 (Murashige et al., 1962, *Physiologia Plantarum* 15:473). In order to induce virulence in the bacterium, acetosyringone is added to final concentration 200 μM at 1 hour before transformation. Surface sterilized leaves are cut into 1 cm² pieces. They are submerged into bacterial suspension for 5 minutes, drained on filter paper and placed on the surface of solidified MS-2 medium. Plates are kept in dim light conditions at 24° C. for 48 hours. Excess *Agrobacterium* is then removed and leaf explants placed on solid, hormone free, $K_3$ medium (see Kao et al., 1974, *Planta*, 115:355; modified according to Maliga et al., 1976, *Mol. Gen. Genet.*, 149:267 and Menczel et al., 1981, *Theor. Appl. Genet.*, 59:191). Plates are kept at 25° C. on a 16 hour day/8 hour night light regimen to induce hairy roots.

Three weeks after transformation, hairy roots are cut off and placed in a line on solid, hormone free $K_3$ medium. Four to six days later the most actively growing roots are isolated and transferred to liquid $K_3$ medium. Selected roots are cultured on a rotary shaker at 24° C. in the dark and clonal lines are isolated and subcultured weekly. Roots and/or clonal lines are screened for the presence of target antigen expression by assessment of lichenase activity assay and immunoblot analysis, as described below.

*Agrobacterium* Infiltration of Plants

An alternative expression strategy can be used to generate antigens in plants. For example, an *Agrobacterium*-mediated transient expression system achieved by *Agrobacterium* infiltration can be utilized. Healthy leaves of *N. benthamiana* were infiltrated with *A. rhizogenes* containing viral vectors engineered to express LicKM or LicKM-PAD4. The vector used was pBI-D4, a version of the viral expression vector D4 introduced into the *Agrobacterium* vector pBI121. (Chen et al., 2003, *Mol. Breed.*, 11:287). The 35S promoter is fused at the 5' end of the viral sequence. The vector sequence is positioned between the BamHI and SacI sites of pBI121. The hammerhead ribozyme is placed 3' of the viral sequence (Turpen et al., 1993, *J. Virol. Methods*, 42:227). These constructs include fusions of sequences encoding LicKM-PAD4 or LicKM, to sequences encoding the signal peptide from tobacco PR-1a protein, a 6× His tag and the ER-retention anchor sequence KDEL (see SEQ ID NO.: 10).

The *A. rhizogenes* strain A4 (ATCC 43057) was transformed with the constructs pBI-D4-PRLicKM-PAD4K and pBI-D4-PRLicKMK. *Agrobacterium* cultures were grown and induced as described (Kapila et al., 1997, *Plant Sci.*, 122:101). A 2 ml starter-culture (picked from a fresh colony) was grown overnight in YEB (5 g/l beef extract, 1 g/l yeast extract, 5 g/l peptone, 5 g/l sucrose, 2 mM $MgSO_4$) with 25 μg/ml kanamycin at 28° C. The starter culture was diluted 1:500 into 500 ml of YEB with 25 μg/ml kanamycin, 10 mM 2-4(-morpholino)ethanesulfonic acid (MES) pH 5.6, 2 mM additional $MgSO_4$ and 20 μM acetosyringone. The diluted culture was then grown overnight to an $O.D._{600}$ of ~1.7 at 28° C. The cells were centrifuged at 3,000×g for 15 minutes and re-suspended in MMA medium (MS salts, 10 mM MES pH 5.6, 20 g/l sucrose, 200 μM acetosyringone) to an $O.D._{600}$ of 2.4, kept for 1 hour at room temperature, and used for *Agrobacterium*-infiltration. *N. benthamiana* leaves were injected with the *Agrobacterium*-suspension using a disposable syringe without a needle. Infiltrated leaves were harvested 6 days post-infiltration.

EXAMPLE 4

Production of Vaccine Candidate

Antigen Production Scale-Up

Figures 3, 4:
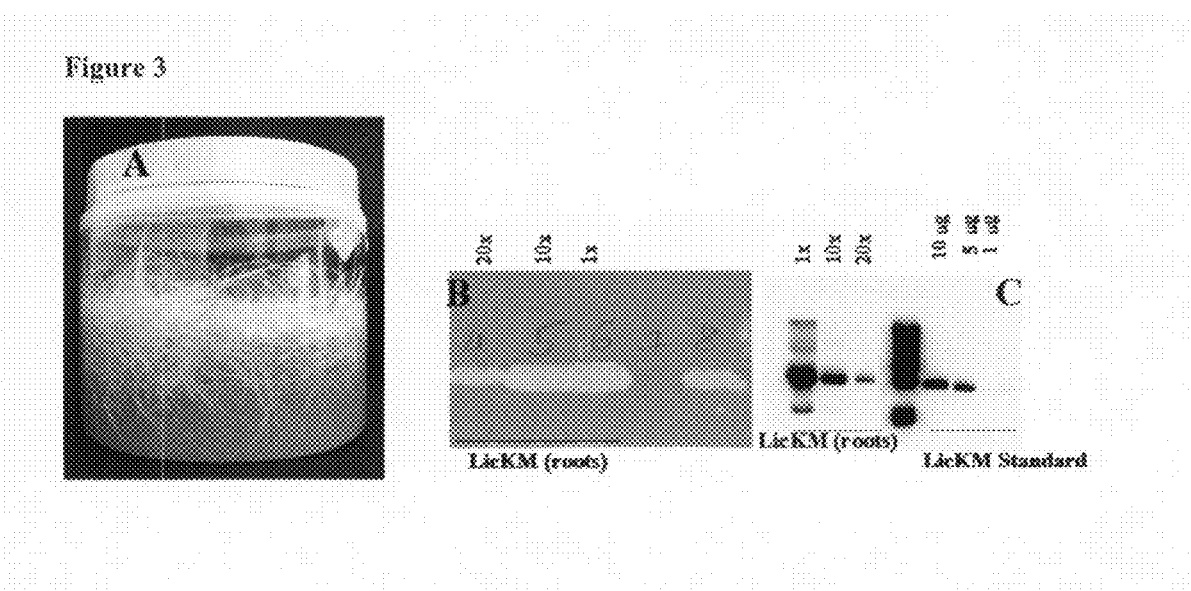
FIG. 3. (3A) Scale-up of selected root lines. (3B) Zymogram of lichenase activity in root material. (3C) Western analysis of plant produced LicKM. Immunoblot of lichenase in root material using a lichenase specific rabbit polyclonal antibody. (3B,C) 20× dilution, 10× dilution, and undiluted root material is shown alongside *E. coli*-produced recombinant lichenase standard.
FIG. 4. Anthrax PA-specific serum antibody (IgG) response of mice immunized intraperitoneally with LicKM-PAD4 or LicKM. Serum samples from each animal were plated individually. Optical readings were at 460 nm.

Individual root lines that demonstrated high levels of target protein accumulation were maintained in Magenta boxes on a modified K3 medium (Kao et al., 1974, *Planta*, 115:355) with 0.35% agar in the dark at 25° C. and sub-cultured every 45 days in sterile-contained conditions. To scale-up production of selected root lines they were cultured on K3 medium in 2 L medicinal jars (FIG. 3, panel A). Hormone-free K3 medium was identified as optimal for clonal root growth. The root biomass increased approximately 10-15 fold in a six week period. For LicKM (placebo) production in the batch produced for the Phase I clinical trial, roots were assessed using both an enzymatic assay (FIG. 3, panel B) and a Western blot (FIG. 3, panel C).

Fresh roots were collected from *P. hybrida* root culture expressing LicKM-PAD4, and tissue was lyophilized and stored at −75° C. Placebo material from root cultures expressing LicKM was prepared and stored in the same fashion. A single lot of test material and a single lot of placebo material were prepared.

Capsule Generation

Test material and placebo material from *P. hybrida* root cultures were formulated into capsules. The target antigen (LicKM-PAD4) and placebo carrier (LicKM) were incorporated into test and placebo capsules, respectively, at 0.25 mg target antigen/capsule. To more accurately dispense and fill capsules, a blend of microcrystalline cellulose (MCC) and protein extract was uniformly mixed prior to encapsulation. For both the vaccine candidate and placebo, a container was filled with 120 capsules. Weight variation of filled capsules was monitored and did not exceed 10%. Capsules were coated with an enteric polymer system for release in the small intestine. This coating is a solvent-based, acrylic acid/acrylate blend for release above pH 6.0. Capsules were prepared by Emerson Pharma Services (Norristown, Pa., USA).

Purification of Antigens

Partially purified LicKM-PAD4 and LicKM were prepared from *Agrobacterium* infiltrated leaves of *N. benthamiana*, and/or separately, from root cultures of *P. hybrida* carrying the viral vector, described above.

Approximately 100 g of *N. benthamiana* leaves freshly infiltrated with Agrobacteria, or approximately 100 g of *P. hybrida* roots harvested from culture were blended in 300 ml of extraction buffer (50 mM phosphate buffer pH 7.0, 100 mM NaCl, 10 mM Dieca [diethyldithiocarbamic acid], 10 mM β-mecaptoethanol). Resulting extract was centrifuged at 20,000 rpm for 20 minutes, and the supernatant was filtered through Mira cloth, then centrifuged again at 25,000 rpm for another 30 minutes. $(NH_4)_2SO_4$ was added very slowly to the supernatant to a point of 20% saturation, and the solution was incubated on ice for 1 hour and centrifuged at 20,000 rpm for 15 minutes. The pellet was discarded, then $(NH_4)_2SO_4$ was slowly added to the supernatant to a point of 60% saturation, and the solution incubated for a further 1 hour on ice and centrifuged at 20,000 rpm for 15 minutes. The supernatant was discarded and the pellet resuspended in washing buffer (50 mM phosphate buffer pH 7.5, 0.5 M NaCl, 20 mM imidazole), incubated for 20 minutes on ice, and then centrifuged at 25,000 rpm for 30 minutes. The supernatant was dialyzed overnight against 10,000 volumes of washing buffer, and centrifuging at 25,000 rpm for 30 minutes.

Further enrichment of target antigen can be achieved by affinity chromatography. The above supernatant was poured onto a Ni—NTA column equilibrated with washing buffer. Once the protein had been loaded onto resin, it was washed with 10-20 column volumes of washing buffer. The protein was eluted with a linear gradient of imidazole over a range from 20 to 500 mM in a buffer also containing 50 mM Phosphate buffer 7.5 and 0.5 M NaCl. Eluted protein was desalted by dialyzing overnight against 10,000 volumes of 50 mM phosphate buffer pH 7.8, 20 mM NaCl. As a further purification step, the dialyzed solution was poured onto a Q-column equilibrated with 50 mM phosphate pH 7.8, 20 mM NaCl. Isocratic flow was applied with this buffer. The early, flow through, peak was collected and contaminants were eluted with 1 M NaCl. All fractions were collected for protein analysis. Protein aliquots were stored frozen at −80° C.

Analysis of Material

Root tissues harvested from the *P. hybrida* root cultures carrying the LicKM-PAD4 and LicKM expressing viral vectors were ground in a protein extraction buffer and analyzed by Western analysis using antibodies specific to PA and LicB, and lichenase activity analysis. Analyses confirmed protein production of the predicted molecular weight for LicKM-PAD4, 43 kDa and the predicted molecular weight for LicKM, 28 kDa. The concentration of protein was assessed by comparison to a co-loaded dilution series (e.g., commercially sold PA standard (List Biologics), LicKM-PAD4 expressed in *E. coli*; LicKM expressed in *E. coli*). LicKM was quantitated at 30 mg/kg, and LicKM-PAD4 at 5.0 mg/kg. Furthermore, lichenase activity was determined in test and placebo material using the quantitative lichenase activity assay, and confirmed the data obtained from Western blot analyses.

Test capsules prepared using the *P. hybrida* root culture production system, are being tested for stability of carrier placebo and over a period of storage. Three capsules are being stored at −20° C. and three capsules are being stored at 4° C. Capsules are dissolved in PBS on days 7, 14, and 28 of the study and are tested for enzymatic activity of LicKM, and, following polyacrylamide gel electrophoresis and immunoblot analysis, for the presence of the predicted size protein recognized by antibodies specific to target antigen or placebo. In addition, on the day of each vaccination, a single test capsule will be used to assess the integrity of the target antigen in the vaccine.

EXAMPLE 5

Immunogenicity Studies

Initial Immunogenicity Study

An initial immunogenicity study was conducted to determine whether plant-produced LicKM-PAD4 could induce serum specific IgG in mice immunized intraperitoneally, and whether the induced antibodies could neutralize PA in vitro. The study used LicKM and LicKM-PAD4 enriched from *Agrobacterium* infiltrated leaves of *N. benthamiana* to 75% purity, as described above.

Eight-week old female BALB/c mice were immunized with 200 μg per dose of recombinant LicKM-PAD4. Three immunizations of 0.1 ml volume were administered intraperitoneally at intervals of two weeks. The first dose included complete Freund's adjuvant at a 1:1 volume ratio, the second dose included incomplete Freund's adjuvant at a 1:1 volume ratio, and the third dose did not include any adjuvant. A negative control group received LicKM at the same dosage. Four mice were in each group. Pre-immune sera were collected one day before the first dosing, and sera were subsequently collected 12 days after each immunization. PA specific IgG antibody titers were determined using an (ELISA). No animals had significant PA specific IgG in their pre-immune sera. All animals that received LicKM-PAD4, but no animals that received LicKM alone, showed a significant PA specific IgG response (FIG. 4). From this study it can be concluded that the plant-produced LicKM-PAD4 administered intraperitoneally to mice is immunogenic. Throughout the study animals were observed for potential signs of distress, diarrhea, death or other clinical signs that may result from administration of the target antigen. No adverse effects, distress, death or other clinical signs were observed.

To assess the ability of LicKM-PAD4 to stimulate toxin-neutralizing antibodies in immunized animals, we tested the serum antibodies for lethal toxin neutralizing activity in vitro using a WST-1-based cell viability quantification assay on a murine macrophage/monocyte (RAW264.7) cell line culture. Serial dilutions of PA specific antibodies and serial dilutions of sera from immunized animals were assayed against a standard concentration of PA. Human hybridoma-produced monoclonal antibody was used as a positive control. Antibodies and sera were mixed with PA 30 minutes prior to exposure to the cells in the presence of LF. PA, with or without antibody or sera, was then incubated with the cells for 12 to 15 hours, after which WST-1 was added for quantification of cell viability.

Figure 5:
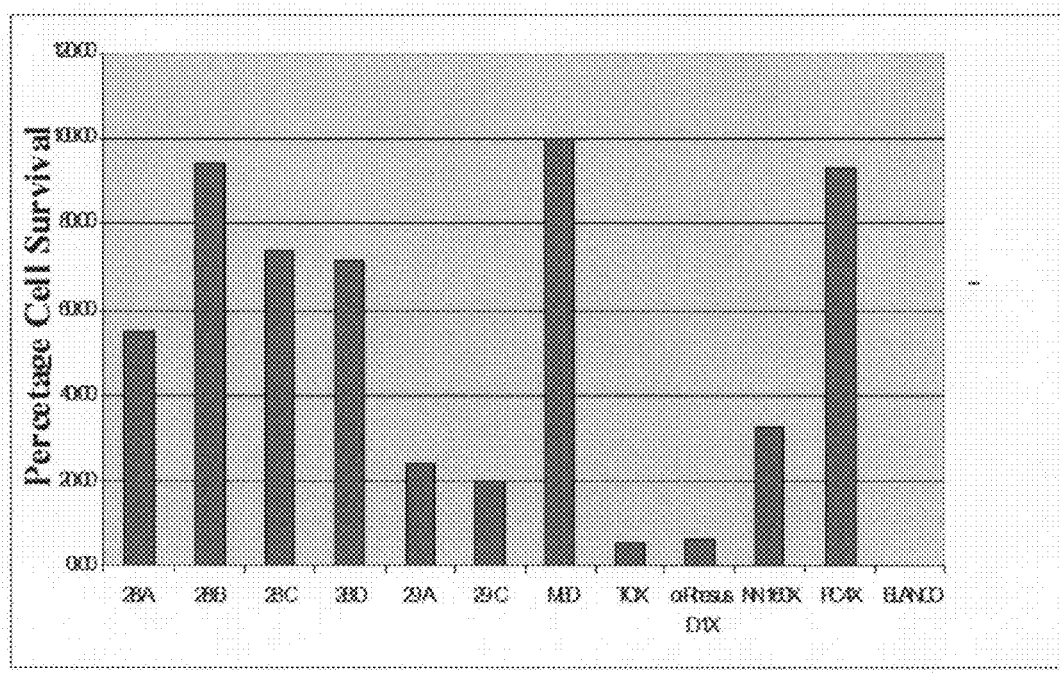
FIG. 5. LT neutralization assays. Sera from individual mice immunized with three doses of LicKM-PAD4 (28A, 28B, 28C, 28D), LicKM (29A, 29C), or media (MED) only. (Blanco=no cells; Tox and alphaRes cells were incubated with toxin without antibody present; NN160X indicates wells containing RAW274.7 cells, bioactive PA, bioactive LF, and anti-PA antibodies (different than positive control).

Cells that were not challenged showed complete survival, and cells that were challenged in the absence of antibodies or sera did not survive. Sera from all animals that received LicKM-PAD4, but from no animals that received LicKM alone, showed a significant toxin neutralization activity (FIG. 5). From this study it can be concluded that the plant-produced LicKM-PAD4 administered intraperitoneally to mice can induce antibodies that neutralize anthrax lethal toxin in an in vitro assay.

Follow-Up Immunogenicity and Protective Efficacy

A follow-up immunogenicity and protective efficacy study was conducted to determine whether plant-produced LicKM-PAD4 would induce specific serum IgG in mice immunized subcutaneously or intranasally and provide protection against challenge with lethal toxin. This study assessed the potency of the plant-produced material. Since intranasal administration targets a mucosal surface, this study provides an indication of how the vaccine candidate will perform when administered orally in the proposed clinical trial.

Six to eight week old female BALB/c mice were immunized with a dose range from 10 to 20 µg per dose of purified recombinant LicKM-PAD4 derived from plant material. Three immunizations of 0.1 ml volume were administered subcutaneously at intervals of two weeks. The first dose included complete Freund's adjuvant at a 1:1 volume ratio, and the second and third doses included incomplete Freund's adjuvant at a 1:1 volume ratio. Alternatively, three immunizations of 100 µl volume, with 20 µg antigen per dose, were administered as droplets intranasally at intervals of two weeks. No adjuvant was used for nasal delivery. For both subcutaneous and intranasal delivery, a negative control group received 20 µg doses of LicKM, and a positive control group received 20 µg PA (List Biologics). Ten mice were in each group. Pre-immune sera were collected one day before the first dosing, and immune sera were collected on day 38 of the study by retro-orbital bleed. PA specific IgG antibody titers were determined using a solid phase ELISA. No animals had significant PA specific IgG in their pre-immune sera. No animals that received LicKM alone, either subcutaneously or intranasally, showed a significant PA specific IgG response, but animals that received LicKM-PAD4 showed a response. From this study it can be concluded that the test material administered subcutaneously or intranasally to mice is immunogenic. Throughout the study animals were observed for potential signs of distress, diarrhea, death or other clinical signs that may result from administration of the target antigen. No adverse effects, distress, death or other clinical signs were observed.

On day 38 mice were challenged by intravenous injection with a mixture of 25 µg each of PA and LF (lethal toxin) in a 500 µl volume. Animals were observed continually for two hours post-challenge and subsequently at one hour intervals until 8 hours post-challenge. Observations were then continued twice daily until the study was concluded, when the animals were euthanized with $CO_2$. Clinical signs of stress, including fatalities, were recorded.

Figure 6:
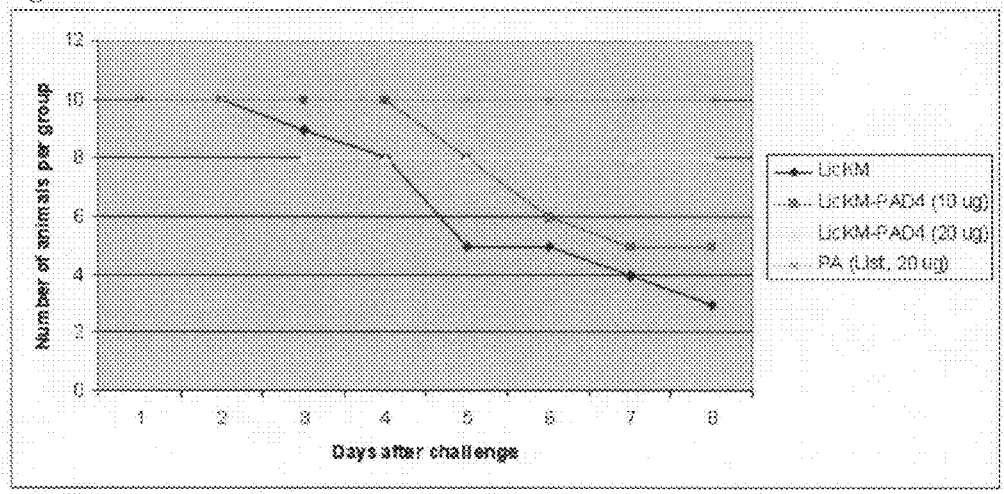
FIG. 6. Challenge study for mice vaccinated subcutaneously. Mice receive three injections and were subsequently challenged with lethal toxin. The number of animals that survived the challenge is indicated.
Figure 7:
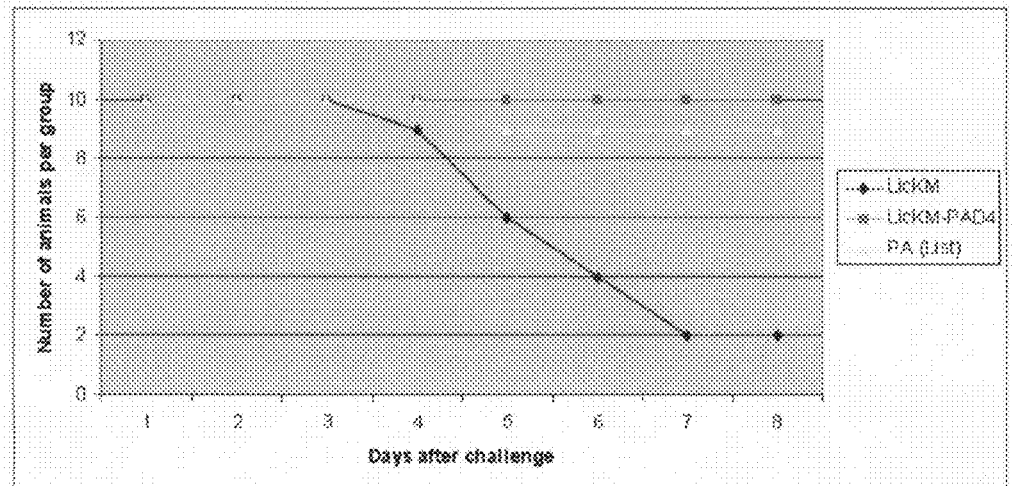
FIG. 7. Challenge study for mice vaccinated intranasally. Mice received three intranasal administrations and were subsequently challenged with lethal toxin. The number of animals that survived the challenge is indicated.
Figure 8:
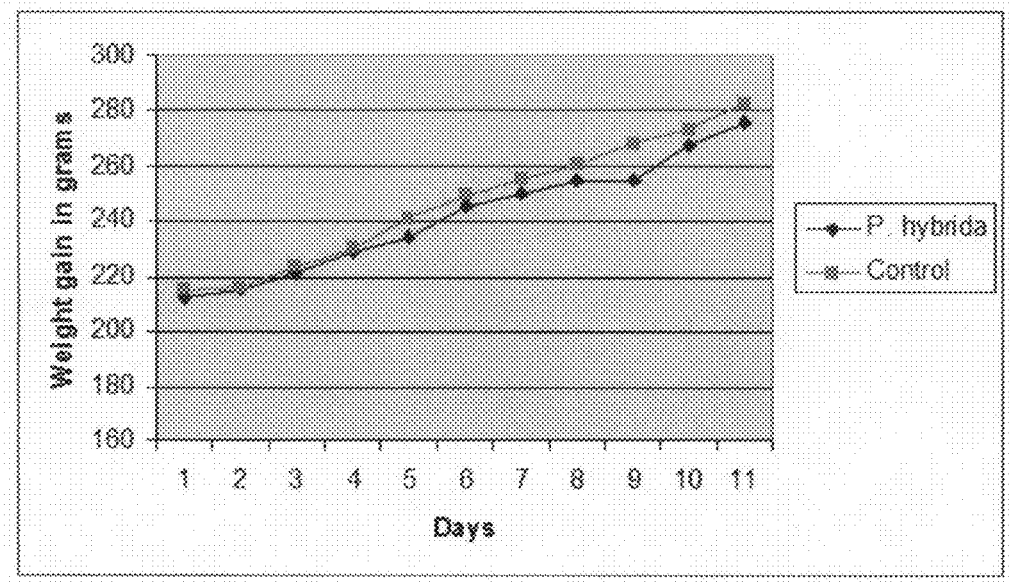
FIG. 8. Weight gain for rats in a safety study to determine safety of orally administered extract of *Petunia hybrida*.

Animals that received 10 µg LicKM-PAD4 per dose subcutaneously had a survival rate of 50% compared to 80% in a group that received 20 µg per dose subcutaneously (FIG. 6). In a control group that received 20 µg LicKM per dose subcutaneously only two animals survived. Animals that received 20 µg LicKM-PAD4 per dose intranasally had a survival rate of 100% compared to 20% for a group that received 20 µg LicKM per dose intranasally (FIG. 7). From this study it can be concluded that the plant-produced LicKM-PAD4 administered subcutaneously or intranasally to mice is protective against anthrax lethal toxin.

EXAMPLE 6

Immunization of Mice with a Combination of Target Antigens

Production of Target Antigens

Constructs expressing target antigens were prepared as described in the previous Examples. Briefly, amino acids 592 to 731 of PA (GenBank accession number P13423) and amino acids 34 to 287 of LF (GenBank accession number M29081) were engineered as internal in-frame fusions with LicKM to obtain LicKM-PAD4 and LicKM-LFD1. LicKM-PAD4 was cloned in pBID4 and the resulting construct, pBID4-LicKM-PAD4, was introduced into Agrobacterium tumefaciens. LicKM-LFD1 was cloned in the TMV-based expression vector 30B [8] to obtain 30B-LicKM-LFD1.

Target antigens were prepared as described in the previous Examples. Briefly, expression of LicKM-PAD4 was achieved in N. benthamiana plants following agroinfiltration with pBID4-LicKM-PAD4, whereas LicKM-LFD1 was produced following inoculation of leaves with in vitro transcript of 30B-LicKM-LFD1. Tissue was collected 4-7 days following inoculation, and each target antigen was purified by affinity chromatography followed by ion exchange chromatography. Purified proteins were characterized by SDS-PAGE followed by immuno-blot analysis using target specific antibodies.

Figure 9:
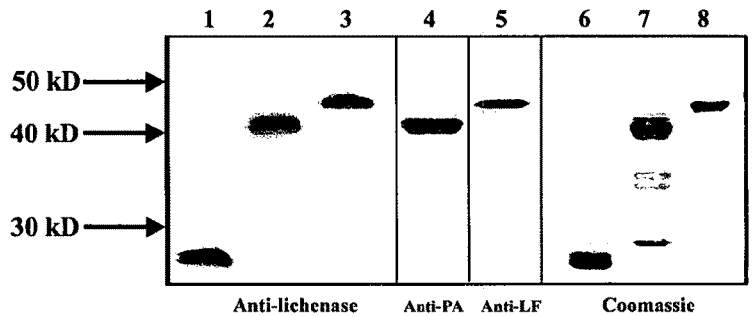
FIG. 9. In vitro characterization of plant-produced anthrax antigens. Plant-produced LicKM, (Lane 1), LicKM-PAD4 (Lane 2), and LicKM-LFD1 (Lane 3) were analyzed by SDS-PAGE followed by immunoblotting using an anti-LicKM antibody. LicKM-PAD4 (Lane 4) and LicKM-LFD1 (Lane 5) were also detected in an immunoblot using antibodies against PA and LF, respectively. The quality of target antigens purified from plant tissue was analyzed by SDS-PAGE followed by Coomassie staining; LicKM (Lane 6), LicKM-PAD4 (Lane 7), and LicKM-LF (Lane 8).

Recombinant LicKM-PAD4 and LicKM-LFD1 expressed in N. benthamiana were recovered and characterized by immunoblot analysis (FIG. 9). LicKM-PAD4 and LicKM-LFD1 had specific reactivity to antibodies specific for PA and LF, respectively, and both fusion proteins reactive with antibody to LicKM (FIG. 9). The fusion proteins recognized by these antibodies were of the predicted sizes.

Immunogenicity Studies

Six-week old female A/J mice, 6 mice per group (Harlan, Indianapolis, Ind.) were injected intraperitoneally (i.p.) with three doses of vaccine candidates or control material at 2-week intervals. Control groups received 50 µg per dose of plant-produced LicKM or recombinant full length B. anthracis LF or PA (List Biological Laboratories Inc.). Mice immunized with the combination of plant-produced LicKM-PAD4 and LicKM-LFD1 received 100 µg of each fusion per dose. For each group, the priming dose was emulsified in complete Freund's adjuvant, and the second dose was emulsified in incomplete Freund's adjuvant (Sigma-Aldrich). Serum samples were collected prior to each injection and 2 weeks after the third dose.

PA- and LF-specific IgG antibodies were detected by ELISA. MaxiSorp 96-well plates (Nunc, Rochester, N.Y.) were coated with 1 µg/ml or 0.6 µg/ml of recombinant PA or LF, respectively. Serum samples were added at an initial dilution of 1:100, titrated in 5-fold dilutions, and target-specific antibodies were detected using goat anti-mouse IgG conjugated to HRP (Jackson ImmunoResearch, West Grove, Pa.). Titers of IgG antibody subtypes were determined using goat anti-mouse IgG1, IgG2a, IgG2b, or IgG3 conjugated to HRP (Jackson ImmunoResearch) as secondary antibodies. The titers of B. anthracis lethal toxin (LeTx) neutralizing antibodies were determined as described (Hull et al., 2005, Vaccine, 23:2082).

Figure 10:
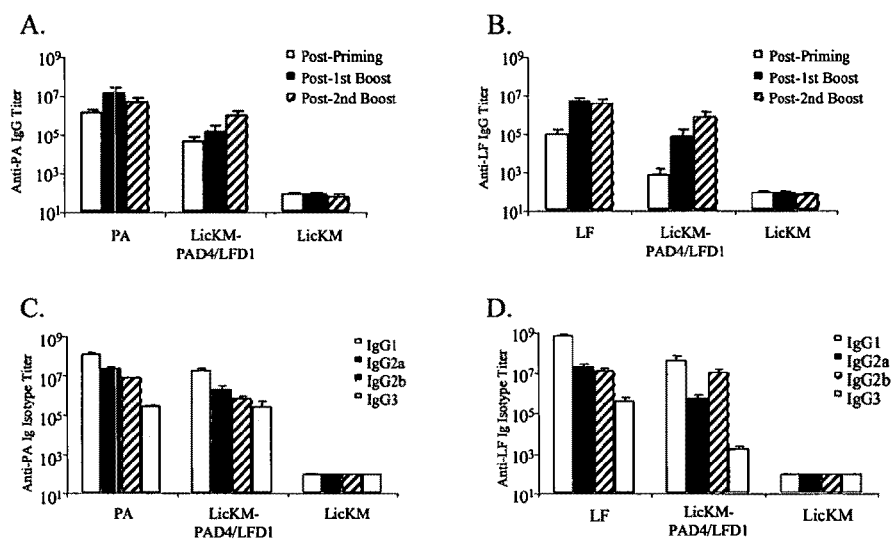
FIG. 10. Immunization with subunit vaccine candidate elicits high titer neutralizing antibody. Sera were collected from immunized mice two weeks after each antigen dose and tested by ELISA for the presence of PA-specific (10A) and LF-specific (10B) IgG after prime (open bars), first boost (solid bars), and second boost (striped bars). Data are represented as average titer±standard deviation. Antibody isotypes of anti-PA (10C) and anti-LF (10D) serum IgG responses post second boost were determined by quantitative ELISA. Data are represented as µg/ml antigen specific antibody isotype±standard deviation. Pre-immune antigen-specific antibody levels were subtracted from each data point. For in vitro LeTx neutralization assay (10E), sera were pooled from groups of immunized mice and incubated with recombinant PA for 30 minutes. This mixture was then added to RAW 264.7 cells and incubated in the presence of LF for 4 hours after which cell viability was measured. Data are represented as the average percent cell survival of two experiments±standard deviation.
Figure 10:
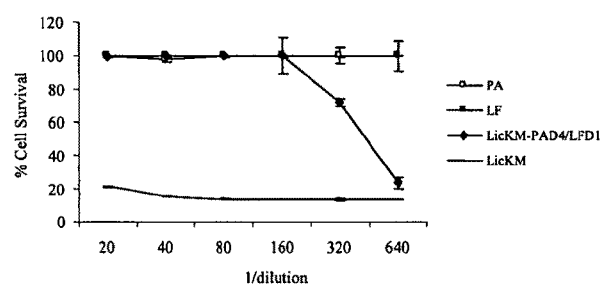

Significant levels of PA- and LF-specific IgG were detected post-priming with the mixture of LicKM-PAD4 and LicKM-LFD1, and continued to increase following the first boost with peak antibody titers of $10^6$ detected after the second boost (FIG. 10A,B). IgG titers remained at this level for 10 weeks post second boost, which may indicate long-lasting antibody production and establishment of memory responses. Comparable antibody titers were detected in sera from mice immunized with *E. coli*-produced full-length PA or LF. Mice in the negative control group, immunized with LicKM, had negligible serum titers to PA or LF (FIG. 10A,B).

For both the PA- (FIG. 10C) and LF- (FIG. 10D) specific responses, IgG1 was the predominant isotype elicited by the combination subunit vaccine. This dominance in IgG1 antibody isotype was also observed in mice receiving *E. coli*-produced full-length PA or LF, suggesting that the individual domains of PA and LF produced here were able to elicit humoral immune responses with similar characteristics observed with the respective full-length proteins. IgG1 antibodies against PA and LF have been previously shown to be the dominant isotype induced by anthrax vaccines. These antibodies have been shown to protect against LeTx both in vitro and in vivo (Flick-Smith et al., 2002, *Infection and Immunity*, 70:1653d; Lim et al., 2005, *Infection and Immunity*, 73:6547; and Gu et al., 1999, *Vaccine*, 17:340). IgG2a, IgG2b and IgG3 isotypes were present in the serum of mice that received the plant-produced antigens, but to a lesser extent than IgG1 (FIG. 10C,D).

To determine whether the anti-PA and anti-LF IgG antibodies produced in response to immunization with a mixture of LicKM-PAD4 and LicKM-LFD 1 could protect cells against LeTx, an in vitro neutralization assay was performed using the mouse macrophage cells line RAW264.7 (FIG. 10E). Protection from LeTx associated cell death was observed when pooled serum from mice immunized LicKM-PAD4 plus LicKM-LFD1 was diluted out to 1:160. At a 1:320 serum dilution, 75% of the cells survived LeTx associated cell death, suggesting protective efficacy of this vaccine candidate. By contrast, no cell survival was observed when serum from mice immunized with LicKM was assessed for LeTx neutralizing activity. The results presented here demonstrate the immunogenic and immunoprotective properties of a plant derived dual subunit vaccine against *B. anthracis*.

What is claimed is:

1. An isolated antigen comprising a component of *Bacillus anthracis* virulence factor fused to a LicKM protein;
   wherein the virulence factor component comprises at least one domain having an amino acid sequence with at least 95% identity to a sequence selected from the group consisting of SEQ ID NO.: 4, SEQ ID NO: 6, SEQ ID NO: 15, amino acid residues 1-137 of SEQ ID NO.: 2, amino acid residues 251-263 of SEQ ID NO.: 2, amino acid residues 138-250 of SEQ ID NO.: 2, amino acid residues 264-283 of SEQ ID NO.: 2, amino acid residues 429-551 of SEQ ID NO.: 2, amino acid residues 306-385 of SEQ ID NO.: 2, amino acid residues 552-776 of SEQ ID NO.: 2, amino acid residues 1-250 of SEQ ID NO.: 1, amino acid residues 251-456 of SEQ ID NO.: 1, amino acid residues 477-595 of SEQ ID NO.: 1, and amino acid residues 608-735 of SEQ ID NO.: 1; and
   wherein the LicKM protein comprises an amino acid sequence with at least 95% identity to SEQ ID NO.: 8 or SEQ ID NO.: 10.

2. An immunogenic composition comprising an antigen comprising a component of *Bacillus anthracis* virulence factor fused to a LicKM protein and a pharmaceutically acceptable carrier;
   wherein the virulence factor component comprises at least one domain having an amino acid sequence with at least 95% identity to a sequence selected from the group consisting of SEQ ID NO.:4, SEQ ID NO: 6, SEQ ID NO: 15, amino acid residues 1-137 of SEQ ID NO.: 2, amino acid residues 251-263 of SEQ ID NO.: 2, amino acid residues 138-250 of SEQ ID NO.: 2, amino acid residues 264-283 of SEQ ID NO.: 2, amino acid residues 429-551 of SEQ ID NO.: 2, amino acid residues 306-385 of SEQ ID NO.: 2, amino acid residues 552-776 of SEQ ID NO.: 2, amino acid residues 1-250 of SEQ ID NO.: 1, amino acid residues 251-456 of SEQ ID NO.: 1, amino acid residues 477-595 of SEQ ID NO.: 1, and amino acid residues 608-735 of SEQ ID NO.: 1;
   wherein the LicKM protein comprises an amino acid sequence with at least 95% identity to SEQ ID NO.: 8 or SEQ ID NO.: 10;
   and wherein the composition is capable of eliciting an immune response upon administration to a subject.

3. An immunogenic composition comprising: at least two antigens, each of which comprises a component of *Bacillus anthracis* virulence factor having an amino acid sequence with at least 95% identity to a sequence selected from the group consisting of SEQ ID NO.:4, SEQ ID NO: 6, SEQ ID NO: 15, amino acid residues 1-137 of SEQ ID NO.: 2, amino acid residues 251-263 of SEQ ID NO.: 2, amino acid residues 138-250 of SEQ ID NO.: 2, amino acid residues 264-283 of SEQ ID NO.: 2, amino acid residues 429-551 of SEQ ID NO.:

2, amino acid residues 306-385 of SEQ ID NO.: 2, amino acid residues 552-776 of SEQ ID NO.: 2, amino acid residues 1-250 of SEQ ID NO.: 1, amino acid residues 251-456 of SEQ ID NO.: 1, amino acid residues 477-595 of SEQ ID NO.: 1, and amino acid residues 608-735 of SEQ ID NO.: 1, wherein at least one of the antigens further comprises a LicKM protein, and wherein the LicKM protein comprises an amino acid sequence with at least 95% identity to SEQ ID NO.: 8 or SEQ ID NO.: 10.

4. The immunogenic composition of claim 3, wherein at least one of the antigens comprises a virulence factor component consisting of an amino acid sequence selected from the group consisting of about amino acid residues 1-137 of SEQ ID NO.:2, amino acid residues 251-263 of SEQ ID NO.:2, amino acid residues 138-250 of SEQ ID NO.:2, amino acid residues 264-283 of SEQ ID NO.:2, amino acid residues 429-551 of SEQ ID NO.:2, amino acid residues 306-385 of SEQ ID NO:2, and amino acid residues 552-776 of SEQ ID NO.:2.

5. The immunogenic composition of claim 3, wherein at least one of the antigens comprises the amino acid sequence of SEQ ID NO.: 14.

6. The immunogenic composition of claim 3, wherein at least one of the antigens comprises a virulence factor component consisting of an amino acid sequence selected from the group consisting of about amino acid residues 1-250 of SEQ ID NO.:1, amino acid residues 241-456 of SEQ ID NO.:1, amino acid residues 477-595 of SEQ ID NO.:1, and amino acid residues 608-735 of SEQ ID NO.:1.

7. The immunogenic composition of claim 3, wherein at least one of the antigens comprises the amino acid sequence of SEQ ID NO.: 12.

8. The immunogenic composition of claim 3, wherein the virulence factor component consists of SEQ ID NO.:15.

9. The immunogenic composition of claim 3, wherein the virulence factor component is fused to the LicKM protein at the LicKM N-terminus or at the LicKM C-terminus, or is fused to a loop structure that is exposed on the surface of LicKM and is located far from the LicKM active domain.

10. The immunogenic composition of claim 3, wherein the virulence factor component of at least one antigen comprises at least two amino acid sequences with at least 95% identity to a sequence selected from the group consisting of SEQ ID NO.:4, SEQ ID NO: 6, SEQ ID NO: 15, amino acid residues 1-137 of SEQ ID NO.: 2, amino acid residues 251-263 of SEQ ID NO.: 2, amino acid residues 138-250 of SEQ ID NO.: 2, amino acid residues 264-283 of SEQ ID NO.: 2, amino acid residues 429-551 of SEQ ID NO.: 2, amino acid residues 306-385 of SEQ ID NO.: 2, amino acid residues 552-776 of SEQ ID NO.: 2, amino acid residues 1-250 of SEQ ID NO.: 1, amino acid residues 251-456 of SEQ ID NO.: 1, amino acid residues 477-595 of SEQ ID NO.: 1, and amino acid residues 608-735 of SEQ ID NO.: 1.

11. The immunogenic composition of claim 10, wherein at least one antigen comprises SEQ ID NO.:4 and at least one antigen comprises amino acid residues 1-137 of SEQ ID NO.: 2, amino acid residues 251-263 of SEQ ID NO.: 2, amino acid residues 138-250 of SEQ ID NO.: 2, amino acid residues 264-283 of SEQ ID NO.: 2, amino acid residues 429-551 of SEQ ID NO.: 2, amino acid residues 306-385 of SEQ ID NO.: 2, or amino acid residues 552-776 of SEQ ID NO.: 2.

12. The immunogenic composition of claim 3, wherein the antigen is produced by a plant selected from a transgenic plant and a plant which transiently expresses the antigen.

13. The immunogenic composition of claim 3, wherein the composition comprises antigen which is purified, partially purified, or unpurified from plant cells, a plant, seeds, fruit, or an extract thereof.

14. The immunogenic composition of claim 3, further comprising at least one vaccine adjuvant.

15. The immunogenic composition of claim 14 wherein the adjuvant is selected from the group consisting of alum, MF59, MALP2, and saponin.

16. A method for inducing an immune response in a subject, comprising administering to a subject an effective amount of an anti-anthrax immunogenic composition, wherein the administration is sufficient to stimulate production of antigen specific antibodies or stimulate a cellular immune response by the subject; thereby inducing a protective immune response;
wherein the immunogenic composition comprises an antigen comprising a component of *Bacillus anthracis* virulence factor fused to a LicKM protein, wherein the LicKM protein comprises an amino acid sequence with at least 95% identity to SEQ ID NO.: 8 or SEQ ID NO.: 10; and
wherein the virulence factor component comprises at least one domain having an amino acid sequence with at least 95% identity to a sequence selected from the group consisting of SEQ ID NO.:4, SEQ ID NO: 6, SEQ ID NO: 15, amino acid residues 1-137 of SEQ ID NO.: 2, amino acid residues 251-263 of SEQ ID NO.: 2, amino acid residues 138-250 of SEQ ID NO.: 2, amino acid residues 264-283 of SEQ ID NO.: 2, amino acid residues 429-551 of SEQ ID NO.: 2, amino acid residues 306-385 of SEQ ID NO.: 2, amino acid residues 552-776 of SEQ ID NO.: 2, amino acid residues 1-250 of SEQ ID NO.: 1, amino acid residues 251-456 of SEQ ID NO.: 1, amino acid residues 477-595 of SEQ ID NO.: 1, and amino acid residues 608-735 of SEQ ID NO.: 1.

17. A method for inducing an immune response in a subject, comprising administering to a subject an effective amount of an anti-anthrax immunogenic composition, wherein the immunogenic composition comprise at least two antigens, each of which comprises a component of *Bacillus anthracis* virulence factor having an amino acid sequence with at least 95% identity to a sequence selected from the group consisting of SEQ ID NO.:4, SEQ ID NO: 6, SEQ ID NO: 15, amino acid residues 1-137 of SEQ ID NO.: 2, amino acid residues 251-263 of SEQ ID NO.: 2, amino acid residues 138-250 of SEQ ID NO.: 2, amino acid residues 264-283 of SEQ ID NO.: 2, amino acid residues 429-551 of SEQ ID NO.: 2, amino acid residues 306-385 of SEQ ID NO.: 2, amino acid residues 552-776 of SEQ ID NO.: 2, amino acid residues 1-250 of SEQ ID NO.: 1, amino acid residues 251-456 of SEQ ID NO.: 1, amino acid residues 477-595 of SEQ ID NO.: 1, and amino acid residues 608-735 of SEQ ID NO.: 1, wherein at least one of the antigens further comprises a LicKM protein, wherein the LicKM protein comprises an amino acid sequence with at least 95% identity to SEQ ID NO.: 8 or SEQ ID NO.: 10, and wherein the administration is sufficient to stimulate production of antigen specific antibodies or stimulate a cellular immune response by the subject; thereby inducing a protective immune response.

18. The isolated antigen of claim 1, wherein the virulence factor component comprises at least one domain having an amino acid sequence with at least 97% identity to a sequence selected from the group consisting of SEQ ID NO.: 4, SEQ ID NO: 6, SEQ ID NO: 15, amino acid residues 1-137 of SEQ ID NO.: 2, amino acid residues 251-263 of SEQ ID NO.: 2, amino acid residues 138-250 of SEQ ID NO.: 2, amino acid residues 264-283 of SEQ ID NO.: 2, amino acid residue residues 429-551 of SEQ ID NO.: 2, amino acid residues 306-385 of SEQ ID NO.: 2, amino acid residues 552-776 of SEQ ID NO.: 2, amino acid residues 1-250 of SEQ ID NO.: 1, amino acid residues 251-456 of SEQ ID NO.: 1, amino acid residues 477-595 of SEQ ID NO.: 1, and amino acid residues 608-735 of SEQ ID NO.: 1.

19. The isolated antigen of claim 1, wherein the virulence factor component comprises at least one domain having an amino acid sequence with at least 98% identity to a sequence selected from the group consisting of SEQ ID NO.: 4, SEQ ID NO: 6, SEQ ID NO: 15, amino acid residues 1-137 of SEQ ID NO.: 2, amino acid residues 251-263 of SEQ ID NO.: 2, amino acid residues 138-250 of SEQ ID NO.: 2, amino acid residues 264-283 of SEQ ID NO.: 2, amino acid residues 429-551 of SEQ ID NO.: 2, amino acid residues 306-385 of SEQ ID NO.: 2, amino acid residues 552-776 of SEQ ID NO.: 2, amino acid residues 1-250 of SEQ ID NO.: 1, amino acid residues 251-456 of SEQ ID NO.: 1, amino acid residues 477-595 of SEQ ID NO.: 1, and amino acid residues 608-735 of SEQ ID NO.: 1.

20. The isolated antigen of claim 1, wherein the virulence factor component consists of an amino acid sequence selected from the group consisting of SEQ ID NO.: 4, SEQ ID NO: 6, SEQ ID NO: 15, amino acid residues 1-137 of SEQ ID NO.: 2, amino acid residues 251-263 of SEQ ID NO.: 2, amino acid residues 138-250 of SEQ ID NO.: 2, amino acid residues 264-283 of SEQ ID NO.: 2, amino acid residues 429-551 of SEQ ID NO.: 2, amino acid residues 306-385 of SEQ ID NO.: 2, amino acid residues 552-776 of SEQ ID NO.: 2, amino acid residues 1-250 of SEQ ID NO.: 1, amino acid residues 251-456 of SEQ ID NO.: 1, amino acid residues 477-595 of SEQ ID NO.: 1, and amino acid residues 608-735 of SEQ ID NO.: 1.

21. The isolated antigen of claim 1, wherein the LicKM protein has an amino acid sequence with at least 97% identity to SEQ ID NO.: 8 or SEQ ID NO.: 10.

22. The isolated antigen of claim 1, wherein the virulence factor component is fused to the LicKM protein at the LicKM N-terminus or at the LicKM C-terminus, or is fused to a loop structure that is exposed on the surface of LicKM and is located far from the LicKM active domain.

23. The isolated antigen of claim 1, wherein the antigen has the amino acid sequence of SEQ ID NO.: 12.

24. The isolated antigen of claim 1, wherein the antigen has the amino acid sequence of SEQ ID NO.: 14.

25. The isolated antigen of claim 1, wherein the antigen is produced by a plant selected from a transgenic plant and a plant which transiently expresses the antigen.

26. The isolated antigen of claim 1, wherein the antigen is purified, partially purified, or unpurified from plant cells, a plant, seeds, fruit, or an extract thereof.

27. The immunogenic composition of claim 2, wherein the virulence factor component comprises at least one domain having an amino acid sequence with at least 97% identity to a sequence selected from the group consisting of SEQ ID NO.: 4, SEQ ID NO: 6, SEQ ID NO: 15, amino acid residues 1-137 of SEQ ID NO.: 2, amino acid residues 251-263 of SEQ ID NO.: 2, amino acid residues 138-250 of SEQ ID NO.: 2, amino acid residues 264-283 of SEQ ID NO.: 2, amino acid residues 429-551 of SEQ ID NO.: 2, amino acid residues 306-385 of SEQ ID NO.: 2, amino acid residues 552-776 of SEQ ID NO.: 2, amino acid residues 1-250 of SEQ ID NO.: 1, amino acid residues 251-456 of SEQ ID NO.: 1, amino acid residues 477-595 of SEQ ID NO.: 1, and amino acid residues 608-735 of SEQ ID NO.: 1.

28. The immunogenic composition of claim 2, wherein the virulence factor component comprises at least one domain having an amino acid sequence with at least 98% identity to a sequence selected from the group consisting of SEQ ID NO.: 4, SEQ ID NO: 6, SEQ ID NO: 15, amino acid residues 1-137 of SEQ ID NO.: 2, amino acid residues 251-263 of SEQ ID NO.: 2, amino acid residues 138-250 of SEQ ID NO.: 2, amino acid residues 264-283 of SEQ ID NO.: 2, amino acid residues 429-551 of SEQ ID NO.: 2, amino acid residues 306-385 of SEQ ID NO.: 2, amino acid residues 552-776 of SEQ ID NO.: 2, amino acid residues 1-250 of SEQ ID NO.: 1, amino acid residues 251-456 of SEQ ID NO.: 1, amino acid residues 477-595 of SEQ ID NO.: 1, and amino acid residues 608-735 of SEQ ID NO.: 1.

29. The immunogenic composition of claim 2, wherein the virulence factor component consists of an amino acid sequence selected from the group consisting of SEQ ID NO.: 4, SEQ ID NO: 6, SEQ ID NO: 15, amino acid residues 1-137 of SEQ ID NO.: 2, amino acid residues 251-263 of SEQ ID NO.: 2, amino acid residues 138-250 of SEQ ID NO.: 2, amino acid residues 264-283 of SEQ ID NO.: 2, amino acid residues 429-551 of SEQ ID NO.: 2, amino acid residues 306-385 of SEQ ID NO.: 2, amino acid residues 552-776 of SEQ ID NO.: 2, amino acid residues 1-250 of SEQ ID NO.: 1, amino acid residues 251-456 of SEQ ID NO.: 1, amino acid residues 477-595 of SEQ ID NO.: 1, and amino acid residues 608-735 of SEQ ID NO.: 1.

30. The immunogenic composition of claim 2, wherein the LicKM protein has an amino acid sequence with at least 97% identity to SEQ ID NO.: 8 or SEQ ID NO.: 10.

31. The immunogenic composition of claim 2, wherein the virulence factor component is fused to the LicKM protein at the LicKM N-terminus or at the LicKM C-terminus, or is fused to a loop structure that is exposed on the surface of LicKM and is located far from the LicKM active domain.

32. The immunogenic composition of claim 2, wherein the antigen has the amino acid sequence of SEQ ID NO.: 12.

33. The immunogenic composition of claim 2, wherein the antigen has the amino acid sequence of SEQ ID NO.: 14.

34. The immunogenic composition of claim 2, wherein the antigen is produced by a plant selected from a transgenic plant and a plant that transiently expresses the antigen.

35. The immunogenic composition of claim 2, wherein the composition comprises antigen that is purified, partially purified, or unpurified from plant cells, a plant, seeds, fruit, or an extract thereof.

36. The immunogenic composition of claim 2, further comprising at least one vaccine adjuvant.

37. The immunogenic composition of claim 34, wherein the adjuvant is selected from the group consisting of alum, MF59, MALP2, and saponin.

38. The immunogenic composition of claim 3, wherein each antigen comprises a component of *Bacillus anthracis* virulence factor having an amino acid sequence with at least 97% identity to a sequence selected from the group consisting of SEQ ID NO.:4, SEQ ID NO: 6, SEQ ID NO: 15, amino acid residues 1-137 of SEQ ID NO.: 2, amino acid residues 251-263 of SEQ ID NO.: 2, amino acid residues 138-250 of SEQ ID NO.: 2, amino acid residues 264-283 of SEQ ID NO.: 2, amino acid residues 429-551 of SEQ ID NO.: 2, amino acid residues 306-385 of SEQ ID NO.: 2, amino acid residues 552-776 of SEQ ID NO.: 2, amino acid residues 1-250 of SEQ ID NO.: 1, amino acid residues 251-456 of SEQ ID NO.: 1, amino acid residues 477-595 of SEQ ID NO.: 1, and amino acid residues 608-735 of SEQ ID NO.: 1.

39. The immunogenic composition of claim 3, wherein each antigen comprises a component of *Bacillus anthracis* virulence factor having an amino acid sequence with at least 98% identity to a sequence selected from the group consisting of SEQ ID NO.:4, SEQ ID NO: 6, SEQ ID NO: 15, amino acid residues 1-137 of SEQ ID NO.: 2, amino acid residues 251-263 of SEQ ID NO.: 2, amino acid residues 138-250 of SEQ ID residues residue 429-551 of SEQ ID NO.: 2, amino acid residues 306-385 of SEQ ID NO.: 2, amino acid residues 552-776 of SEQ ID NO.: 2, amino acid residues 1-250 of SEQ ID NO.: 1, amino acid residues 251-456 of SEQ ID NO.: 1, amino acid residues 477-595 of SEQ ID NO.: 1, and about amino acid residues 608-735 of SEQ ID NO.: 1.

* * * * *

UNITED STATES PATENT AND TRADEMARK OFFICE
CERTIFICATE OF CORRECTION

PATENT NO. : 8,277,816 B2
APPLICATION NO. : 11/706576
DATED : October 2, 2012
INVENTOR(S) : Vidadi Yusibov Page 1 of 1

It is certified that error appears in the above-identified patent and that said Letters Patent is hereby corrected as shown below:

Column 2 (other publications), line 1, please delete "Proc.Natl.Acad.Sci" and insert --Proc. Natl. Acad. Sci.--, therefor.

Column 2 (other publications), line 1, please delete "vol. 90 :" and insert --vol. 90:--, therefor.

Column 2 (other publications), line 3, please delete "Biol.Council." and insert --Biol. Council.--, therefor.

Column 99, line 27 (Claim 6), after "of" delete "about".

Column 101, line 1 (Claim 18), after "acid" delete "residue".

Column 103, line 6 (Claim 39), after "ID" please insert --NO.: 2, amino acid residues 264-283 of SEQ ID NO.: 2, amino acid--, therefor.

Column 103, line 6 (Claim 39), after "residues" delete "residue".

Column 104, line 3 (Claim 39), after "and" delete "about".

Signed and Sealed this
Twenty-sixth Day of February, 2013

Teresa Stanek Rea
*Acting Director of the United States Patent and Trademark Office*

```
                        SEQUENCE LISTING

<160> NUMBER OF SEQ ID NOS: 15

<210> SEQ ID NO 1
<211> LENGTH: 764
<212> TYPE: PRT
<213> ORGANISM: Artificial Sequence
<220> FEATURE:
<223> OTHER INFORMATION: Protective antigan sequence

<400> SEQUENCE: 1

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Arg Lys Lys Arg Ser Thr Ser Ala Gly Pro Thr Val Pro Asp Arg Asp
        195                 200                 205
```

```
Asn Asp Gly Ile Pro Asp Ser Leu Glu Val Glu Gly Tyr Thr Val Asp
    210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
        275                 280                 285

Pro Ile Val His Val Asp Met Glu Asn Ile Ile Leu Ser Lys Asn Glu
    290                 295                 300

Asp Gln Ser Thr Gln Asn Thr Asp Ser Glu Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
            340                 345                 350

Phe Ser Asn Ser Asn Ser Ser Thr Val Ala Ile Asp His Ser Leu Ser
        355                 360                 365

Leu Ala Gly Glu Arg Thr Trp Ala Glu Thr Met Gly Leu Asn Thr Ala
    370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                405                 410                 415

Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
        435                 440                 445

Ala Leu Asn Ala Gln Asp Asp Phe Ser Ser Thr Pro Ile Thr Met Asn
    450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
        515                 520                 525

Leu Val Glu Arg Arg Ile Ala Ala Val Asn Pro Ser Asp Pro Leu Glu
    530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590

Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640
```

-continued

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
        755                 760

<210> SEQ ID NO 2
<211> LENGTH: 809
<212> TYPE: PRT
<213> ORGANISM: Anthracis bacillus

<400> SEQUENCE: 2

Met Asn Ile Lys Lys Glu Phe Ile Lys Val Ile Ser Met Ser Cys Leu
1               5                   10                  15

Val Thr Ala Ile Thr Leu Ser Gly Pro Val Phe Ile Pro Leu Val Gln
            20                  25                  30

Gly Ala Gly Gly His Gly Asp Val Gly Met His Val Lys Glu Lys Glu
        35                  40                  45

Lys Asn Lys Asp Glu Asn Lys Arg Lys Asp Glu Glu Arg Asn Lys Thr
    50                  55                  60

Gln Glu Glu His Leu Lys Glu Ile Met Lys His Ile Val Lys Ile Glu
65                  70                  75                  80

Val Lys Gly Glu Glu Ala Val Lys Lys Glu Ala Ala Glu Lys Leu Leu
                85                  90                  95

Glu Lys Val Pro Ser Asp Val Leu Glu Met Tyr Lys Ala Ile Gly Gly
            100                 105                 110

Lys Ile Tyr Ile Val Asp Gly Asp Ile Thr Lys His Ile Ser Leu Glu
        115                 120                 125

Ala Leu Ser Glu Asp Lys Lys Lys Ile Lys Asp Ile Tyr Gly Lys Asp
    130                 135                 140

Ala Leu Leu His Glu His Tyr Val Tyr Ala Lys Glu Gly Tyr Glu Pro
145                 150                 155                 160

Val Leu Val Ile Gln Ser Ser Glu Asp Tyr Val Glu Asn Thr Glu Lys
                165                 170                 175

Ala Leu Asn Val Tyr Tyr Glu Ile Gly Lys Ile Leu Ser Arg Asp Ile
            180                 185                 190

Leu Ser Lys Ile Asn Gln Pro Tyr Gln Lys Phe Leu Asp Val Leu Asn
        195                 200                 205

Thr Ile Lys Asn Ala Ser Asp Ser Asp Gly Gln Asp Leu Leu Phe Thr
    210                 215                 220

Asn Gln Leu Lys Glu His Pro Thr Asp Phe Ser Val Glu Phe Leu Glu
225                 230                 235                 240

Gln Asn Ser Asn Glu Val Gln Glu Val Phe Ala Lys Ala Phe Ala Tyr
                245                 250                 255

```
Tyr Ile Glu Pro Gln His Arg Asp Val Leu Gln Leu Tyr Ala Pro Glu
            260                 265                 270

Ala Phe Asn Tyr Met Asp Lys Phe Asn Glu Gln Glu Ile Asn Leu Ser
        275                 280                 285

Leu Glu Glu Leu Lys Asp Gln Arg Met Leu Ala Arg Tyr Glu Lys Trp
    290                 295                 300

Glu Lys Ile Lys Gln His Tyr Gln His Trp Ser Asp Ser Leu Ser Glu
305                 310                 315                 320

Glu Gly Arg Gly Leu Leu Lys Lys Leu Gln Ile Pro Ile Glu Pro Lys
                325                 330                 335

Lys Asp Asp Ile Ile His Ser Leu Ser Gln Glu Lys Glu Leu Leu
            340                 345                 350

Lys Arg Ile Gln Ile Asp Ser Ser Asp Phe Leu Ser Thr Glu Glu Lys
            355                 360                 365

Glu Phe Leu Lys Lys Leu Gln Ile Asp Ile Arg Asp Ser Leu Ser Glu
    370                 375                 380

Glu Glu Lys Glu Leu Leu Asn Arg Ile Gln Val Asp Ser Ser Asn Pro
385                 390                 395                 400

Leu Ser Glu Lys Glu Lys Glu Phe Leu Lys Lys Leu Lys Leu Asp Ile
                405                 410                 415

Gln Pro Tyr Asp Ile Asn Gln Arg Leu Gln Asp Thr Gly Gly Leu Ile
            420                 425                 430

Asp Ser Pro Ser Ile Asn Leu Asp Val Arg Lys Gln Tyr Lys Arg Asp
            435                 440                 445

Ile Gln Asn Ile Asp Ala Leu Leu His Gln Ser Ile Gly Ser Thr Leu
450                 455                 460

Tyr Asn Lys Ile Tyr Leu Tyr Glu Asn Met Asn Ile Asn Asn Leu Thr
465                 470                 475                 480

Ala Thr Leu Gly Ala Asp Leu Val Asp Ser Thr Asp Asn Thr Lys Ile
                485                 490                 495

Asn Arg Gly Ile Phe Asn Glu Phe Lys Lys Asn Phe Lys Tyr Ser Ile
            500                 505                 510

Ser Ser Asn Tyr Met Ile Val Asp Ile Asn Glu Arg Pro Ala Leu Asp
            515                 520                 525

Asn Glu Arg Leu Lys Trp Arg Ile Gln Leu Ser Pro Asp Thr Arg Ala
530                 535                 540

Gly Tyr Leu Glu Asn Gly Lys Leu Ile Leu Gln Arg Asn Ile Gly Leu
545                 550                 555                 560

Glu Ile Lys Asp Val Gln Ile Ile Lys Gln Ser Glu Lys Glu Tyr Ile
                565                 570                 575

Arg Ile Asp Ala Lys Val Val Pro Lys Ser Lys Ile Asp Thr Lys Ile
            580                 585                 590

Gln Glu Ala Gln Leu Asn Ile Asn Gln Glu Trp Asn Lys Ala Leu Gly
            595                 600                 605

Leu Pro Lys Tyr Thr Lys Leu Ile Thr Phe Asn Val His Asn Arg Tyr
    610                 615                 620

Ala Ser Asn Ile Val Glu Ser Ala Tyr Leu Ile Leu Asn Glu Trp Lys
625                 630                 635                 640

Asn Asn Ile Gln Ser Asp Leu Ile Lys Lys Val Thr Asn Tyr Leu Val
                645                 650                 655

Asp Gly Asn Gly Arg Phe Val Phe Thr Asp Ile Thr Leu Pro Asn Ile
            660                 665                 670

Ala Glu Gln Tyr Thr His Gln Asp Glu Ile Tyr Glu Gln Val His Ser
```

```
              675                 680                 685
Lys Gly Leu Tyr Val Pro Glu Ser Arg Ser Ile Leu Leu His Gly Pro
    690                 695                 700

Ser Lys Gly Val Glu Leu Arg Asn Asp Ser Glu Gly Phe Ile His Glu
705                 710                 715                 720

Phe Gly His Ala Val Asp Asp Tyr Ala Gly Tyr Leu Leu Asp Lys Asn
                725                 730                 735

Gln Ser Asp Leu Val Thr Asn Ser Lys Lys Phe Ile Asp Ile Phe Lys
            740                 745                 750

Glu Glu Gly Ser Asn Leu Thr Ser Tyr Gly Arg Thr Asn Glu Ala Glu
        755                 760                 765

Phe Phe Ala Glu Ala Phe Arg Leu Met His Ser Thr Asp His Ala Glu
    770                 775                 780

Arg Leu Lys Val Gln Lys Asn Ala Pro Lys Thr Phe Gln Phe Ile Asn
785                 790                 795                 800

Asp Gln Ile Lys Phe Ile Ile Asn Ser
                805

<210> SEQ ID NO 3
<211> LENGTH: 432
<212> TYPE: PRT
<213> ORGANISM: B. anthracis

<400> SEQUENCE: 3

Ala Gly Ala Thr Cys Thr Ala Gly Ala Gly Ala Thr Ala Ala Gly Ala
1               5                   10                  15

Gly Ala Thr Thr Thr Cys Ala Thr Thr Ala Thr Gly Ala Thr Ala Gly
            20                  25                  30

Ala Ala Ala Cys Ala Ala Cys Ala Thr Thr Gly Cys Thr Gly Thr Thr
        35                  40                  45

Gly Gly Ala Gly Cys Thr Gly Ala Thr Gly Ala Ala Thr Cys Thr Gly
    50                  55                  60

Thr Thr Gly Thr Thr Ala Ala Gly Gly Ala Gly Gly Cys Thr Cys Ala
65                  70                  75                  80

Thr Ala Gly Ala Gly Ala Gly Gly Thr Thr Ala Thr Thr Ala Ala Cys
                85                  90                  95

Thr Cys Thr Thr Cys Thr Ala Cys Thr Gly Ala Gly Gly Gly Ala Cys
            100                 105                 110

Thr Thr Thr Thr Gly Cys Thr Thr Ala Ala Cys Ala Thr Thr Gly Ala
        115                 120                 125

Thr Ala Ala Gly Gly Ala Thr Ala Thr Thr Ala Gly Ala Ala Ala Gly
    130                 135                 140

Ala Thr Thr Cys Thr Thr Thr Cys Thr Gly Gly Ala Thr Ala Thr Ala
145                 150                 155                 160

Thr Thr Gly Thr Thr Gly Ala Gly Ala Thr Gly Ala Gly Gly Thr Ala
                165                 170                 175

Thr Ala Cys Thr Gly Ala Gly Gly Ala Cys Thr Thr Ala Ala Thr Gly
            180                 185                 190

Gly Ala Gly Gly Thr Ala Thr Thr Ala Cys Gly Ala Thr Ala
        195                 200                 205

Gly Ala Thr Ala Thr Gly Ala Thr Ala Thr Gly Cys Thr Thr Ala Ala
    210                 215                 220

Cys Ala Thr Thr Cys Thr Thr Cys Thr Thr Ala Gly Ala
225                 230                 235                 240

Cys Ala Ala Gly Ala Thr Gly Gly Ala Ala Ala Gly Ala Cys Thr Thr
```

|     |     |     |     | 245 |     |     |     | 250 |     |     |     | 255 |     |     |
| --- | --- | --- | --- | --- | --- | --- | --- | --- | --- | --- | --- | --- | --- | --- |
| Thr | Thr | Ala | Thr | Thr | Gly | Ala | Thr | Thr | Thr | Ala | Ala | Gly | Ala | Ala |
|     |     |     | 260 |     |     |     |     | 265 |     |     |     |     | 270 |     |
| Gly | Thr | Ala | Thr | Ala | Ala | Cys | Gly | Ala | Thr | Ala | Gly | Thr | Thr | Gly |
|     |     |     | 275 |     |     |     |     | 280 |     |     |     |     | 285 |     |
| Cys | Cys | Ala | Cys | Thr | Thr | Thr | Ala | Thr | Ala | Thr | Thr | Cys | Thr | Ala |
|     |     |     | 290 |     |     |     |     | 295 |     |     |     |     | 300 |     |
| Ala | Cys | Cys | Cys | Ala | Ala | Ala | Cys | Thr | Ala | Thr | Ala | Ala | Gly | Thr |
| 305 |     |     |     |     | 310 |     |     |     |     | 315 |     |     |     | 320 |
| Thr | Ala | Ala | Cys | Gly | Thr | Thr | Ala | Thr | Gly | Cys | Thr | Gly | Thr | Thr |
|     |     |     |     | 325 |     |     |     |     | 330 |     |     |     |     | 335 |
| Ala | Cys | Thr | Ala | Ala | Gly | Gly | Ala | Gly | Ala | Ala | Cys | Ala | Cys | Thr | Ala |
|     |     |     |     | 340 |     |     |     |     | 345 |     |     |     |     | 350 |     |
| Thr | Thr | Ala | Thr | Thr | Ala | Ala | Cys | Cys | Cys | Ala | Thr | Cys | Thr | Gly | Ala |
|     |     |     |     | 355 |     |     |     |     | 360 |     |     |     |     | 365 |     |
| Gly | Ala | Ala | Cys | Gly | Gly | Ala | Gly | Ala | Thr | Ala | Cys | Thr | Thr | Cys | Thr |
|     |     |     | 370 |     |     |     |     | 375 |     |     |     |     | 380 |     |     |
| Ala | Cys | Thr | Ala | Ala | Cys | Gly | Gly | Thr | Ala | Thr | Thr | Ala | Ala | Gly | Ala |
| 385 |     |     |     |     | 390 |     |     |     |     | 395 |     |     |     | 400 |     |
| Ala | Gly | Ala | Thr | Thr | Cys | Thr | Thr | Ala | Thr | Thr | Thr | Thr | Cys | Thr | Cys |
|     |     |     |     | 405 |     |     |     |     | 410 |     |     |     |     | 415 |     |
| Thr | Ala | Ala | Gly | Ala | Ala | Gly | Gly | Ala | Ala | Gly | Cys | Thr | Thr |     |     |
|     |     |     | 420 |     |     |     |     | 425 |     |     |     |     | 430 |     |     |

<210> SEQ ID NO 4
<211> LENGTH: 140
<212> TYPE: PRT
<213> ORGANISM: B. anthracis

<400> SEQUENCE: 4

| Arg | Asp | Lys | Arg | Phe | His | Tyr | Asp | Arg | Asn | Asn | Ile | Ala | Val | Gly | Ala |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Asp | Glu | Ser | Val | Val | Lys | Glu | Ala | His | Arg | Glu | Val | Ile | Asn | Ser | Ser |
|     |     |     | 20  |     |     |     |     | 25  |     |     |     |     | 30  |     |     |
| Thr | Glu | Gly | Leu | Leu | Leu | Asn | Ile | Asp | Lys | Asp | Ile | Arg | Lys | Ile | Leu |
|     |     | 35  |     |     |     |     | 40  |     |     |     |     | 45  |     |     |     |
| Ser | Gly | Tyr | Ile | Val | Glu | Ile | Glu | Asp | Thr | Glu | Gly | Leu | Lys | Glu | Val |
|     | 50  |     |     |     |     | 55  |     |     |     |     | 60  |     |     |     |     |
| Ile | Asn | Asp | Arg | Tyr | Asp | Met | Leu | Asn | Ile | Ser | Ser | Leu | Arg | Gln | Asp |
| 65  |     |     |     |     | 70  |     |     |     |     | 75  |     |     |     |     | 80  |
| Gly | Lys | Thr | Phe | Ile | Asp | Phe | Lys | Lys | Tyr | Asn | Asp | Lys | Leu | Pro | Leu |
|     |     |     |     | 85  |     |     |     |     | 90  |     |     |     |     | 95  |     |
| Tyr | Ile | Ser | Asn | Pro | Asn | Tyr | Lys | Val | Asn | Val | Tyr | Ala | Val | Thr | Lys |
|     |     |     | 100 |     |     |     |     | 105 |     |     |     |     | 110 |     |     |
| Glu | Asn | Thr | Ile | Ile | Asn | Pro | Ser | Glu | Asn | Gly | Asp | Thr | Ser | Thr | Asn |
|     |     |     | 115 |     |     |     |     | 120 |     |     |     |     | 125 |     |     |
| Gly | Ile | Lys | Lys | Ile | Leu | Ile | Phe | Ser | Lys | Lys | Gly |     |     |     |     |
|     | 130 |     |     |     |     | 135 |     |     |     |     | 140 |     |     |     |     |

<210> SEQ ID NO 5
<211> LENGTH: 708
<212> TYPE: PRT
<213> ORGANISM: B. anthracis

<400> SEQUENCE: 5

| Ala | Gly | Ala | Thr | Cys | Thr | Gly | Cys | Thr | Gly | Gly | Ala | Gly | Gly | Thr | Cys |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |

-continued

```
Ala Thr Gly Gly Ala Gly Ala Thr Gly Thr Thr Gly Gly Ala Ala Thr
            20                  25                  30

Gly Cys Ala Thr Gly Thr Thr Ala Ala Gly Gly Ala Gly Ala Ala Gly
        35                  40                  45

Gly Ala Gly Ala Ala Gly Ala Ala Cys Ala Ala Gly Gly Ala Thr Gly
    50                  55                  60

Ala Gly Ala Ala Cys Ala Ala Gly Ala Gly Ala Ala Ala Gly Gly Ala
65                  70                  75                  80

Thr Gly Ala Gly Gly Ala Gly Ala Gly Ala Ala Ala Cys Ala Ala Gly
                85                  90                  95
Ala Cys Thr Cys Ala Ala Gly Ala Gly Gly Ala Gly Cys Ala Thr Cys
            100                 105                 110

Thr Thr Ala Ala Gly Gly Ala Gly Ala Thr Thr Ala Thr Gly Ala Ala
        115                 120                 125
Gly Cys Ala Thr Ala Thr Thr Gly Thr Thr Ala Ala Gly Ala Thr Thr
    130                 135                 140

Gly Ala Ala Gly Thr Thr Ala Ala Gly Gly Gly Ala Gly Ala Ala Gly
145                 150                 155                 160

Ala Gly Gly Cys Thr Gly Thr Thr Ala Ala Gly Ala Ala Gly Gly Ala
                165                 170                 175
Ala Gly Cys Thr Gly Cys Ala Gly Ala Gly Ala Ala Gly Thr Thr Gly
            180                 185                 190

Cys Thr Thr Gly Ala Ala Ala Ala Gly Gly Thr Thr Cys Cys Ala Thr
        195                 200                 205

Cys Thr Gly Ala Thr Gly Thr Thr Cys Thr Thr Gly Ala Gly Ala Thr
    210                 215                 220

Gly Thr Ala Thr Ala Ala Gly Gly Cys Thr Ala Thr Thr Gly Gly Ala
225                 230                 235                 240

Gly Gly Ala Ala Ala Gly Ala Thr Ala Thr Ala Thr Ala Thr Thr Gly
                245                 250                 255
Thr Thr Gly Ala Thr Gly Gly Ala Gly Ala Thr Ala Thr Thr Ala Cys
            260                 265                 270

Thr Ala Ala Gly Cys Ala Thr Ala Thr Thr Thr Cys Thr Cys Thr Thr
        275                 280                 285
Gly Ala Gly Gly Cys Thr Cys Thr Thr Thr Cys Thr Gly Ala Gly Gly
    290                 295                 300

Ala Thr Ala Ala Gly Ala Ala Gly Ala Ala Gly Ala Thr Thr Ala Ala
305                 310                 315                 320

Gly Gly Ala Thr Ala Thr Ala Thr Ala Thr Gly Gly Ala Ala Ala Gly
                325                 330                 335

Gly Ala Thr Gly Cys Thr Cys Thr Thr Thr Thr Gly Cys Ala Thr Gly
            340                 345                 350

Ala Gly Cys Ala Thr Thr Ala Thr Gly Thr Thr Thr Ala Thr Gly Cys
        355                 360                 365

Thr Ala Ala Gly Gly Ala Gly Gly Gly Ala Thr Ala Thr Gly Ala Gly
    370                 375                 380

Cys Cys Ala Gly Thr Thr Cys Thr Thr Gly Thr Thr Ala Thr Thr Cys
385                 390                 395                 400
Ala Ala Thr Cys Thr Thr Cys Thr Gly Ala Ala Gly Ala Thr Thr Ala
                405                 410                 415
Thr Gly Thr Thr Gly Ala Gly Ala Ala Cys Ala Cys Thr Gly Ala Gly
            420                 425                 430

Ala Ala Gly Gly Cys Thr Cys Thr Thr Ala Ala Cys Gly Thr Thr Thr
```

```
                435                 440                 445
Ala Thr Thr Ala Thr Gly Ala Gly Ala Thr Gly Gly Ala Ala Ala
            450                 455                 460
Gly Ala Thr Thr Cys Thr Thr Cys Thr Ala Gly Ala Gly Ala Thr
465                 470                 475                 480
Ala Thr Thr Cys Thr Thr Thr Cys Thr Ala Ala Gly Ala Thr Thr Ala
                485                 490                 495
Ala Cys Cys Ala Ala Cys Cys Ala Thr Ala Thr Cys Ala Ala Ala
                500                 505                 510
Gly Thr Thr Thr Cys Thr Thr Gly Ala Thr Gly Thr Thr Cys Thr
            515                 520                 525
Ala Ala Cys Ala Cys Thr Ala Thr Thr Ala Ala Gly Ala Ala Cys Gly
            530                 535                 540
Cys Thr Thr Cys Thr Gly Ala Thr Thr Cys Thr Gly Ala Thr Gly Gly
545                 550                 555                 560
Ala Cys Ala Ala Gly Ala Thr Thr Thr Gly Thr Thr Gly Thr Thr Thr
                565                 570                 575
Ala Cys Thr Ala Ala Cys Cys Ala Ala Cys Thr Thr Ala Ala Gly Gly
                580                 585                 590
Ala Gly Cys Ala Thr Cys Cys Ala Ala Cys Thr Gly Ala Thr Thr Thr
            595                 600                 605
Thr Thr Cys Thr Gly Thr Thr Gly Ala Gly Thr Thr Thr Cys Thr Thr
            610                 615                 620
Gly Ala Gly Cys Ala Ala Ala Cys Thr Cys Thr Ala Ala Thr Gly
625                 630                 635                 640
Ala Gly Gly Thr Thr Cys Ala Ala Gly Ala Gly Gly Thr Thr Thr Thr
                645                 650                 655
Thr Gly Cys Thr Ala Ala Gly Gly Cys Thr Thr Thr Thr Gly Cys Thr
            660                 665                 670
Thr Ala Thr Thr Ala Thr Ala Thr Thr Gly Ala Gly Cys Cys Ala Cys
            675                 680                 685
Ala Ala Cys Ala Thr Ala Gly Ala Gly Ala Thr Gly Thr Thr Cys Thr
            690                 695                 700
Thr Cys Ala Ala
705

<210> SEQ ID NO 6
<211> LENGTH: 254
<212> TYPE: PRT
<213> ORGANISM: B. anthracis

<400> SEQUENCE: 6

Ala Gly Gly His Gly Asp Val Gly Met His Val Lys Glu Lys Glu Lys
1               5                   10                  15
Asn Lys Asp Glu Asn Lys Arg Lys Asp Glu Glu Arg Asn Lys Thr Gln
            20                  25                  30
Glu Glu His Leu Lys Glu Ile Met Lys His Ile Val Lys Ile Glu Val
        35                  40                  45
Lys Gly Glu Glu Ala Val Lys Lys Glu Ala Ala Glu Lys Leu Leu Glu
    50                  55                  60
Lys Val Pro Ser Asp Val Leu Glu Met Tyr Lys Ala Ile Gly Gly Lys
65                  70                  75                  80
Ile Tyr Ile Val Asp Gly Asp Ile Thr Lys His Ile Ser Leu Glu Ala
                85                  90                  95
Leu Ser Glu Asp Lys Lys Lys Ile Lys Asp Ile Tyr Gly Lys Asp Ala
```

```
                    100                 105                 110
Leu Leu His Glu His Tyr Val Tyr Ala Lys Glu Gly Tyr Glu Pro Val
            115                 120                 125
Leu Val Ile Gln Ser Ser Glu Asp Tyr Val Glu Asn Thr Glu Lys Ala
        130                 135                 140
Leu Asn Val Tyr Tyr Glu Ile Gly Lys Ile Leu Ser Arg Asp Ile Leu
145                 150                 155                 160
Ser Lys Ile Asn Gln Pro Tyr Gln Lys Phe Leu Asp Val Leu Asn Thr
                165                 170                 175
Ile Lys Asn Ala Ser Asp Ser Asp Gly Gln Asp Leu Leu Phe Thr Asn
            180                 185                 190
Gln Leu Lys Glu His Pro Thr Asp Phe Ser Val Glu Phe Leu Glu Gln
        195                 200                 205
Asn Ser Asn Glu Val Gln Glu Val Phe Ala Lys Ala Phe Ala Tyr Tyr
    210                 215                 220
Ile Glu Pro Gln His Arg Asp Val Leu Gln Leu Tyr Ala Pro Glu Ala
225                 230                 235                 240
Phe Asn Tyr Met Asp Lys Phe Asn Glu Gln Glu Ile Asn Leu
                245                 250

<210> SEQ ID NO 7
<211> LENGTH: 717
<212> TYPE: PRT
<213> ORGANISM: C. thermocellum lichenase

<400> SEQUENCE: 7

Gly Gly Ala Thr Cys Cys Thr Thr Ala Thr Thr Ala Ala Ala
1               5                   10                  15
Thr Gly Gly Gly Ala Gly Gly Thr Thr Cys Thr Thr Ala Thr Cys Cys
            20                  25                  30
Ala Thr Ala Thr Ala Ala Gly Thr Cys Thr Gly Gly Thr Gly Ala Gly
        35                  40                  45
Thr Ala Thr Ala Gly Ala Ala Cys Thr Ala Ala Gly Thr Cys Thr Thr
    50                  55                  60
Thr Cys Thr Thr Thr Gly Gly Ala Thr Ala Thr Gly Gly Thr Thr Ala
65                  70                  75                  80
Thr Thr Ala Thr Gly Ala Ala Gly Thr Thr Ala Gly Gly Ala Thr Gly
                85                  90                  95
Ala Ala Gly Gly Cys Thr Gly Cys Ala Ala Gly Ala Ala Cys Thr Gly
            100                 105                 110
Thr Thr Gly Gly Ala Ala Thr Thr Gly Thr Thr Thr Cys Thr Thr Cys
        115                 120                 125
Thr Thr Thr Cys Thr Thr Thr Ala Cys Thr Thr Ala Thr Ala Cys Thr
    130                 135                 140
Gly Gly Ala Cys Cys Ala Thr Cys Thr Gly Ala Thr Ala Ala Cys Ala
145                 150                 155                 160
Ala Cys Cys Cys Ala Thr Gly Gly Ala Thr Gly Ala Gly Ala Thr
                165                 170                 175
Thr Gly Ala Thr Ala Thr Thr Gly Ala Thr Thr Thr Cys Thr Thr
            180                 185                 190
Gly Gly Ala Ala Ala Gly Gly Ala Thr Ala Cys Thr Ala Cys Thr Ala
        195                 200                 205
Ala Gly Gly Thr Thr Cys Ala Ala Thr Cys Ala Ala Cys Thr Gly
    210                 215                 220
Gly Thr Ala Thr Ala Ala Gly Ala Ala Thr Gly Gly Thr Gly Thr Thr
```

-continued

```
225                 230                 235                 240

Gly Gly Thr Gly Gly Ala Ala Ala Cys Gly Ala Gly Thr Ala Thr Cys
                245                 250                 255
Thr Thr Cys Ala Thr Ala Ala Cys Cys Thr Thr Gly Gly Ala Thr Thr
            260                 265                 270

Thr Gly Ala Thr Gly Cys Thr Thr Cys Thr Cys Ala Ala Gly Ala Thr
        275                 280                 285

Thr Thr Thr Cys Ala Thr Ala Cys Thr Thr Ala Thr Gly Gly Thr Thr
    290                 295                 300

Thr Thr Gly Ala Gly Thr Gly Gly Ala Gly Ala Cys Cys Ala Gly Ala
305                 310                 315                 320

Thr Thr Ala Thr Ala Thr Thr Gly Ala Thr Thr Thr Thr Thr Ala Thr
                325                 330                 335
Gly Thr Thr Gly Ala Thr Gly Gly Ala Ala Ala Gly Ala Ala Gly Gly
            340                 345                 350

Thr Thr Thr Ala Thr Ala Gly Ala Gly Gly Thr Ala Cys Thr Ala Gly
        355                 360                 365

Ala Ala Ala Cys Ala Thr Thr Cys Cys Ala Gly Thr Thr Ala Cys Thr
    370                 375                 380

Cys Cys Thr Gly Gly Ala Ala Ala Gly Ala Thr Thr Ala Thr Gly Ala
385                 390                 395                 400
Thr Gly Ala Ala Thr Cys Thr Thr Thr Gly Gly Cys Cys Ala Gly Gly
                405                 410                 415
Ala Ala Thr Thr Gly Gly Thr Gly Thr Thr Gly Ala Thr Gly Ala Ala
            420                 425                 430

Thr Gly Gly Cys Thr Thr Gly Gly Thr Ala Gly Ala Thr Ala Thr Gly
        435                 440                 445

Ala Thr Gly Gly Ala Ala Gly Ala Ala Cys Thr Cys Cys Ala Cys Thr
    450                 455                 460

Thr Cys Ala Ala Gly Cys Thr Gly Ala Gly Thr Ala Thr Gly Ala Gly
465                 470                 475                 480
Thr Ala Thr Gly Thr Thr Ala Ala Gly Thr Ala Thr Thr Ala Thr Cys
                485                 490                 495

Cys Ala Ala Ala Cys Gly Gly Thr Ala Gly Ala Thr Cys Thr Gly Ala
            500                 505                 510

Ala Thr Thr Cys Ala Ala Gly Cys Thr Thr Gly Thr Thr Gly Thr Thr
        515                 520                 525

Ala Ala Thr Ala Cys Thr Cys Cys Ala Thr Thr Thr Gly Thr Thr Gly
    530                 535                 540

Cys Thr Gly Thr Thr Thr Thr Cys Thr Cys Thr Ala Ala Cys Thr Thr
545                 550                 555                 560

Thr Gly Ala Thr Thr Cys Thr Thr Cys Thr Cys Ala Ala Thr Gly Gly
                565                 570                 575

Gly Ala Ala Ala Ala Gly Gly Cys Thr Gly Ala Thr Thr Gly Gly Gly
            580                 585                 590

Cys Thr Ala Ala Cys Gly Gly Thr Thr Cys Thr Gly Thr Thr Thr Thr
        595                 600                 605

Thr Ala Ala Cys Thr Gly Thr Gly Thr Thr Thr Gly Gly Ala Ala Gly
    610                 615                 620

Cys Cys Ala Thr Cys Thr Cys Ala Ala Gly Thr Thr Ala Cys Thr Thr
625                 630                 635                 640

Thr Thr Thr Cys Thr Ala Ala Cys Gly Gly Ala Ala Ala Gly Ala Thr
                645                 650                 655
```

```
Gly Ala Thr Thr Cys Thr Ala Cys Thr Thr Gly Gly Ala Thr
            660                 665                 670
Ala Gly Ala Gly Ala Gly Thr Ala Thr Gly Thr Cys Gly Ala Cys Cys
            675                 680                 685
Ala Thr Cys Ala Thr Cys Ala Thr Cys Ala Thr Cys Ala Thr Cys Ala
            690                 695                 700
Thr Thr Gly Ala Cys Thr Cys Gly Ala Gly Cys Thr Cys
705                 710                 715

<210> SEQ ID NO 8
<211> LENGTH: 230
<212> TYPE: PRT
<213> ORGANISM: C. thermocellum lichenase

<400> SEQUENCE: 8

Met Gly Gly Ser Tyr Pro Tyr Lys Ser Gly Glu Tyr Arg Thr Lys Ser
1               5                   10                  15
Phe Phe Gly Tyr Gly Tyr Glu Val Arg Met Lys Ala Ala Lys Asn
                20                  25                  30
Val Gly Ile Val Ser Ser Phe Phe Thr Tyr Thr Gly Pro Ser Asp Asn
            35                  40                  45
Asn Pro Trp Asp Glu Ile Asp Ile Glu Phe Leu Gly Lys Asp Thr Thr
50                  55                  60
Lys Val Gln Phe Asn Trp Tyr Lys Asn Gly Val Gly Gly Asn Glu Tyr
65                  70                  75                  80
Leu His Asn Leu Gly Phe Asp Ala Ser Gln Asp Phe His Thr Tyr Gly
                85                  90                  95
Phe Glu Trp Arg Pro Asp Tyr Ile Asp Phe Tyr Val Asp Gly Lys Lys
            100                 105                 110
Val Tyr Arg Gly Thr Arg Asn Ile Pro Val Thr Pro Gly Lys Ile Met
            115                 120                 125
Met Asn Leu Trp Pro Gly Ile Gly Val Asp Glu Trp Leu Gly Arg Tyr
130                 135                 140
Asp Gly Arg Thr Pro Leu Gln Ala Glu Tyr Glu Tyr Val Lys Tyr Tyr
145                 150                 155                 160
Pro Asn Gly Arg Ser Glu Phe Lys Leu Val Val Asn Thr Pro Phe Val
                165                 170                 175
Ala Val Phe Ser Asn Phe Asp Ser Ser Gln Trp Glu Lys Ala Asp Trp
            180                 185                 190
Ala Asn Gly Ser Val Phe Asn Cys Val Trp Lys Pro Ser Gln Val Thr
            195                 200                 205
Phe Ser Asn Gly Lys Met Ile Leu Thr Leu Asp Arg Glu Tyr Val Asp
210                 215                 220
His His His His His His
225                 230

<210> SEQ ID NO 9
<211> LENGTH: 822
<212> TYPE: PRT
<213> ORGANISM: C. thermocellum lichenase

<400> SEQUENCE: 9

Gly Gly Ala Thr Cys Cys Thr Thr Ala Ala Thr Thr Ala Ala Ala
1               5                   10                  15
Thr Gly Gly Gly Ala Thr Thr Gly Thr Cys Thr Cys Thr Thr
            20                  25                  30
Thr Thr Cys Ala Cys Ala Ala Thr Thr Gly Cys Cys Thr Thr Cys Ala
```

```
                35                  40                  45
Thr Thr Thr Cys Thr Thr Cys Thr Thr Gly Thr Cys Thr Cys Thr Ala
            50                  55                  60
Cys Ala Cys Thr Thr Cys Thr Cys Thr Thr Ala Thr Thr Cys Cys Thr
65                  70                  75                  80
Ala Gly Thr Ala Ala Thr Ala Thr Cys Cys Ala Cys Thr Cys Thr
                85                  90                  95
Thr Gly Cys Cys Gly Thr Gly Cys Cys Cys Ala Ala Ala Thr Gly
            100                 105                 110
Gly Ala Gly Gly Thr Thr Cys Thr Thr Ala Thr Cys Cys Ala Thr Ala
                115                 120                 125
Thr Ala Ala Gly Thr Cys Thr Gly Gly Thr Gly Ala Gly Thr Ala Thr
    130                 135                 140
Ala Gly Ala Ala Cys Thr Ala Ala Gly Thr Cys Thr Thr Thr Cys Thr
145                 150                 155                 160
Thr Thr Gly Gly Ala Thr Ala Thr Gly Gly Thr Thr Ala Thr Thr Ala
                165                 170                 175
Thr Gly Ala Ala Gly Th

```
Cys Ala Thr Thr Cys Cys Ala Gly Thr Thr Ala Cys Thr Cys Thr
465                 470                 475                 480

Gly Gly Ala Ala Gly Ala Thr Thr Ala Thr Gly Ala Thr Gly Ala
                485                 490                 495

Ala Thr Cys Thr Thr Thr Gly Gly Cys Cys Ala Gly Gly Ala Ala
            500                 505                 510

Thr Gly Gly Thr Gly Thr Thr Gly Ala Thr Gly Ala Ala Thr Gly
        515                 520                 525

Cys Thr Thr Gly Gly Thr Ala Gly Ala Thr Ala Gly Ala Thr Gly
    530                 535                 540

Gly Ala Ala Gly Ala Ala Cys Cys Ala Cys Thr Thr Cys Thr Ala
545                 550                 555                 560

Ala Gly Cys Thr Gly Ala Gly Thr Ala Thr Gly Ala Gly Thr Ala
                565                 570                 575

Gly Thr Thr Ala Ala Gly Thr Ala Thr Ala Thr Cys Cys Ala Ala
            580                 585                 590

Ala Cys Gly Gly Thr Ala Gly Ala Thr Cys Thr Gly Ala Thr Thr
        595                 600                 605

Cys Ala Ala Gly Cys Thr Thr Gly Thr Thr Gly Ala Thr Ala Thr
    610                 615                 620

Ala Cys Thr Cys Cys Ala Thr Thr Thr Gly Thr Thr Gly Cys Thr Gly
625                 630                 635                 640

Thr Thr Thr Thr Cys Thr Cys Thr Ala Ala Cys Thr Thr Gly Ala
                645                 650                 655

Thr Thr Cys Thr Thr Cys Thr Cys Ala Ala Thr Gly Gly Ala Ala
            660                 665                 670

Ala Ala Gly Gly Cys Thr Gly Ala Thr Gly Gly Gly Cys Thr Ala
        675                 680                 685

Ala Cys Gly Gly Thr Thr Cys Thr Gly Thr Thr Thr Thr Ala Ala
    690                 695                 700

Cys Thr Gly Thr Gly Thr Thr Thr Gly Gly Ala Ala Gly Cys Cys Ala
705                 710                 715                 720

Thr Cys Thr Cys Ala Ala Gly Thr Thr Ala Cys Thr Thr Thr Thr
                725                 730                 735

Cys Thr Ala Ala Cys Gly Gly Ala Ala Ala Gly Ala Thr Gly Ala Thr
            740                 745                 750

Thr Cys Thr Thr Ala Cys Thr Thr Thr Gly Gly Ala Thr Ala Gly Ala
        755                 760                 765

Gly Ala Gly Thr Ala Thr Gly Thr Cys Gly Ala Cys Cys Ala Thr Cys
    770                 775                 780

Ala Thr Cys Ala Thr Cys Ala Thr Cys Ala Thr Cys Ala Thr Ala Ala
785                 790                 795                 800

Gly Gly Ala Thr Gly Ala Ala Cys Thr Thr Gly Ala Cys Thr Cys
                805                 810                 815

Gly Ala Gly Cys Thr Cys
            820

<210> SEQ ID NO 10
<211> LENGTH: 265
<212> TYPE: PRT
<213> ORGANISM: C. thermocellum lichenase

<400> SEQUENCE: 10

Met Gly Phe Val Leu Phe Ser Gln Leu Pro Ser Phe Leu Leu Val Ser
1               5                   10                  15
```

```
Thr Leu Leu Leu Phe Leu Val Ile Ser His Ser Cys Arg Ala Gln Asn
         20                  25                  30

Gly Gly Ser Tyr Pro Tyr Lys Ser Gly Glu Tyr Arg Thr Lys Ser Phe
             35                  40                  45

Phe Gly Tyr Gly Tyr Tyr Glu Val Arg Met Lys Ala Ala Lys Asn Val
 50                  55                  60

Gly Ile Val Ser Ser Phe Phe Thr Tyr Thr Gly Pro Ser Asp Asn Asn
 65                  70                  75                  80

Pro Trp Asp Glu Ile Asp Ile Glu Phe Leu Gly Lys Asp Thr Thr Lys
                 85                  90                  95

Val Gln Phe Asn Trp Tyr Lys Asn Gly Val Gly Gly Asn Glu Tyr Leu
                100                 105                 110

His Asn Leu Gly Phe Asp Ala Ser Gln Asp Phe His Thr Tyr Gly Phe
            115                 120                 125

Glu Trp Arg Pro Asp Tyr Ile Asp Phe Tyr Val Asp Gly Lys Lys Val
        130                 135                 140

Tyr Arg Gly Thr Arg Asn Ile Pro Val Thr Pro Gly Lys Ile Met Met
145                 150                 155                 160

Asn Leu Trp Pro Gly Ile Gly Val Asp Glu Trp Leu Gly Arg Tyr Asp
                165                 170                 175

Gly Arg Thr Pro Leu Gln Ala Glu Tyr Glu Tyr Val Lys Tyr Tyr Pro
            180                 185                 190

Asn Gly Arg Ser Glu Phe Lys Leu Val Val Asn Thr Pro Phe Val Ala
        195                 200                 205

Val Phe Ser Asn Phe Asp Ser Ser Gln Trp Glu Lys Ala Asp Trp Ala
    210                 215                 220

Asn Gly Ser Val Phe Asn Cys Val Trp Lys Pro Ser Gln Val Thr Phe
225                 230                 235                 240

Ser Asn Gly Lys Met Ile Leu Thr Leu Asp Arg Glu Tyr Val Asp His
                245                 250                 255

His His His His Lys Asp Glu Leu
            260                 265

<210> SEQ ID NO 11
<211> LENGTH: 1236
<212> TYPE: PRT
<213> ORGANISM: B. anthracis

<400> SEQUENCE: 11

Gly Gly Ala Thr Cys Cys Thr Thr Ala Ala Thr Thr Ala Ala Ala Ala
 1               5                  10                  15

Thr Gly Gly Gly Ala Thr Thr Thr Gly Thr Cys Thr Cys Thr Thr Thr
             20                  25                  30

Thr Thr Cys Ala Cys Ala Ala Thr Thr Gly Cys Cys Thr Cys Thr Ala
         35                  40                  45

Thr Thr Thr Cys Thr Thr Thr Cys Thr Thr Gly Thr Cys Thr Cys Thr
     50                  55                  60

Cys Ala Cys Thr Thr Cys Thr Cys Thr Thr Ala Thr Thr Cys Cys Thr
 65                  70                  75                  80

Ala Gly Thr Ala Ala Thr Ala Thr Cys Cys Cys Ala Cys Thr Cys Thr
                 85                  90                  95

Thr Gly Cys Cys Gly Thr Gly Cys Cys Cys Ala Ala Ala Ala Thr Gly
                100                 105                 110

Gly Ala Gly Gly Thr Thr Cys Thr Thr Ala Thr Cys Cys Ala Thr Ala
            115                 120                 125
```

```
Thr Ala Ala Gly Thr Cys Thr Gly Gly Thr Gly Ala Gly Thr Ala Thr
    130                 135                 140

Ala Gly Ala Ala Cys Thr Ala Ala Gly Thr Cys Thr Thr Thr Cys Thr
145                 150                 155                 160

Thr Thr Gly Gly Ala Thr Ala Thr Gly Gly Thr Thr Ala Thr Thr Ala
                165                 170                 175

Thr Gly Ala Ala Gly Thr Thr Ala Gly Gly Ala Thr Gly Ala Ala Gly
            180                 185                 190

Gly Cys Thr Gly Cys Ala Ala Ala Gly Ala Ala Cys Gly Thr Thr Gly
        195                 200                 205

Gly Ala Ala Thr Thr Gly Thr Thr Thr Cys Thr Thr Cys Thr Thr Thr
    210                 215                 220

Cys Thr Thr Thr Ala Cys Thr Thr Ala Thr Ala Cys Thr Gly Gly Ala
225                 230                 235                 240

Cys Cys Ala Thr Cys Thr Gly Ala Thr Ala Ala Cys Ala Ala Cys Cys
                245                 250                 255

Cys Ala Thr Gly Gly Gly Ala Thr Gly Ala Gly Ala Thr Thr Gly Ala
            260                 265                 270

Thr Ala Thr Thr Gly Ala Gly Thr Thr Thr Cys Thr Thr Gly Gly Ala
        275                 280                 285

Ala Ala Gly Gly Ala Thr Ala Cys Thr Ala Cys Thr Ala Ala Gly Gly
    290                 295                 300

Thr Thr Cys Ala Ala Thr Thr Cys Ala Ala Cys Thr Gly Gly Thr Ala
305                 310                 315                 320

Thr Ala Ala Gly Ala Ala Thr Gly Gly Thr Gly Thr Thr Gly Gly Thr
                325                 330                 335

Gly Gly Ala Ala Ala Cys Gly Ala Gly Thr Ala Thr Cys Thr Thr Cys
            340                 345                 350

Ala Thr Ala Ala Cys Cys Thr Thr Gly Gly Ala Thr Thr Thr Gly Ala
        355                 360                 365

Thr Gly Cys Thr Thr Cys Thr Cys Ala Ala Gly Ala Thr Thr Thr Thr
    370                 375                 380

Cys Ala Thr Ala Cys Thr Thr Ala Thr Gly Gly Thr Thr Thr Thr Gly
385                 390                 395                 400

Ala Gly Thr Gly Gly Ala Gly Ala Cys Cys Ala Gly Ala Thr Thr Ala
                405                 410                 415

Thr Ala Thr Thr Gly Ala Thr Thr Thr Thr Thr Ala Thr Gly Thr Thr
            420                 425                 430

Gly Ala Thr Gly Gly Ala Ala Ala Gly Ala Ala Gly Gly Thr Thr Thr
        435                 440                 445

Ala Thr Ala Gly Ala Gly Gly Thr Ala Cys Thr Ala Gly Ala Ala Ala
    450                 455                 460

Cys Ala Thr Thr Cys Cys Ala Gly Thr Thr Ala Cys Thr Cys Cys Thr
465                 470                 475                 480

Gly Gly Ala Ala Ala Gly Ala Thr Thr Ala Thr Gly Ala Thr Gly Ala
                485                 490                 495

Ala Thr Cys Thr Thr Thr Gly Gly Cys Cys Ala Gly Gly Ala Ala Thr
            500                 505                 510

Thr Gly Gly Thr Gly Thr Thr Gly Ala Thr Gly Ala Ala Thr Gly Gly
        515                 520                 525

Cys Thr Thr Gly Gly Thr Ala Gly Ala Thr Ala Thr Gly Ala Thr Gly
    530                 535                 540

Gly Ala Ala Gly Ala Ala Cys Thr Cys Cys Ala Cys Thr Thr Cys Ala
545                 550                 555                 560

```
Ala Gly Cys Thr Gly Ala Gly Thr Ala Thr Gly Ala Thr
                565                 570                 575
Gly Thr Thr Ala Ala Gly Thr Ala Thr Ala Thr Cys Cys Ala Ala
        580                 585                 590
Ala Cys Gly Gly Thr Ala Gly Ala Thr Cys Thr Ala Gly Ala Gly Ala
        595                 600                 605
Thr Ala Ala Gly Ala Gly Ala Thr Thr Thr Cys Ala Thr Thr Ala Thr
        610                 615                 620
Gly Ala Thr Ala Gly Ala Ala Cys Ala Ala Cys Ala Thr Gly
625                 630                 635                 640
Cys Thr Gly Thr Thr Gly Gly Ala Gly Cys Thr Gly Ala Thr Gly Ala
                645                 650                 655
Ala Thr Cys Thr Gly Thr Thr Gly Thr Thr Ala Ala Gly Gly Ala Gly
                660                 665                 670
Gly Cys Thr Cys Ala Thr Ala Gly Ala Gly Ala Gly Thr Thr Ala
        675                 680                 685
Thr Thr Ala Ala Cys Thr Cys Thr Thr Cys Thr Ala Cys Thr Gly Ala
        690                 695                 700
Gly Gly Gly Ala Cys Thr Thr Thr Thr Gly Cys Thr Thr Ala Ala Cys
705                 710                 715                 720
Ala Thr Thr Gly Ala Thr Ala Ala Gly Gly Ala Thr Ala Thr Thr Ala
                725                 730                 735
Gly Ala Ala Ala Gly Ala Thr Thr Cys Thr Thr Thr Cys Thr Gly Gly
                740                 745                 750
Ala Thr Ala Thr Ala Thr Thr Gly Thr Thr Gly Ala Gly Ala Thr Thr
        755                 760                 765
Gly Ala Gly Gly Ala Thr Ala Cys Thr Gly Ala Gly Gly Ala Cys
        770                 775                 780
Thr Thr Ala Ala Gly Gly Ala Gly Gly Thr Thr Ala Thr Thr Ala Ala
785                 790                 795                 800
Cys Gly Ala Thr Ala Gly Ala Thr Ala Thr Gly Ala Thr Ala Thr Gly
                805                 810                 815
Cys Thr Thr Ala Ala Cys Ala Thr Thr Thr Cys Thr Thr Cys Thr Cys
                820                 825                 830
Thr Thr Ala Gly Ala Cys Ala Ala Gly Ala Thr Gly Gly Ala Ala Ala
        835                 840                 845
Gly Ala Cys Thr Thr Thr Thr Ala Thr Thr Gly Ala Thr Thr Thr Thr
850                 855                 860
Ala Ala Gly Ala Ala Gly Thr Ala Thr Ala Ala Cys Gly Ala Thr Ala
865                 870                 875                 880
Ala Gly Thr Thr Gly Cys Cys Ala Cys Thr Thr Ala Thr Ala Thr
        885                 890                 895
Thr Thr Cys Thr Ala Ala Cys Cys Cys Ala Ala Ala Cys Thr Ala Thr
        900                 905                 910
Ala Ala Gly Gly Thr Thr Ala Ala Cys Gly Thr Thr Ala Thr Gly
        915                 920                 925
Cys Thr Gly Thr Thr Ala Cys Thr Ala Ala Gly Gly Ala Gly Ala Ala
        930                 935                 940
Cys Ala Cys Thr Ala Thr Thr Ala Thr Thr Ala Ala Cys Cys Cys Ala
945                 950                 955                 960
Thr Cys Thr Gly Ala Gly Ala Ala Cys Gly Gly Ala Gly Ala Thr Ala
        965                 970                 975
Cys Thr Thr Cys Thr Ala Cys Thr Ala Ala Cys Gly Gly Thr Ala Thr
```

```
                    980             985                990
Thr Ala Ala Gly Ala Ala Gly Ala  Thr Thr Cys Thr Thr  Ala Thr Thr
            995                  1000                 1005

Thr Thr  Cys Thr Cys Thr Ala  Thr Thr Gly Ala Ala Gly  Gly Gly Ala
    1010              1015                 1020

Ala Ala  Gly Cys Thr Thr Gly  Thr Thr Gly Thr Thr Gly  Thr Ala Ala Thr
    1025              1030                 1035

Ala Cys  Thr Cys Cys Ala Thr  Thr Thr Gly Thr Thr Thr  Gly Cys Thr
    1040              1045                 1050

Gly Thr  Thr Thr Thr Cys Thr  Cys Thr Ala Ala Cys  Thr Thr Thr
    1055              1060                 1065

Gly Ala  Thr Thr Cys Thr Thr  Cys Thr Cys Ala Ala  Thr Gly Gly
    1070              1075                 1080

Gly Ala  Ala Ala Ala Gly Gly  Cys Thr Gly Ala Thr  Thr Gly Gly
    1085              1090                 1095

Gly Cys  Thr Ala Ala Cys Gly  Gly Thr Thr Cys Thr  Gly Thr Thr
    1100              1105                 1110

Thr Thr  Thr Ala Ala Cys Thr  Gly Thr Gly Thr Thr  Thr Gly Gly
    1115              1120                 1125

Ala Ala  Gly Cys Cys Ala Thr  Cys Thr Cys Ala Ala  Gly Thr Thr
    1130              1135                 1140

Ala Cys  Thr Thr Thr Thr Thr  Cys Thr Ala Ala Cys  Gly Gly Ala
    1145              1150                 1155

Ala Ala  Gly Ala Thr Gly Ala  Thr Thr Cys Thr Thr  Ala Cys Thr
    1160              1165                 1170

Thr Thr  Gly Gly Ala Thr Ala  Gly Ala Gly Ala Gly  Thr Ala Thr
    1175              1180                 1185

Gly Thr  Cys Gly Ala Cys Cys  Ala Thr Cys Ala Thr  Cys Ala Thr
    1190              1195                 1200

Cys Ala  Thr Cys Ala Thr Cys  Ala Thr Ala Ala Gly  Gly Ala Thr
    1205              1210                 1215

Gly Ala  Ala Cys Thr Thr Thr  Gly Ala Cys Thr Cys  Gly Ala Gly
    1220              1225                 1230

Cys Thr  Cys
    1235

<210> SEQ ID NO 12
<211> LENGTH: 403
<212> TYPE: PRT
<213> ORGANISM: B. anthracis

<400> SEQUENCE: 12

Met Gly Phe Val Leu Phe Ser Gln Leu Pro Ser Phe Leu Leu Val Ser
1               5                   10                  15

Thr Leu Leu Phe Leu Val Ile Ser His Ser Cys Arg Ala Gln Asn
            20                  25                  30

Gly Gly Ser Tyr Pro Tyr Lys Ser Gly Glu Tyr Arg Thr Lys Ser Phe
        35                  40                  45

Phe Gly Tyr Gly Tyr Tyr Glu Val Arg Met Lys Ala Ala Lys Asn Val
    50                  55                  60

Gly Ile Val Ser Ser Phe Phe Tyr Thr Gly Pro Ser Asp Asn Asn
65                  70                  75                  80

Pro Trp Asp Glu Ile Asp Ile Glu Phe Leu Gly Lys Asp Thr Thr Lys
                85                  90                  95

Val Gln Phe Asn Trp Tyr Lys Asn Gly Val Gly Gly Asn Glu Tyr Leu
```

```
                100                 105                 110
His Asn Leu Gly Phe Asp Ala Ser Gln Asp Phe His Thr Tyr Gly Phe
            115                 120                 125

Glu Trp Arg Pro Asp Tyr Ile Asp Phe Tyr Val Asp Gly Lys Lys Val
130                 135                 140

Tyr Arg Gly Thr Arg Asn Ile Pro Val Thr Pro Gly Lys Ile Met Met
145                 150                 155                 160

Asn Leu Trp Pro Gly Ile Gly Val Asp Glu Trp Leu Gly Arg Tyr Asp
            165                 170                 175

Gly Arg Thr Pro Leu Gln Ala Glu Tyr Glu Val Lys Tyr Tyr Pro
            180                 185                 190

Asn Gly Arg Ser Arg Asp Lys Arg Phe His Tyr Asp Arg Asn Asn Ile
            195                 200                 205

Ala Val Gly Ala Asp Glu Ser Val Val Lys Glu Ala His Arg Glu Val
            210                 215                 220

Ile Asn Ser Ser Thr Glu Gly Leu Leu Leu Asn Ile Asp Lys Asp Ile
225                 230                 235                 240

Arg Lys Ile Leu Ser Gly Tyr Ile Val Glu Ile Glu Asp Thr Glu Gly
            245                 250                 255

Leu Lys Glu Val Ile Asn Asp Arg Tyr Asp Met Leu Asn Ile Ser Ser
            260                 265                 270

Leu Arg Gln Asp Gly Lys Thr Phe Ile Asp Phe Lys Lys Tyr Asn Asp
            275                 280                 285

Lys Leu Pro Leu Tyr Ile Ser Asn Pro Asn Tyr Lys Val Asn Val Tyr
            290                 295                 300

Ala Val Thr Lys Glu Asn Thr Ile Ile Asn Pro Ser Glu Asn Gly Asp
305                 310                 315                 320

Thr Ser Thr Asn Gly Ile Lys Lys Ile Leu Ile Phe Ser Lys Lys Gly
            325                 330                 335

Lys Leu Val Val Asn Thr Pro Phe Val Ala Val Phe Ser Asn Phe Asp
            340                 345                 350

Ser Ser Gln Trp Glu Lys Ala Asp Trp Ala Asn Gly Ser Val Phe Asn
            355                 360                 365

Cys Val Trp Lys Pro Ser Gln Val Thr Phe Ser Asn Gly Lys Met Ile
            370                 375                 380

Leu Thr Leu Asp Arg Glu Tyr Val Asp His His His His His His Lys
385                 390                 395                 400

Asp Glu Leu

<210> SEQ ID NO 13
<211> LENGTH: 1473
<212> TYPE: PRT
<213> ORGANISM: B. anthracis

<400> SEQUENCE: 13

Gly Gly Ala Thr Cys Cys Thr Thr Ala Ala Thr Ala Ala Ala Ala
1               5                   10                  15

Thr Gly Gly Gly Ala Gly Gly Thr Thr Cys Thr Thr Ala Thr Cys Cys
                20                  25                  30

Ala Thr Ala Thr Ala Ala Gly Thr Cys Thr Gly Gly Thr Gly Ala Gly
            35                  40                  45

Thr Ala Thr Ala Gly Ala Ala Cys Thr Ala Ala Gly Thr Cys Thr Thr
            50                  55                  60

Thr Cys Thr Thr Thr Gly Gly Ala Thr Ala Thr Gly Gly Thr Thr Ala
65                  70                  75                  80
```

-continued

```
Thr Thr Ala Thr Gly Ala Ala Gly Thr Ala Gly Gly Ala Thr Gly
                 85                  90                  95
Ala Ala Gly Gly Cys Thr Gly Cys Ala Ala Gly Ala Ala Cys Gly
                100                 105                 110
Thr Thr Gly Gly Ala Ala Thr Thr Gly Thr Thr Thr Cys Thr Cys
                115                 120                 125
Thr Thr Thr Cys Thr Thr Thr Ala Cys Thr Thr Ala Thr Ala Cys Thr
            130                 135                 140
Gly Gly Ala Cys Cys Ala Thr Cys Thr Gly Ala Thr Ala Ala Cys Ala
145                 150                 155                 160
Ala Cys Cys Cys Ala Thr Gly Gly Ala Thr Gly Ala Gly Ala Thr
                165                 170                 175
Thr Gly Ala Thr Ala Thr Thr Gly Ala Gly Thr Thr Thr Cys Thr Thr
            180                 185                 190
Gly Gly Ala Ala Ala Gly Gly Ala Thr Ala Cys Thr Ala Cys Thr Ala
            195                 200                 205
Ala Gly Gly Thr Thr Cys Ala Ala Thr Thr Cys Ala Ala Cys Thr Gly
210                 215                 220
Gly Thr Ala Thr Ala Ala Gly Ala Ala Thr Gly Thr Gly Thr Thr
225                 230                 235                 240
Gly Gly Thr Gly Gly Ala Ala Ala Cys Gly Ala Gly Thr Ala Thr Cys
            245                 250                 255
Thr Thr Cys Ala Thr Ala Ala Cys Cys Thr Gly Gly Ala Thr Thr
                260                 265                 270
Thr Gly Ala Thr Gly Cys Thr Thr Cys Thr Ala Ala Gly Ala Thr
                275                 280                 285
Thr Thr Thr Cys Ala Thr Ala Cys Thr Thr Ala Thr Gly Gly Thr Thr
            290                 295                 300
Thr Thr Gly Ala Gly Thr Gly Gly Ala Gly Ala Cys Cys Ala Gly Ala
305                 310                 315                 320
Thr Thr Ala Thr Ala Thr Thr Gly Ala Thr Thr Thr Thr Ala Thr
                325                 330                 335
Gly Thr Thr Gly Ala Thr Gly Gly Ala Ala Ala Gly Ala Ala Gly Gly
            340                 345                 350
Thr Thr Thr Ala Thr Ala Gly Ala Gly Gly Thr Ala Cys Thr Ala Gly
            355                 360                 365
Ala Ala Ala Cys Ala Thr Thr Cys Cys Ala Gly Thr Thr Ala Cys Thr
370                 375                 380
Cys Cys Thr Gly Gly Ala Ala Ala Gly Ala Thr Thr Ala Thr Gly Ala
385                 390                 395                 400
Thr Gly Ala Ala Thr Cys Thr Thr Thr Gly Gly Cys Cys Ala Gly Gly
                405                 410                 415
Ala Ala Thr Thr Gly Gly Thr Gly Thr Thr Gly Ala Thr Gly Ala Ala
            420                 425                 430
Thr Gly Gly Cys Thr Thr Gly Gly Thr Ala Gly Ala Thr Ala Thr Gly
            435                 440                 445
Ala Thr Gly Gly Ala Ala Gly Ala Ala Cys Thr Cys Ala Cys Thr
                450                 455                 460
Thr Cys Ala Ala Gly Cys Thr Gly Ala Gly Thr Ala Thr Gly Ala Gly
465                 470                 475                 480
Thr Ala Thr Gly Thr Thr Ala Ala Gly Thr Thr Ala Thr Cys
                485                 490                 495
Cys Ala Ala Ala Cys Gly Gly Thr Ala Gly Ala Thr Cys Thr Gly Cys
```

```
                500             505             510
Thr Gly Gly Ala Gly Gly Thr Cys Ala Thr Gly Gly Ala Gly Ala Thr
            515                 520             525
Gly Thr Thr Gly Gly Ala Ala Thr Gly Cys Ala Thr Gly Thr Thr Ala
        530                 535                 540
Ala Gly Gly Ala Gly Ala Ala Gly Gly Ala Gly Ala Ala Gly Ala Ala
545                 550                 555                 560
Cys Ala Ala Gly Gly Ala Thr Gly Ala Gly Ala Ala Cys Ala Ala Gly
                565                 570                 575
Ala Gly Ala Ala Ala Gly Gly Ala Thr Gly Ala Gly Gly Ala Gly Ala
            580                 585                 590
Gly Ala Ala Cys Ala Ala Gly Ala Cys Thr Cys Ala Ala Gly Ala
        595                 600                 605
Gly Gly Ala Gly Cys Ala Thr Cys Thr Thr Ala Ala Gly Gly Ala Gly
        610                 615                 620
Ala Thr Thr Ala Thr Gly Ala Ala Gly Cys Ala Thr Ala Thr Thr Gly
625                 630                 635                 640
Thr Thr Ala Ala Gly Ala Thr Thr Gly Ala Ala Gly Thr Thr Ala Ala
                645                 650                 655
Gly Gly Gly Ala Gly Ala Ala Gly Ala Gly Gly Cys Thr Gly Thr Thr
            660                 665                 670
Ala Ala Gly Ala Ala Gly Gly Ala Gly Cys Thr Gly Cys Ala Gly
        675                 680                 685
Ala Gly Ala Ala Gly Thr Thr Gly Cys Thr Thr Gly Ala Ala Ala Ala
        690                 695                 700
Gly Gly Thr Thr Cys Cys Ala Thr Cys Thr Gly Ala Thr Gly Thr Thr
705                 710                 715                 720
Cys Thr Thr Gly Ala Gly Ala Thr Gly Thr Ala Thr Ala Ala Gly Gly
                725                 730                 735
Cys Thr Ala Thr Thr Gly Gly Ala Gly Gly Ala Ala Ala Gly Ala Thr
                740                 745                 750
Ala Thr Ala Thr Ala Thr Thr Gly Thr Thr Gly Ala Thr Gly Gly Ala
            755                 760                 765
Gly Ala Thr Ala Thr Thr Ala Cys Thr Ala Ala Gly Cys Ala Thr Ala
        770                 775                 780
Thr Thr Thr Cys Thr Cys Thr Thr Gly Ala Gly Gly Cys Thr Cys Thr
785                 790                 795                 800
Thr Thr Cys Thr Gly Ala Gly Gly Ala Thr Ala Ala Gly Ala Ala Gly
            805                 810                 815
Ala Ala Gly Ala Thr Thr Ala Ala Gly Gly Thr Ala Thr Ala Thr Thr
                820                 825                 830
Ala Thr Gly Gly Ala Ala Ala Gly Gly Ala Thr Gly Cys Thr Cys Thr
            835                 840                 845
Thr Thr Thr Gly Cys Ala Thr Gly Ala Gly Cys Ala Thr Thr Ala Thr
        850                 855                 860
Gly Thr Thr Thr Ala Thr Gly Cys Thr Ala Gly Gly Ala Gly Gly
865                 870                 875                 880
Gly Ala Thr Ala Thr Gly Ala Gly Cys Cys Ala Gly Thr Thr Cys Thr
                885                 890                 895
Thr Gly Thr Thr Ala Thr Thr Cys Ala Ala Thr Cys Thr Thr Cys Thr
            900                 905                 910
Gly Ala Ala Gly Ala Thr Thr Ala Thr Gly Thr Thr Gly Ala Gly Ala
                915                 920                 925
```

-continued

```
Ala Cys Ala Cys Thr Gly Ala Gly Ala Ala Gly Cys Thr Cys Thr
            930                 935                 940
Thr Ala Ala Cys Gly Thr Thr Thr Ala Thr Thr Ala Thr Gly Ala Gly
945                 950                 955                 960
Ala Thr Thr Gly Gly Ala Ala Ala Gly Ala Thr Thr Cys Thr Thr Thr
                965                 970                 975
Cys Thr Ala Gly Ala Gly Ala Thr Ala Thr Thr Cys Thr Thr Thr Cys
                    980                 985                 990
Thr Ala Ala Gly Ala Thr Thr Ala Ala Cys Cys Ala Ala Cys Cys Ala
            995                 1000                1005
Thr Ala Thr Cys Ala Ala Ala Ala Gly Thr Thr Thr Cys Thr Thr
            1010                1015                1020
Gly Ala Thr Gly Thr Thr Cys Thr Thr Ala Ala Cys Ala Cys Thr
            1025                1030                1035
Ala Thr Thr Ala Ala Gly Ala Ala Cys Gly Cys Thr Thr Cys Thr
            1040                1045                1050
Gly Ala Thr Thr Cys Thr Gly Ala Thr Gly Gly Ala Cys Ala Ala
            1055                1060                1065
Gly Ala Thr Thr Thr Gly Thr Thr Gly Thr Thr Thr Ala Cys Thr
            1070                1075                1080
Ala Ala Cys Cys Ala Ala Cys Thr Thr Ala Ala Gly Gly Ala Gly
            1085                1090                1095
Cys Ala Thr Cys Cys Ala Ala Cys Thr Gly Ala Thr Thr Thr Thr
            1100                1105                1110
Thr Cys Thr Gly Thr Thr Gly Ala Gly Thr Thr Thr Cys Thr Thr
            1115                1120                1125
Gly Ala Gly Cys Ala Ala Ala Ala Cys Thr Cys Thr Ala Ala Thr
            1130                1135                1140
Gly Ala Gly Gly Thr Thr Cys Ala Ala Gly Ala Gly Gly Thr Thr
            1145                1150                1155
Thr Thr Thr Gly Cys Thr Ala Ala Gly Gly Cys Thr Thr Thr Thr
            1160                1165                1170
Gly Cys Thr Thr Ala Thr Thr Ala Thr Ala Thr Thr Gly Ala Gly
            1175                1180                1185
Cys Cys Ala Cys Ala Ala Cys Ala Thr Ala Gly Ala Gly Ala Thr
            1190                1195                1200
Gly Thr Thr Cys Thr Thr Cys Ala Ala Cys Thr Thr Thr Ala Thr
            1205                1210                1215
Gly Cys Thr Cys Cys Ala Gly Ala Gly Cys Ala Thr Thr Cys
            1220                1225                1230
Ala Ala Cys Thr Ala Thr Ala Thr Gly Gly Ala Thr Ala Ala Gly
            1235                1240                1245
Thr Thr Thr Ala Ala Cys Gly Ala Gly Cys Ala Ala Gly Ala Gly
            1250                1255                1260
Ala Thr Thr Ala Ala Cys Cys Thr Thr Ala Ala Gly Cys Thr Thr
            1265                1270                1275
Gly Thr Thr Gly Thr Thr Ala Ala Thr Ala Cys Thr Cys Cys Ala
            1280                1285                1290
Thr Thr Thr Gly Thr Thr Gly Cys Thr Gly Thr Thr Thr Thr Cys
            1295                1300                1305
Thr Cys Thr Ala Ala Cys Thr Thr Gly Ala Thr Thr Cys Thr
            1310                1315                1320
Thr Cys Thr Cys Ala Ala Thr Gly Gly Gly Ala Ala Ala Ala Gly
            1325                1330                1335
```

```
Gly Cys Thr Gly Ala Thr Thr Gly Gly Gly Cys Thr Ala Ala Cys
    1340                1345                1350

Gly Gly Thr Thr Cys Thr Gly Thr Thr Thr Thr Ala Ala Cys
    1355                1360                1365

Thr Gly Thr Gly Thr Thr Thr Gly Gly Ala Ala Gly Cys Cys Ala
    1370                1375                1380

Thr Cys Thr Cys Ala Ala Gly Thr Thr Ala Cys Thr Thr Thr Thr
    1385                1390                1395

Thr Cys Thr Ala Ala Cys Gly Gly Ala Ala Ala Gly Ala Thr Gly
    1400                1405                1410

Ala Thr Thr Cys Thr Thr Ala Cys Thr Thr Thr Gly Gly Ala Thr
    1415                1420                1425

Ala Gly Ala Gly Ala Gly Thr Ala Thr Gly Thr Cys Gly Ala Cys
    1430                1435                1440

Cys Ala Thr Cys Ala Thr Cys Ala Thr Cys Ala Thr Cys Ala Thr
    1445                1450                1455

Cys Ala Thr Thr Gly Ala Cys Thr Cys Gly Ala Gly Cys Thr Cys
    1460                1465                1470

<210> SEQ ID NO 14
<211> LENGTH: 482
<212> TYPE: PRT
<213> ORGANISM: B. anthracis

<400> SEQUENCE: 14

Met Gly Gly Ser Tyr Pro Tyr Lys Ser Gly Glu Tyr Arg Thr Lys Ser
1               5                   10                  15

Phe Phe Gly Tyr Gly Tyr Tyr Glu Val Arg Met Lys Ala Ala Lys Asn
                20                  25                  30

Val Gly Ile Val Ser Ser Phe Phe Thr Tyr Thr Gly Pro Ser Asp Asn
            35                  40                  45

Asn Pro Trp Asp Glu Ile Asp Ile Glu Phe Leu Gly Lys Asp Thr Thr
        50                  55                  60

Lys Val Gln Phe Asn Trp Tyr Lys Asn Gly Val Gly Gly Asn Glu Tyr
65                  70                  75                  80

Leu His Asn Leu Gly Phe Asp Ala Ser Gln Asp Phe His Thr Tyr Gly
                85                  90                  95

Phe Glu Trp Arg Pro Asp Tyr Ile Asp Phe Tyr Val Asp Gly Lys Lys
                100                 105                 110

Val Tyr Arg Gly Thr Arg Asn Ile Pro Val Thr Pro Gly Lys Ile Met
            115                 120                 125

Met Asn Leu Trp Pro Gly Ile Gly Val Asp Glu Trp Leu Gly Arg Tyr
        130                 135                 140

Asp Gly Arg Thr Pro Leu Gln Ala Glu Tyr Tyr Val Lys Tyr Tyr
145                 150                 155                 160

Pro Asn Gly Arg Ser Ala Gly Gly His Gly Asp Val Gly Met His Val
                165                 170                 175

Lys Glu Lys Glu Lys Asn Lys Asp Glu Asn Lys Arg Lys Asp Glu Glu
                180                 185                 190

Arg Asn Lys Thr Gln Glu Glu His Leu Lys Glu Ile Met Lys His Ile
            195                 200                 205

Val Lys Ile Glu Val Lys Gly Glu Ala Val Lys Lys Glu Ala Ala
        210                 215                 220

Glu Lys Leu Leu Glu Lys Val Pro Ser Asp Val Leu Glu Met Tyr Lys
225                 230                 235                 240
```

```
Ala Ile Gly Gly Lys Ile Tyr Ile Val Asp Gly Asp Ile Thr Lys His
            245                 250                 255
Ile Ser Leu Glu Ala Leu Ser Glu Asp Lys Lys Ile Lys Asp Ile
        260                 265                 270
Tyr Gly Lys Asp Ala Leu Leu His Glu His Tyr Val Tyr Ala Lys Glu
            275                 280                 285
Gly Tyr Glu Pro Val Leu Val Ile Gln Ser Ser Glu Asp Tyr Val Glu
290                 295                 300
Asn Thr Glu Lys Ala Leu Asn Val Tyr Tyr Glu Ile Gly Lys Ile Leu
305                 310                 315                 320
Ser Arg Asp Ile Leu Ser Lys Ile Asn Gln Pro Tyr Gln Lys Phe Leu
                325                 330                 335
Asp Val Leu Asn Thr Ile Lys Asn Ala Ser Ser Asp Gly Gln Asp
        340                 345                 350
Leu Leu Phe Thr Asn Gln Leu Lys Glu His Pro Thr Asp Phe Ser Val
            355                 360                 365
Glu Phe Leu Glu Gln Asn Ser Asn Glu Val Gln Glu Val Phe Ala Lys
        370                 375                 380
Ala Phe Ala Tyr Tyr Ile Glu Pro Gln His Arg Asp Val Leu Gln Leu
385                 390                 395                 400
Tyr Ala Pro Glu Ala Phe Asn Tyr Met Asp Lys Phe Asn Glu Gln Glu
                405                 410                 415
Ile Asn Leu Lys Leu Val Val Asn Thr Pro Phe Val Ala Val Phe Ser
            420                 425                 430
Asn Phe Asp Ser Ser Gln Trp Glu Lys Ala Asp Trp Ala Asn Gly Ser
        435                 440                 445
Val Phe Asn Cys Val Trp Lys Pro Ser Gln Val Thr Phe Ser Asn Gly
            450                 455                 460
Lys Met Ile Leu Thr Leu Asp Arg Glu Tyr Val Asp His His His His
465                 470                 475                 480
His His

<210> SEQ ID NO 15
<211> LENGTH: 800
<212> TYPE: PRT
<213> ORGANISM: Anthrax antigen

<400> SEQUENCE: 15

Met Thr Arg Asn Lys Phe Ile Pro Asn Lys Phe Ser Ile Ile Ser Phe
1               5                   10                  15
Ser Val Leu Leu Phe Ala Ile Ser Ser Ser Gln Ala Ile Glu Val Asn
            20                  25                  30
Ala Met Asn Glu His Tyr Thr Glu Ser Asp Ile Lys Arg Asn His Lys
        35                  40                  45
Thr Glu Lys Asn Lys Thr Glu Lys Glu Lys Phe Lys Asp Ser Ile Asn
    50                  55                  60
Asn Leu Val Lys Thr Glu Phe Thr Asn Glu Thr Leu Asp Lys Ile Gln
65                  70                  75                  80
Gln Thr Gln Asp Leu Leu Lys Lys Ile Pro Lys Asp Val Leu Glu Ile
                85                  90                  95
Tyr Ser Glu Leu Gly Gly Glu Ile Tyr Phe Thr Asp Ile Asp Leu Val
            100                 105                 110
Glu His Lys Glu Leu Gln Asp Leu Ser Glu Glu Lys Asn Ser Met
        115                 120                 125
```

```
Asn Ser Arg Gly Glu Lys Val Pro Phe Ala Ser Arg Phe Val Phe Glu
        130                 135                 140

Lys Lys Arg Glu Thr Pro Lys Leu Ile Ile Asn Ile Lys Asp Tyr Ala
145                 150                 155                 160

Ile Asn Ser Glu Gln Ser Lys Glu Val Tyr Tyr Glu Ile Gly Lys Gly
                165                 170                 175

Ile Ser Leu Asp Ile Ile Ser Lys Asp Lys Ser Leu Asp Pro Glu Phe
            180                 185                 190

Leu Asn Leu Ile Lys Ser Leu Ser Asp Ser Asp Ser Ser Asp Leu
        195                 200                 205

Leu Phe Ser Gln Lys Phe Lys Glu Lys Leu Glu Leu Asn Asn Lys Ser
        210                 215                 220

Ile Asp Ile Asn Phe Ile Lys Glu Asn Leu Thr Glu Phe Gln His Ala
225                 230                 235                 240

Phe Ser Leu Ala Phe Ser Tyr Tyr Phe Ala Pro Asp His Arg Thr Val
                245                 250                 255

Leu Glu Leu Tyr Ala Pro Asp Met Phe Glu Tyr Met Asn Lys Leu Glu
            260                 265                 270

Lys Gly Gly Phe Glu Lys Ile Ser Glu Ser Leu Lys Lys Glu Gly Val
        275                 280                 285

Glu Lys Asp Arg Ile Asp Val Leu Lys Gly Glu Lys Ala Leu Lys Ala
290                 295                 300

Ser Gly Leu Val Pro Glu His Ala Asp Ala Phe Lys Lys Ile Ala Arg
305                 310                 315                 320

Glu Leu Asn Thr Tyr Ile Leu Phe Arg Pro Val Asn Lys Leu Ala Thr
                325                 330                 335

Asn Leu Ile Lys Ser Gly Val Ala Thr Lys Gly Leu Asn Val His Gly
            340                 345                 350

Lys Ser Ser Asp Trp Gly Pro Val Ala Gly Tyr Ile Pro Phe Asp Gln
        355                 360                 365

Asp Leu Ser Lys Lys His Gly Gln Gln Leu Ala Val Glu Lys Gly Asn
        370                 375                 380

Leu Glu Asn Lys Lys Ser Ile Thr Glu His Glu Gly Glu Ile Gly Lys
385                 390                 395                 400

Ile Pro Leu Lys Leu Asp His Leu Arg Ile Glu Glu Leu Lys Glu Asn
                405                 410                 415

Gly Ile Ile Leu Lys Gly Lys Lys Glu Ile Asp Asn Gly Lys Lys Tyr
            420                 425                 430

Tyr Leu Leu Glu Ser Asn Asn Gln Val Tyr Glu Phe Arg Ile Ser Asp
        435                 440                 445

Glu Asn Asn Glu Val Gln Tyr Lys Thr Lys Gly Lys Ile Thr Val
450                 455                 460

Leu Gly Glu Lys Phe Asn Trp Arg Asn Ile Glu Val Met Ala Lys Asn
465                 470                 475                 480

Val Glu Gly Val Leu Lys Pro Leu Thr Ala Asp Tyr Asp Leu Phe Ala
                485                 490                 495

Leu Ala Pro Ser Leu Thr Glu Ile Lys Lys Gln Ile Pro Gln Lys Glu
            500                 505                 510

Trp Asp Lys Val Val Asn Thr Pro Asn Ser Leu Glu Lys Gln Lys Gly
        515                 520                 525

Val Thr Asn Leu Leu Ile Lys Tyr Gly Ile Glu Arg Lys Pro Asp Ser
        530                 535                 540

Thr Lys Gly Thr Leu Ser Asn Trp Gln Lys Gln Met Leu Asp Arg Leu
545                 550                 555                 560
```

-continued

```
Asn Glu Ala Val Lys Tyr Thr Gly Tyr Thr Gly Gly Asp Val Val Asn
            565                 570                 575

His Gly Thr Glu Gln Asp Asn Glu Glu Phe Pro Glu Lys Asp Asn Glu
            580                 585                 590

Ile Phe Ile Ile Asn Pro Glu Gly Glu Phe Ile Leu Thr Lys Asn Trp
            595                 600                 605

Glu Met Thr Gly Arg Phe Ile Glu Lys Asn Ile Thr Gly Lys Asp Tyr
            610                 615                 620

Leu Tyr Tyr Phe Asn Arg Ser Tyr Asn Lys Ile Ala Pro Gly Asn Lys
625                 630                 635                 640

Ala Tyr Ile Glu Trp Thr Asp Pro Ile Thr Lys Ala Lys Ile Asn Thr
            645                 650                 655

Ile Pro Thr Ser Ala Glu Phe Ile Lys Asn Leu Ser Ser Ile Arg Arg
            660                 665                 670

Ser Ser Asn Val Gly Val Tyr Lys Asp Ser Gly Asp Lys Asp Glu Phe
            675                 680                 685

Ala Lys Lys Glu Ser Val Lys Lys Ile Ala Gly Tyr Leu Ser Asp Tyr
            690                 695                 700

Tyr Asn Ser Ala Asn His Ile Phe Ser Gln Glu Lys Lys Arg Lys Ile
705                 710                 715                 720

Ser Ile Phe Arg Gly Ile Gln Ala Tyr Asn Glu Ile Glu Asn Val Leu
            725                 730                 735

Lys Ser Lys Gln Ile Ala Pro Glu Tyr Lys Asn Tyr Phe Gln Tyr Leu
            740                 745                 750

Lys Glu Arg Ile Thr Asn Gln Val Gln Leu Leu Leu Thr His Gln Lys
            755                 760                 765

Ser Asn Ile Glu Phe Lys Leu Leu Tyr Lys Gln Leu Asn Phe Thr Glu
            770                 775                 780

Asn Glu Thr Asp Asn Phe Glu Val Phe Gln Lys Ile Ile Asp Glu Lys
785                 790                 795                 800
```